US010624673B2

(12) United States Patent
Farnsworth

(10) Patent No.: US 10,624,673 B2
(45) Date of Patent: Apr. 21, 2020

(54) HAND OPERATED REACHING DEVICE FOR REMOVING TICKS FROM ANIMALS OR HUMANS AND METHOD OF USE

(71) Applicant: Wag and Bark Enterprises, LLC, The Woodlands, TX (US)

(72) Inventor: Sheryl Davis Farnsworth, The Woodlands, TX (US)

( * ) Notice: Subject to any disclaimer, the term of this patent is extended or adjusted under 35 U.S.C. 154(b) by 626 days.

(21) Appl. No.: 15/081,921

(22) Filed: Mar. 27, 2016

(65) Prior Publication Data

US 2016/0278811 A1    Sep. 29, 2016

Related U.S. Application Data

(60) Provisional application No. 62/138,970, filed on Mar. 26, 2015.

(51) Int. Cl.
*A61B 17/50* (2006.01)
*A61B 18/00* (2006.01)
(Continued)

(52) U.S. Cl.
CPC .......... *A61B 17/50* (2013.01); *A01M 1/223* (2013.01); *A01M 3/00* (2013.01); *A61B 18/00* (2013.01);
(Continued)

(58) Field of Classification Search
CPC ......... A61B 17/50; A61B 17/52; A61B 17/30; A61B 17/28; A61B 17/2804;
(Continued)

(56) References Cited

U.S. PATENT DOCUMENTS 3,986,061 A    10/1976  Suzuki et al.
4,213,460 A    7/1980   Weiner
(Continued)

FOREIGN PATENT DOCUMENTS

DE    19811464    9/1999
DE    19913210    10/2000
(Continued)

OTHER PUBLICATIONS

English translation of WO 2007088264.*
(Continued)

*Primary Examiner* — Katherine H Schwiker
(74) *Attorney, Agent, or Firm* — Gordon G. Waggett, P.C.

(57) ABSTRACT

A hand held device for removing ticks that are fixed to the skin of an animal or human host and comprises a housing oriented along a longitudinal axis, a tick encapsulation zone at the front end of the housing employing an openable and closable lid section capable of closing around the tick while the tick is attached to the skin of the host. A piezoelectric voltage generation device is located within the housing and activated by a striker to send a high voltage through two lead wires having their distal ends mounted within the tick encapsulation zone in gapped relationship. A trigger is mounted along an axis tangential to the longitudinal axis for triggering the piezoelectric device to send a high voltage across the electrode gap to electrocute the tick. The electrocuted tick automatically becomes detached from the host's skin and falls into the closed encapsulation zone of the device.

7 Claims, 60 Drawing Sheets

(51) Int. Cl.
*A01M 3/00* (2006.01)
*A01M 1/22* (2006.01)
A61B 90/00 (2016.01)
A61B 17/00 (2006.01)
A61B 90/30 (2016.01)

(52) U.S. Cl.
CPC .............. *A61B 2017/00734* (2013.01); *A61B 2017/00902* (2013.01); *A61B 2017/505* (2013.01); *A61B 2018/0047* (2013.01); *A61B 2018/00077* (2013.01); *A61B 2090/309* (2016.02); *A61B 2090/3616* (2016.02)

(58) Field of Classification Search
CPC ............ A61B 17/2812; A61B 17/2816; A61B 17/282; A61B 2017/505; A61B 2017/301; A61B 2017/303; A61B 2017/305; A61B 2017/306; A61B 2017/308; A61B 2017/2808; A61B 2017/2825; A61B 2017/2829; A61B 18/085; A61B 2018/087; A61B 2018/00005; A61B 10/06; A61M 2200/01; A61M 2200/011; Y02A 50/375
USPC ...... 294/99.1, 99.2, 100; 606/131, 210, 211, 606/205–208, 28–32
See application file for complete search history.

(56) References Cited

U.S. PATENT DOCUMENTS

| 4,566,437 | A | * | 1/1986 | Yamaguchi .......... A61B 1/0055 600/131 |
| 4,748,767 | A | | 6/1988 | Sandels |
| 4,976,718 | A | | 12/1990 | Daniell |
| 5,078,729 | A | | 1/1992 | Eichhorn |
| 5,116,347 | A | | 5/1992 | Butler |
| D335,166 | S | | 4/1993 | Johnson |
| 5,374,274 | A | | 12/1994 | Sproviero et al. |
| 5,407,243 | A | | 4/1995 | Riemann |
| 5,554,161 | A | | 9/1996 | Thibeault |
| 5,792,148 | A | | 8/1998 | Laxvik |
| 5,914,062 | A | | 6/1999 | von der Heyde |
| 6,100,501 | A | | 8/2000 | von der Heyde |
| 7,699,869 | B2 | | 4/2010 | Meinhold et al. |
| D740,422 | S | | 10/2015 | Herfort |
| D754,854 | S | | 4/2016 | Farnsworth |
| D755,381 | S | | 5/2016 | Farnsworth |
| D755,382 | S | | 5/2016 | Farnsworth |
| D791,319 | S | | 7/2017 | Farnsworth |
| D791,945 | S | | 7/2017 | Farnsworth |
| 2010/0042094 | A1 | * | 2/2010 | Arts ..................... A61B 18/042 606/34 |
| 2012/0270163 | A1 | * | 10/2012 | Adams ................... F23Q 2/287 431/255 |
| 2014/0148823 | A1 | | 5/2014 | Fitzsimons |

FOREIGN PATENT DOCUMENTS

| DE | 102005008689 | | 8/2006 |
| DE | 202015100015 | | 8/2007 |
| EP | 1424917 | B1 | 8/2007 |
| EP | 1983919 | | 6/2010 |
| EP | 3072464 | B1 | 12/2017 |
| FR | 2896683 | | 10/2008 |
| WO | 0122891 | | 4/2001 |
| WO | 2007088264 | | 8/2007 |

OTHER PUBLICATIONS

Dynavet (Paris, France), brochure displaying Prior Art Tick Pincer device, 1 page. This brochure depicts a prior art device in existence at least one year prior to applicant's effective filing date.
Dynavet (Paris, France), digital photos of Prior Art Tick Pincer device, 6 pages. These photos depict a prior art device in existence at least one year prior to applicant's effective filing date.
travelsolutions4pets.com, screenshot depicting the Prior Art "Essential Pet—Pet Tick-Off Tick Remover" product, 1 page. Webpage published at least as early as Jan. 2015, and last accessed Mar. 25, 2015. This screenshot depicts a prior art device in existence at least one year prior to applicant's effective filing date.
trixticklasso.com, screenshots depicting the "TRIX Tick Lasso" (Sweden) Prior Art tick removal product offered by South Jersey Paws. 10 pages. Webpage published at least as early as Jan. 2015. This is thought to be similar to the device depicted in U.S. Pat. No. 5,792,148 note in the prior IDS. These screenshots depict a prior art device in existence at least one year prior to applicant's effective filing date.
H3D (Lavancia, France), Ticktwister.com screenshots depicting the Tick Twister® Prior Art tick removal product, (2014), 4 pages. These screenshots depict a prior art device in existence at least one year prior to applicant's effective filing date.
dog-breeds.com "Ticks on Dogs", webpage displaying various Prior Art tick removal devices.on p. 3/4. 4 pages. Webpage available at least as early as Jan. 2015. This article was first published at least one year prior to applicant's effective filing date.
tickcard.co.uk "TickCard—Details" (www.tickcard.co.uk/detail), webpage screenshots regarding Prior Art tick removal cards. 6 pages. Webpage published at least as early as Jan. 2015. This NPL references on p. 516 the 2007 EP1424917 patent noted above. These screenshots depict a prior art device in existence at least one year prior to applicant's effective filing date.
Pet Health Pro Tips, pet-health-pro.com website article by Dr. Ellen entitled: How to Remove a Tick From a Cat, Dog or Human. Sep. 17, 2012. 5 pages.
leespring.com, screenshot depicting example prior art Torsion Spring device. 1 page. This screenshot depicts a prior art device in existence at least one year prior to applicant's effective filing date.
Foshan Yiquiand Electronic Co., Ltd., screen shot of "piezo igniter" from the yiqiang.en.alibaba.com website depicting a prior art device in existence at least one year prior to applicant's effective filing date.
greenenergyhelpfiles.com, online article entitled "Piezoelectric Crystals", 1 page, 2014.
webstaurantstore.com, 4-page screenshot regarding "All Points 44/1524 Piezo Spark Igniter with Dual Lead Wires" depicting a prior art device in existence at least one year prior to applicant's effective filing date.
APC International, LTD., screenshots regarding information about piezoelectric generators from www.americanpiezo.com, 6 pages, 2014.
EPO Extended European Search Report and Search Opinion in counterpart European Patent Application No. 16162611.4. dated Aug. 26, 2016. 6 pages.

\* cited by examiner

HAND OPERATED REACHING DEVICE FOR REMOVING TICKS FROM ANIMALS OR HUMANS AND METHOD OF USE

CROSS-REFERENCE TO RELATED APPLICATIONS

This application claims the benefit of the filing date of and priority to: U.S. Provisional Application Ser. No. 62/138,970 entitled "Hand Operated Reaching Device for Removing Ticks from Animals or Humans and Method of Use" and filed Mar. 26, 2015, Confirmation No. 5606; said provisional application is incorporated by reference herein in its entirety for all purposes.

STATEMENT REGARDING FEDERALLY SPONSORED RESEARCH OR DEVELOPMENT

Not Applicable.

BACKGROUND OF THE INVENTION

Field of the Invention

The present disclosure relates generally to the field of tick removal devices used to remove ticks from humans or animals. More particularly, the present disclosure is directed to an instrument and method for removing ticks from human or animal skin by lethally neutralizing the tick.

Process of Tick Attachment

Ticks (arachnids) are parasites that affix themselves to the skin of their host (animal or human), in order to feed from the host's blood supply. "Questing" (various behaviors used by ticks in order to source/identify a host for its blood meal), is prompted by one or all of the following: heat, movement/vibration, and carbon dioxide. After questing, the tick attaches and feeds for approximately three to ten days (3-4 days for nymphs; 7-10 days for adult females). As the tick attaches, it embeds its hypostome (mouthpart/feeding tube) into the host's skin. A cement-like substance is secreted keeping the tick firmly attached during the duration of attachment/feeding. Secreted painkillers known as "kininases" are passed to the host via the tick's saliva during feeding, enabling the ticks to remain attached longer without detection by its host. The tick's saliva travels into the wound/attachment area and serves to prevent the host's blood from clotting.

Health Kicks

Ticks transmit the widest variety of pathogens of any blood sucking arthropod, including bacteria, rickettsia, protozoa, and viruses. In addition to these and many other diseases, ticks can also release toxins that cause what is referred to as "tick bite paralysis". These toxins affect the nervous system (temporary or permanent loss of voluntary movement, possible respiratory muscle paralysis), in both humans and dogs.

If the tick carries pathogens, the toxic, blood borne organism may be transmitted to the host, leading to disease (e.g. Lyme disease, etc.).

If the host carries pathogens, the toxic, blood borne organism may be transmitted to the tick, leading to disease for future hosts, as a tick will transmit the toxins, and, may have multiple hosts during its lifetime. These processes render the tick a "disease vector".

Due to the risk of blood borne disease and skin infection, it is imperative that ticks be removed from their hosts as soon as possible, while also removing the rostrum from the skin (which may cause skin infections) in a safe manner.

Tick Removal Risks

Provocation in the Head Area:

If a tick is squeezed/pinched/compressed around the head area (intentionally—during an attempt to remove the tick, etc.; or unintentionally—while grooming, scratching, etc.), the tick may regurgitate the infected blood stored in its idiosoma (via the rostrum/embedded mouthpiece), into the host (making the host a "disease reservoir" for other ticks).

Provocation in the Abdominal Area:

If a tick is squeezed/pinched/compressed in the abdominal area, it will provoke the tick to disseminate toxic products in to the environment, and, possibly to lay its eggs.

There Remains a Need for Safe Tick Removal Devices and Methods

Various prior art devices have been designed for removal of a tick from a human or animal. However, these prior art devices have deficiencies that can lead to the unsafe removal of the tick.

For example, U.S. Pat. No. 4,976,718 (Daniell), entitled "Parasite Remover" describes a forceps for removing a parasite such as a tick from a human or animal host where the parasite has attached itself to the host at its head and the parasite contains fluids which can be expelled into the host upon the application of an external squeezing force, particularly a squeezing force applied to the body of the parasite. The forceps includes first and second arms each having a distal end and a proximal end and secured so that they are movable in opposition to one another between an open position and a closed position. A gripping section for engaging the parasite is mounted on the distal end of the forceps. The gripping section includes first and second sets of interdigitating teeth mounted on each of the opposed arms that are sized to closely surround the body of the parasite without crushing or squeezing any part of the parasite's body when the arms are in the closed position. The gripping section also has a portion mounted at the extreme distal end of the opposed arms with an oval opening formed in the extreme end portion when the opposed arms are in their closed position. The oval opening acts to closely grip and surround the head or neck of the parasite without crushing it. The parasite can be completely and quickly removed from the host without causing the parasite to expel disease containing fluids back into the host. However, the pliers/pinchers of Daniell have concave extremities bearing teeth that are used to imprison the tick at its head (rostrum/embedded mouthpiece), and thus remains attached to the head during extraction. This instrument does not allow for the tick to be extracted while also ensuring that the rostrum (embedded mouthpiece) does not remain in the skin of the host. This instrument applies compression around the rostrum, an action that naturally provokes injection of toxic substances via the rostrum, and may also provoke a possible response of implantation of eggs by the tick, into its host.

U.S. Pat. No. 5,116,347 (Butler) entitled: "Tick remover for people and animals" describes (from the abstract) a simple hand-held implement for removing ticks and other ectoparasites or small undesirable objects from the cutaneous areas and clothing of humans and animals. However, these pliers, which have extremities in the form of a spoon, pinch the animal around the head (rostrum/embedded mouthpiece), for extraction purposes, and thus remain attached to the head during extraction. This instrument does not allow for the tick to be extracted while also ensuring that the rostrum (embedded mouthpiece) does not remain in the skin of the host. This instrument applies compression around the rostrum, an action that naturally provokes injection of toxic substances via the rostrum, and may also provoke a possible response of implantation of eggs by the tick, into its host.

U.S. Pat. No. 4,748,767 (Sandels) entitled: "Insect (tick) remover" describes (from the abstract) an arrangement to suffocate a tick or another insect which has stuck on to the skin of a man or an animal. The setup consists of a cup-shaped body, which glues on to the skin over the tick. A filling injects in the cup-shaped body's interior through one aperture at the same time as the air in the space evacuates through another aperture. Owing to this the tick will suffocate so that it releases its hold and can be removed without leaving any remains in the skin. In another shape the setup can be provided with an aperture and a ventilator to merely evacuate the air so that the insect stifles. However, the device of Sandels is not easy to use as the user must ensure that the skin is air-tight (no air may enter into the vacuum cup for a successful result); this will be extremely difficult to accomplish as most animals have fur/humans have hair—on the surface of their skin. When the cup is lifted to remove the tick, the user runs the risk of making contact with the potentially diseased tick, as it is no longer contained by the cup. The risk of potential infection to humans, animals, as well as the environment, is increased as the tick is not encapsulated, and may fall away prior to proper disposal. This is not hygienically satisfactory.

German Patent reference DE19913210A1 (Mezger) entitled: "Tick pincers for removal of ticks from human or animal skin have power source and generator for application of charge to tick so that it can be killed without squashing it" describes tick pincers that have pincer levers with a forward conducting end that is connected via isolated conductors to a switch and a power source and high voltage generator in the handle of the pincers. The pincer user activates the switch to supply an electric charge to the end of the pincers and kill the tick. The Mezger device employs pincers/pliers that have round electrical end points, electrical conductors allowing for the electrocution of the tick. These pincers are relatively cumbersome, which could impede the successful termination of the tick. This unit requires a battery, which could potentially limit its usefulness, as a dead or uncharged battery renders the unit unavailable. The design of the tool's extremities does not guarantee that the host is not receiving the electrical charge as well as the tick. The tick is not guaranteed to be electrically isolated.

U.S. Pat. No. 4,213,460 (Weiner) entitled: "Tick removing forceps" describes (in the abstract) a forceps including a pair of closable arms having cup-shaped gripping members affixed to the ends of the arms and adapted to be closed upon and to grip the protruding portion of a tick or other parasite which is attached through biting engagement to the skin of a host animal. At least one of the gripping members is provided with either an electrical thermal element or a chemical agent applicator affixed to its inner surface and adapted, when applied to a tick or parasite, to cause the latter to release its bite whereupon it can be easily, hygienically, and painlessly removed from the skin of the host animal by a retraction force applied via the forceps. However, these pincers/pliers have round electrical end points, electrical conductors allowing for the electrocution of the tick. These pincers are relatively cumbersome, which could impede the successful termination of the tick. The design of the tool's extremities does not guarantee isolation of the tick, as the closure of the cup relies on the ability of the user to control the opening and closing actions. As the cup closure is not guaranteed, then the isolation of the tick would not be guaranteed as well. These pincers/pliers may utilize either a heated element or a chemical stimulant to kill the tick. Using a heated element poses an issue as this may burn the host's skin while killing the tick. Using a chemical stimulant may prompt a chemical reaction by the host.

German patent application publication DE 10 2005 008 689 A1 (Aug. 31, 2006) (Keicher) describes a tweezer-based tick removal device. The tweezers (located at the proximal end of the device) have a tubular base body (2) with a pliers body in its internal space with pliers-like gripper arms (13, 14) that can be closed and opened with a displacement mechanism. The base body also has an element that produces a high voltage with a high voltage electrode (9) that is exposed and a trigger mechanism (12) located at the distal end of the device. This device does not encapsulate the tick. An independent claim is also included for a method of killing a tick.

German patent application DE 198 11 464 C1 (Sep. 10, 1999) (Dehn) and WO 0122891A1 (Dehn) relate to a loop-style tick removal device. This tool uses a loop, extending from the unit, to 'lasso' the tick and deliver an electrical current. The tick remover which is flattened or bluntened at the frontal end (11) of a housing (1). Two bores (8) are located at said end from which a loop (3) emanates in order to throttle the tick. A rod (5), which is accessible from outside said casing via a pusher (2) and is intended for moving the loop, is located on the inside of said housing. Said rod (5) and is pushed forward against the force of a spring (4) and, after release, can be moved back by virtue of the action of said spring and the loop can be drawn together.

U.S. Pat. No. 5,554,161 (Thibeault) describes a tool for removing ticks and similar parasites. A spoon-shaped tool, the spoon of which is split lengthwise and hinged to rotate the split spoon sections normally open far enough to fit over a tick's body, then rotated closed into an overlapping relationship by thumb and forefinger closing pressure to trap the tick about the neck in a v-shaped slit in one side of the opening in the spoon. A mechanical stop prevents the slit from closing completely to sever the tick from its head. The handle may have a centerline hinge, integral spring, and thumb and finger locators to facilitate use of the tool in a palm-down fashion by either hand. The spoon sections may have opposing slits that close upon each other to likewise trap the tick. The tick is at all times visible in the open bowl of the tool. The tool may be molded in one piece, with a "living hinge" and spring incorporated into its design.

U.S. Pat. No. 7,699,869 (Meinhold et al.) relates to a device, in particular, for the removal of parasites or ticks from the skin of animals or humans, comprises a housing, a spreading gripping tool, a spreading device, for spreading the gripping tool and a rotation device, for rotating the gripping tool about the axis of the device, whereby the gripping tool encloses a sealed cavity in the unspread state thereof for enclosing the parasite or the tick. The gripper tool is particularly made from an elastic or flexible material.

U.S. Pat. No. 5,374,274 (Sproviero et al.) discloses a tick extracter consisting of a pair of manually operable, electrically insulated jaws in the form of tweezers adapted to grasp the body of the tick, and an electrical source to supply one or more electrical pulses to the jaws so as to jolt the tick and cause it to loosen its grip on the flesh of the victim. The electrical source can be a piezo-electric crystal connected to the jaws of the tweezers by a flexible electrical cord, and can be manually controlled as by another hand, to effect the production of the electrical pulses from the crystal.

U.S. Design Pat. No. D335,166 (Johnson) is entitled Combined woodtick and leech remover" and appears to employ a pen-like shape with a needle point at the proximal end. There appears to be a switch located on the outside of the device, but the function is not known.

One product on the market is called "Essential Pet—Pet Tick-Off Tick Remover" offered by travelsolutions4pets.com. This is a battery operated device that works just like a penlight. Place the tip near the head of the tick and press the ON button. Heat will then emanate from the tip, and the tick will immediately back itself out of the pet. The user is then instructed to simply brush it off and dispose of it.

Another product on the market is called "TRIX Tick Lasso" offered by trixticklasso.com. This tick removal device employs a pen-like device with a loop on the proximal end for lassoing the tick. It is touted as removing the whole tick, head and all. It notes that other tick removers such as tweezers fail and often remove only the tick body, leaving the head in the skin. The device contains a loop that is retractable into the pen body. Pushing on the end of the pen body brings the loop out. The user then presses down the loop button to release the loop and puts the loop over the tick, as close to the skin as possible. The user then releases the loop button and tilts the tick remover perpendicularly against the skin causing the loop to retract around the tick (the lasso principal). The user then twists the pen 360 degrees between the user's fingers to physically remove the tick. This device is related to that described in U.S. Pat. No. 5,792,148 (Laxvik).

Another device on the market is the Tick Twister® tick removal device available from TICKTWISTER.COM. This device employs a handle with a hook or fork end at one end. The prongs of the fork are placed around the tick, and the tick is removed with a twisting motion. Other tick removal devices employ tweezers to pinch and pull out the tick. Still other devices use a flat card-like device with prongs to extend around the tick to facilitate removal. Other methods—tweezing, matches and burning, tick keys, tick removal sprays, and tick removal chemicals require the user to touch the tick.

EP Patent No. 1983919 B1 (Schaumburg) entitled: "Instrument for removing ticks that are fixed to the skin" discloses (from abstract) an instrument, for removing ticks that are fixed to the skin of an animal or of a human being, comprising two parts that are movable relative to one another, each part comprising a member (9, 16) that is designed to define, with the other member (16, 9), a closed volume (18) in which the body and the head (19) of a tick (20) are held without compression. This volume (18) is provided with a neutralizing means connected to a piezoelectric generator designed to deliver, to the neutralizing means, an electrical voltage that produces an electric shock lethal to the tick.

In particular, referring to the figures and figuring numbering in the Schaumburg patent (the figure numbering herein being placed within parenthesis to distinguish from the numbering used later to describe the instant drawings), the Schaumburg patent claims define an instrument for removing ticks that are fixed to the skin of an animal or human being, the instrument containing a body (2) and two parts movable in relation to one another, the parts (2, 10) each containing a component (9, 16) for defining an enclosed space (18) with the other component (16, 9) to hold the body and head (19) of a tick (20) without compression, the space (18) being supplied with a means of lethal neutralization (220) for the tick (20) connected to a piezoelectric generator (21) for supplying an electric voltage to the means of neutralization to cause a lethal electric shock to the tick, characterized in that the piezoelectric generator (21) is inserted into the body (2) of the instrument and is actuated by displacement of a cap (23) covering one end of the body (2) of the instrument.

The Schaumburg device is aligned along a longitudinal axis with the components (9, 16) being located at the proximal end of the device and the cap (23) being located at the opposite, distal end of the device along this longitudinal axis. The cap (23) moves inwardly (and back out) along the longitudinal axis. Schaumburg further teaches that the electric voltage supplied to the means of neutralization (220) by the piezoelectric generator (21) may be at least 17,000 volts. The piezoelectric generator (21) may be equipped with a device to prevent a drop in the electric voltage supplied to the means of neutralization (220) over time. The device may further comprise an electric capacitor discharging into an electric coil to amplify and linearize the voltage supplied by the piezoelectric generator (21). The components (9, 16) may each define a hemisphere, one of which (9) is fixed to one end (8) of the body (2) of the instrument, the other hemisphere (16) being fixed to one end of an arm (10) which is movable in relation to the body (2).

One of the components in the Schaumburg device (16) has a break (17) forming an opening for the head (9) of a tick (20). The piezoelectric generator (21) feeds two electric conductors (220) arranged on either side of the opening (17), the conductors (220) being able to produce an electric arc when the components (9, 16) form the enclosed space (18). The piezoelectric generator (21) feeds at least one electric conductor (220) in each component (9, 16), located on the inner face, the conductors (220) being able to produce an electric arc when the components (9, 16) form the enclosed space (18). Schaumburg also teaches that at least one component (9, 16) may be manufactured in a transparent material, and that the transparent component may form a magnifying glass or otherwise contain a zone of magnification. The body (2) of the instrument holds one of the components (9) while the other component is held by an arm (10) mounted movably on the body and in that the body is equipped with a means (24) of position return of the movable arm (10) to a position in which the components together define the enclosed space (18) to hold the tick (20).

As such, Schaumburg describes an instrument that enables the user to remove attached ticks from the skin of humans or animals. This instrument is easy to apply, and at first glance, appears to have satisfactory conditions of hygiene . . . avoiding the disbursement of toxic products and/or eggs at the time of extraction . . . ensuring the extraction of the tick without leaving a part of the rostrum in the host. Also, the Schaumburg device appears to avoid injection of the toxic products by the tick while extraction is taking place. There is no bulkiness to the apparatus and there appears to be no risk to animal/host. The inventor/applicant has previously sold and distributed a device under the trademark "TICKZAPPER®" employing the Schaumburg technology. The teachings of EP Patent No. 1983919 B1 (Schaumburg) are incorporated herein by reference.

The Schaumburg instrument uses a piezoelectric charge that lethally neutralizes ticks. The energy source provides 17,000 volts of current. Although a very good invention, the energy source is not strong enough to kill the tick on the first attempt, and requires a minimum of two to three executions. The additional executions required for full effect affords the tick an opportunity to inject toxic products into the host, and/or, lay eggs onto the surface of the host's skin. This creates a potentially toxic condition for the host.

Additionally, the Schaumburg instrument requires that the user first secure the cup (located at the proximal end of the device) over the tick, then click the opposing end cap (23) of the device for electrocution. The clicking motion requires pressing the cap (23) inwardly along the longitudinal axis toward the proximal end. Although an effective means by which to kill the tick (via numerous clicking), this process also alerts the tick to its potential removal from its host. Ticks are able to sense heat, vibration, and carbon dioxide—all three items are presented by humans when approaching a tick. Therefore, during the time it takes the user to properly secure the cup and depress the clicker (and this is a variable, as it is user-dependent), the tick could be infecting its host. Furthermore, the materials and housing are not strong enough to withstand more than fifty executions, approximately. The Schaumburg unit cannot prime itself with internal, useable energy prior to applying to the tick. The current method requires that the proximal end of the unit first be positioned onto the tick, then, the user must click the opposing end cap to move the cap towards the proximal end along the longitudinal axis to instigate the electrical charge. This creates difficulty for the user to hold the device in one hand and then click the end cap with the same hand. Further, where two hands are used, holding the device in one hand while clicking the end cap with the other hand creates a stability issue that will jostle the tick during the process.

Therefore, there remains a need to develop a hand held tick removal device that avoids the above-mentioned deficiencies.

BRIEF SUMMARY OF INVENTION

The present invention (also sometimes referred to as an improved TickZapper™ device) addresses these needs by providing such a device and method of use of the device.

The neurological and enzymatic systems of the tick affect the anchoring of the tick's rostrum, and, the injection of toxic substances into the host. By piezoelectric neutralization, the natural 'unhooking' of the tick is assured, which avoids the phenomena of the liberation of toxic substances into the host—by rostrum (mouth) or abdomen—as the body of the tick is not submitted to any compression. A lethal electric shock, in a closed apparatus, acts rapidly on the insect without touching the host (animal or human). Once dead, the tick detaches itself naturally without leaving any part of the rostrum in the skin, and without any release of toxic substances or eggs. Where the tick has been killed in this manner, the tick can therefore—in a hygienic way—with no contact with user or host, be discarded. By disposing of the tick after its extraction in a closed apparatus, there will be no compression of the tick's head or body. A deceased tick can be easily be disposed of into a collection system (for sampling) or simply destroyed (fire, flushing, etc.) using accepted protocol.

In one embodiment there is disclosed a hand held reaching device for removing ticks that are fixed to the skin of an animal or human host comprising: (a) an external housing having a front proximal end and a rear distal end oriented along a horizontal axis, (b) a tick encapsulation zone defined by a fixed portion of the front end of the housing, and an openable and closable lid section capable of moving from an open position to a closed position to create a closed enclosure within the front end of the housing, the lid portion capable of closing around the tick while attached to the skin of the host, the lid further comprising a button to push to pivotally open the lid and a spring mechanism to provide resistance sufficient to maintain the lid in a closed position unless the lid button is pressed, (c) a piezoelectric crystal voltage generation device located within the housing, (d) a striker for striking the piezoelectric crystal to generate a high voltage, (e) two lead wires from the piezoelectric crystal having their distal ends mounted within the tick encapsulation zone in gapped relationship proximate to the housing first end, and (f) a trigger mechanism oriented about an axis tangential to the longitudinal axis of the housing, for triggering the striking of the piezoelectric device by the striker to send a high voltage through the lead wires and across the electrode gap to electrocute the tick. The trigger is preferably located distal to the tick encapsulation zone along the longitudinal axis. The electrocuted tick becomes detached from the host's skin and falls into the closed encapsulation zone of the device where it can be safely disposed of in a desired fashion by opening the lid.

In one embodiment, the lid or hatch of the tick removal device is transparent. In another embodiment, the transparent lid also comprises a magnification zone to facilitate viewing the tick and the tick detachment.

In one embodiment, the trigger is tangentially mounted within the housing along a trigger axis, the trigger axis intersecting with the longitudinal axis to form a trigger axis angle comprising the angle taken from the proximal side of the trigger relative to the longitudinal axis. In one embodiment, the trigger axis angle is approximately 135°. The trigger angle can range from about 90° to about 160°, or more particularly, between about 120° to about 150°.

The hand held reaching device may also employ suitable gripping surfaces on the outside surface of the housing to facilitate the one-handed gripping of the device when in use.

There is also disclosed a method of using such new hand held reaching device to remove ticks from a human or animal host's skin. The user hold the device with one hand and then presses the user's thumb of such hand down onto the lid button to open the lid against the force of the spring action. The user then places the lid opening up attains the host's skin over the tick so that the tick is located between the electrode tips. The user then gently releases the lid button with the thumb to close the lid around the tick, and then easily moves the user's thumb from the lid button back to the trigger and pushes the trigger with same thumb to activate the piezoelectric voltage across the electrode tips. The dead tick then detaches from the host's skin and falls into the encapsulation zone. The user can then take the hand held device to a desire location, reopen the lid, and empty the dead tick out of the encapsulation zone into a desired disposal location. If desired, while the device still surrounds the tick up against the host's skin, the device may be rotated after pressing the trigger to facilitate detachment of the tick from the host's skin.

In one embodiment, the device may be outfitted with an LED light to provide light in the encapsulation zone to facilitate tick removal in darkness or low light conditions. In another embodiment, the tick removal device is a single-use, disposable device.

DETAILED DESCRIPTION OF THE INVENTION

Figure 1:
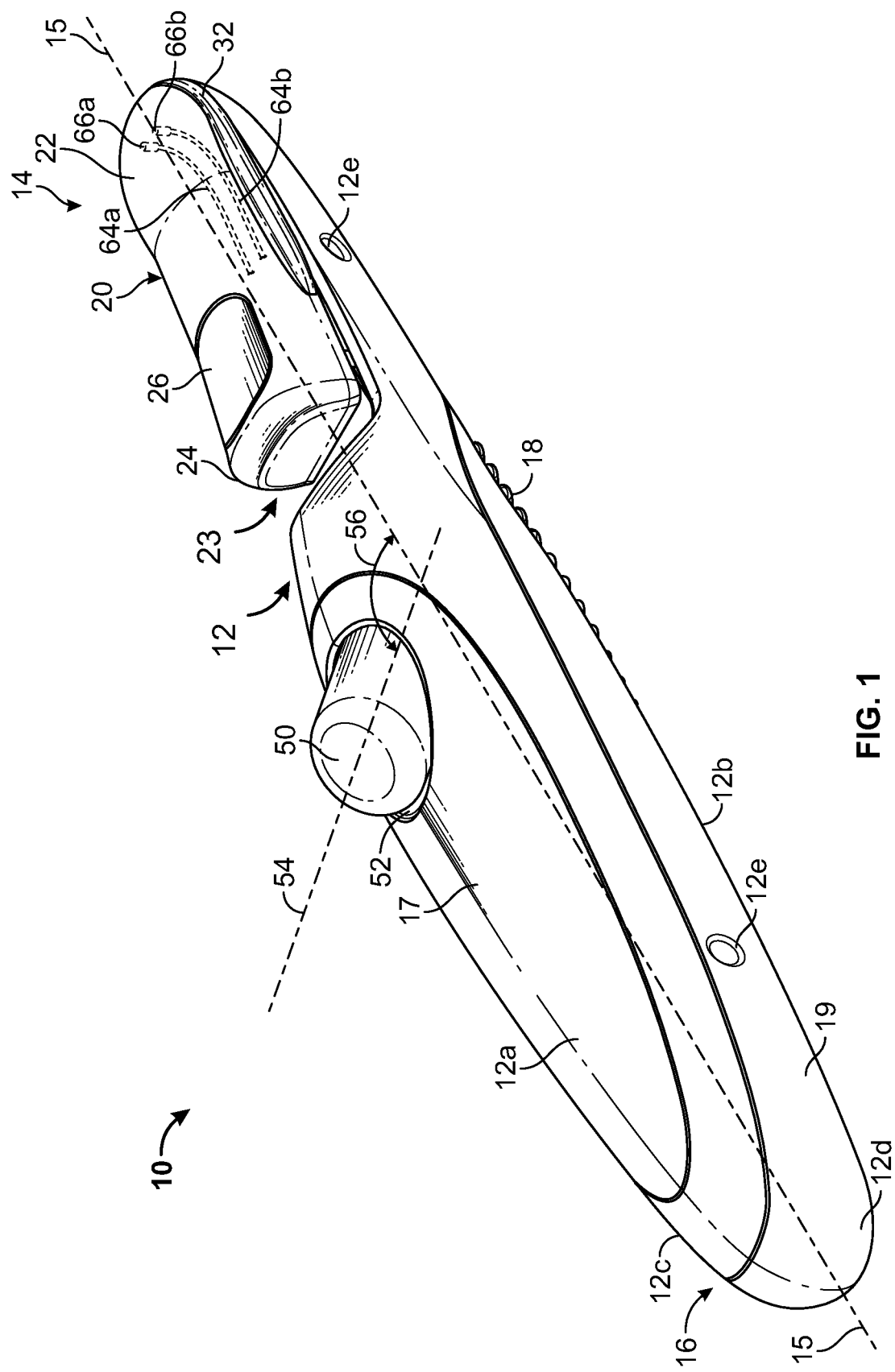
FIG. 1 is a rear, right side perspective view of a hand operated reaching device for removing ticks from animals or humans according to one embodiment of the present disclosure shown with the hatch or lid in the closed position.
Figure 2:
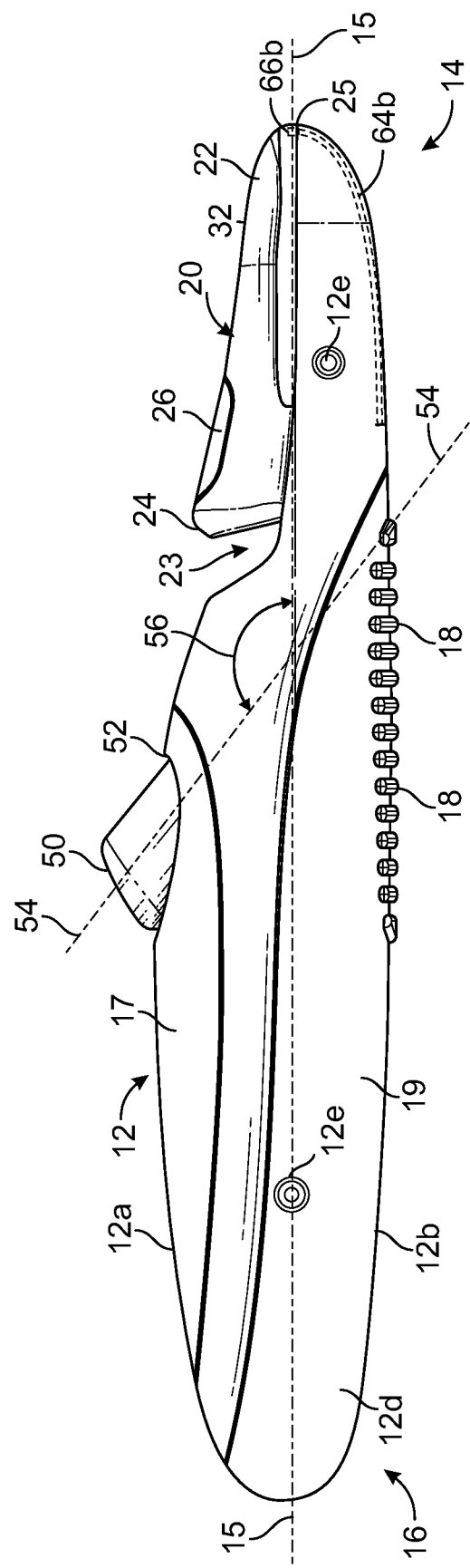
FIG. 2 is a right side plan view of the embodiment of FIG. 1.
Figure 3:
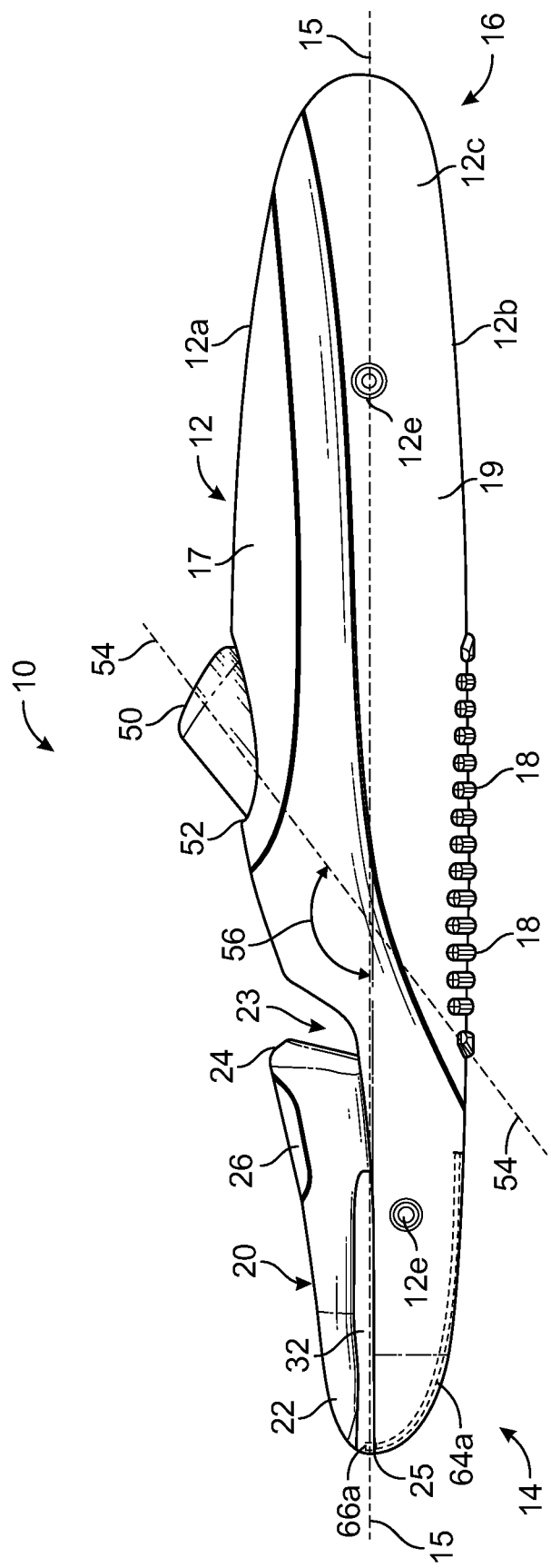
FIG. 3 is a left side plan view of the embodiment of FIG. 1.
Figure 4:
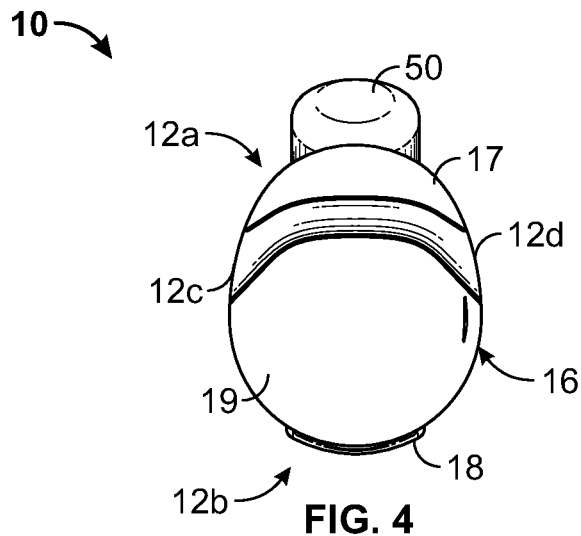
FIG. 4 is a rear end plan view of the embodiment of FIG. 1.
Figure 5:
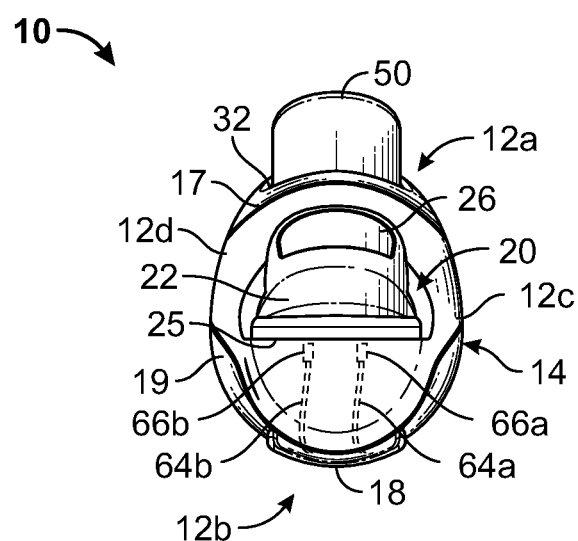
FIG. 5 is a front end plan view of the embodiment of FIG. 1.
Figure 6:
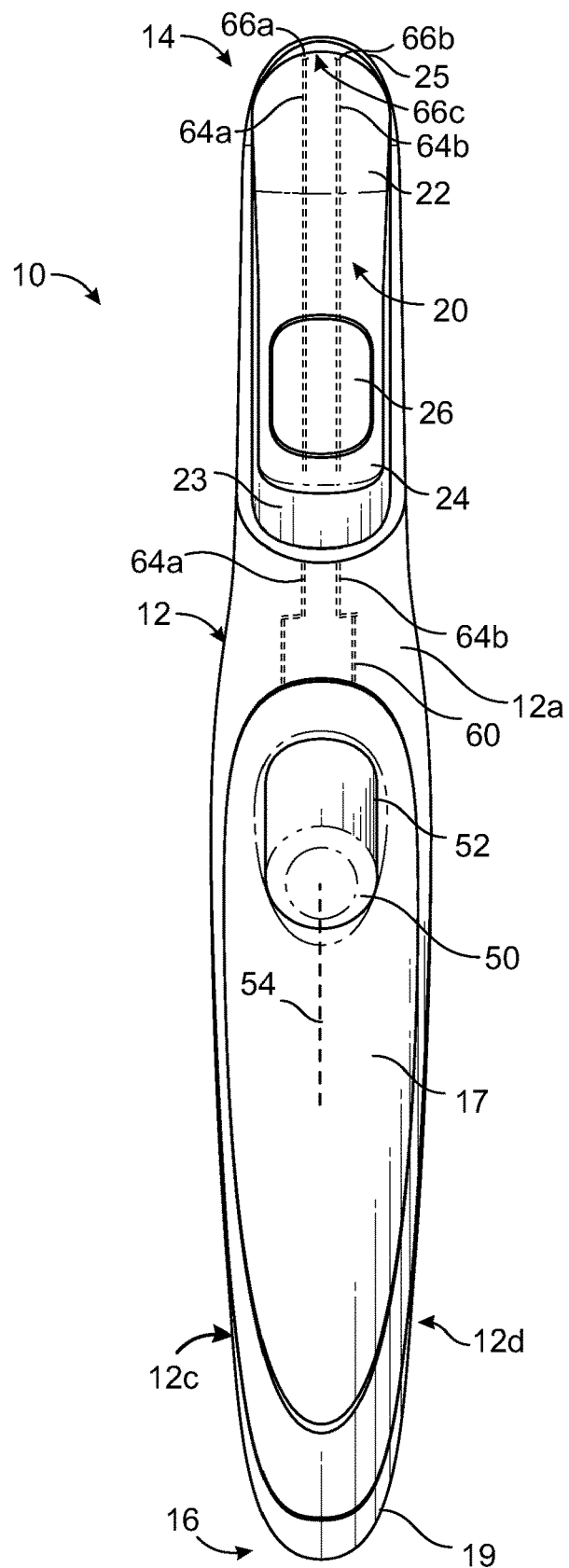
FIG. 6 is a top plan view of the embodiment of FIG. 1.
Figure 7:
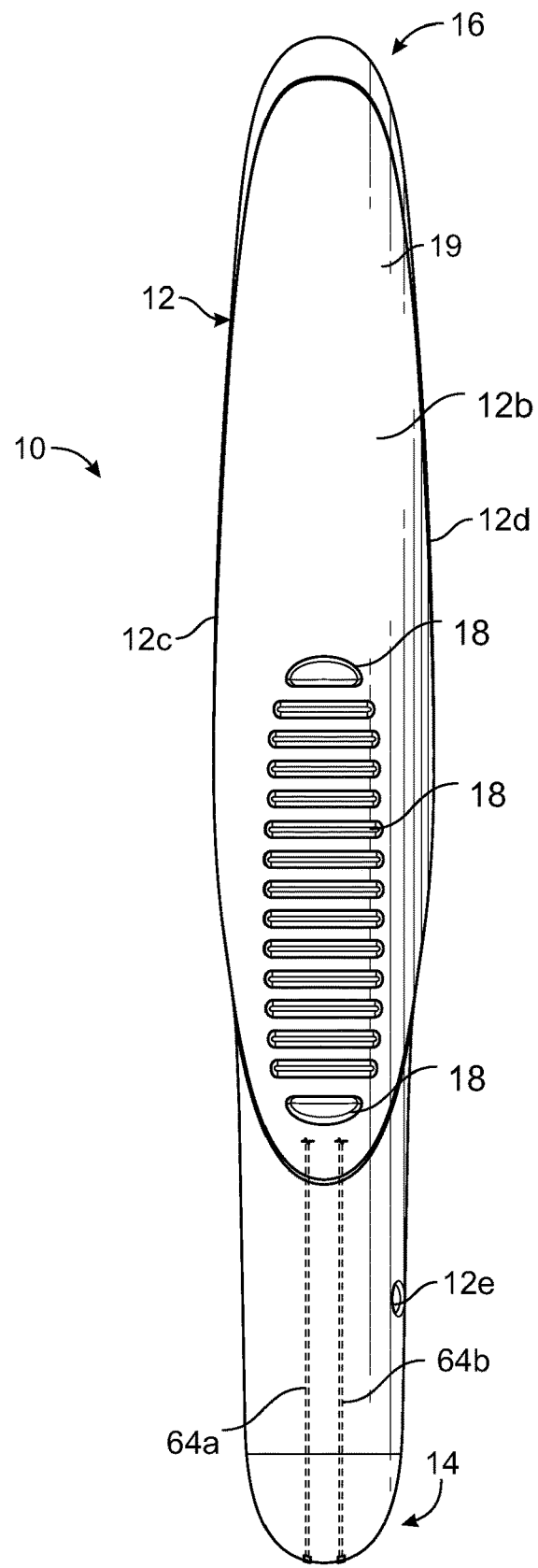
FIG. 7 is a bottom plan view of the embodiment of FIG. 1.
Figure 8:
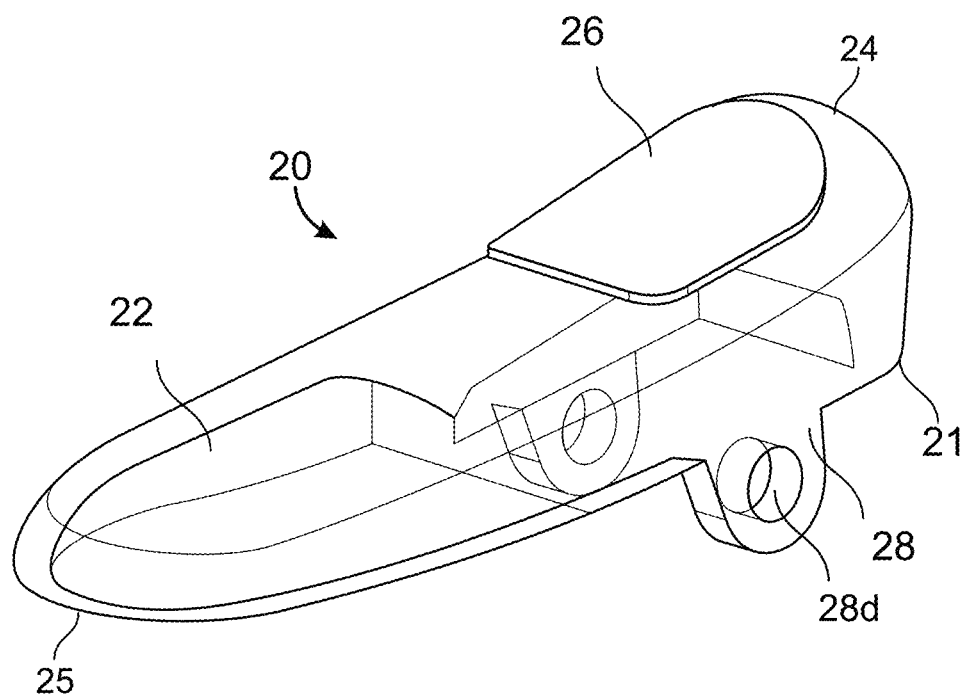
FIG. 8 is a front left top side perspective view of the hatch used in the embodiment of FIG. 1.
Figure 9:
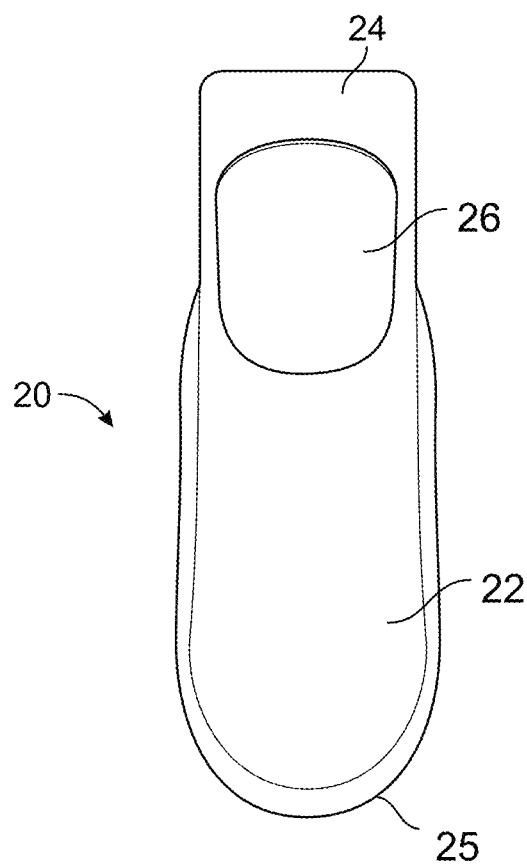
FIG. 9 is a top plan view of the hatch embodiment of FIG. 8.
Figure 10:
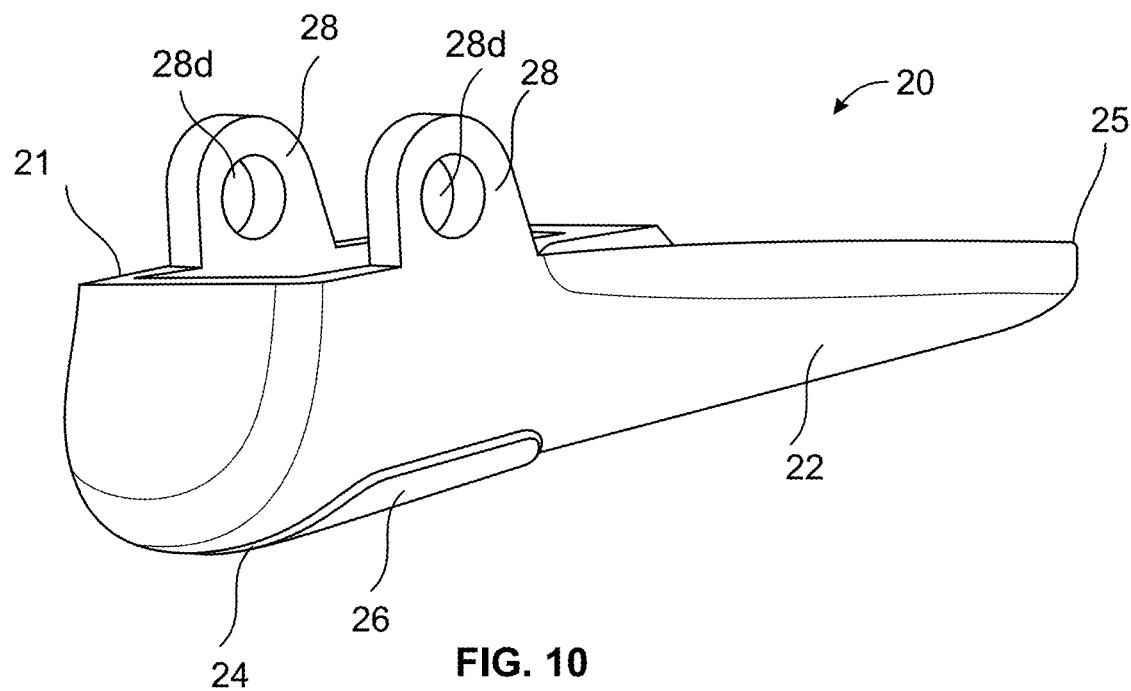
FIG. 10 is a rear left underside perspective view of the hatch embodiment of FIG. 8.
Figure 11:
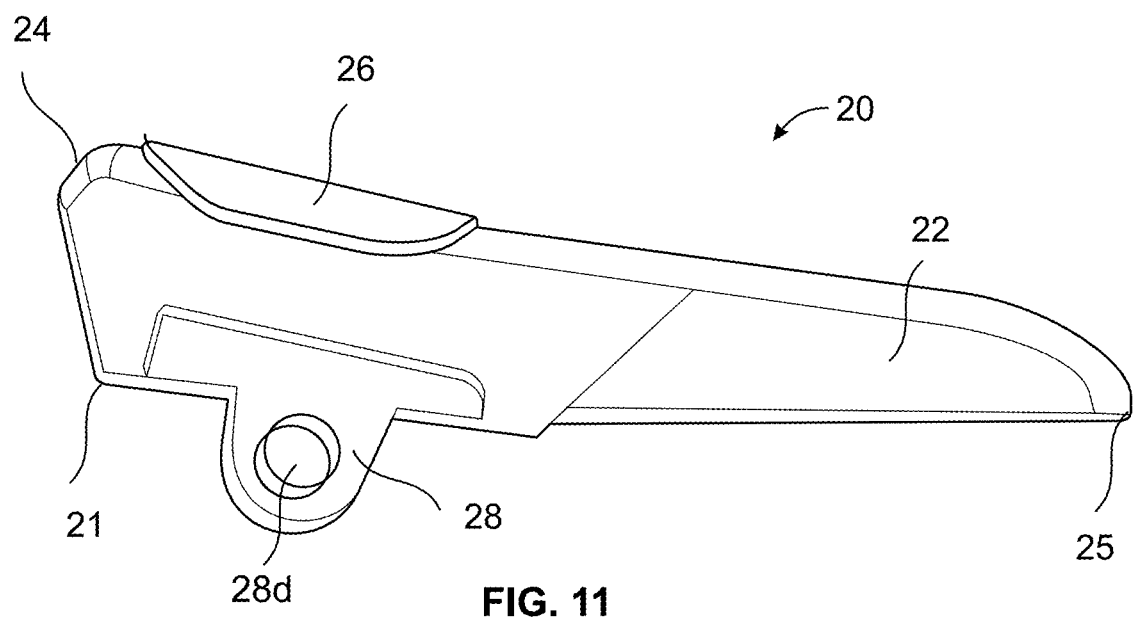
FIG. 11 is a right side plan view of the hatch embodiment of FIG. 8.
Figure 12:
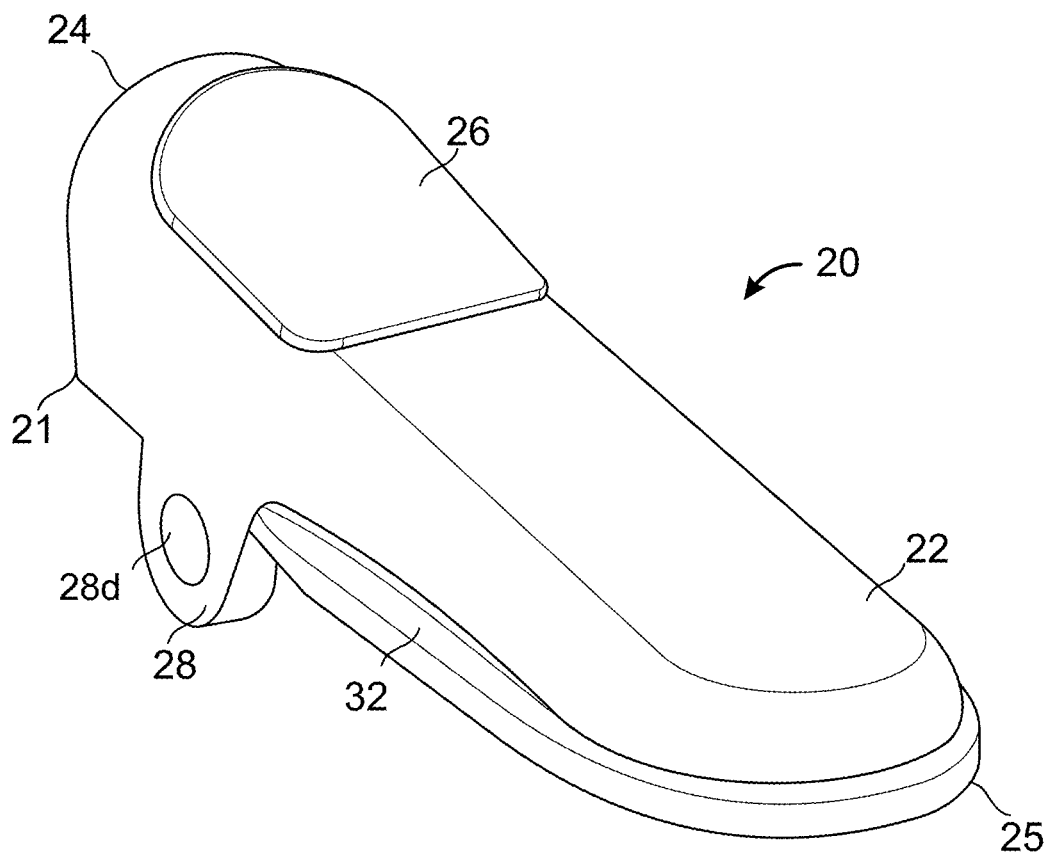
FIG. 12 is a front right top side perspective view of the hatch embodiment of FIG. 8.
Figure 13:
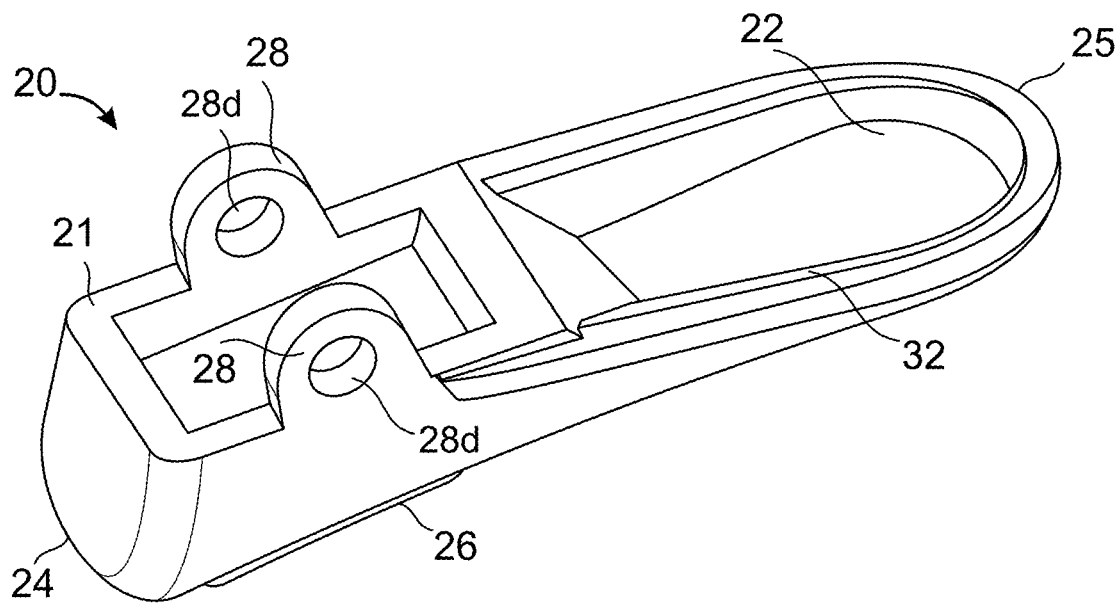
FIG. 13 is an underside perspective view of the hatch embodiment of FIG. 8.
Figure 14:
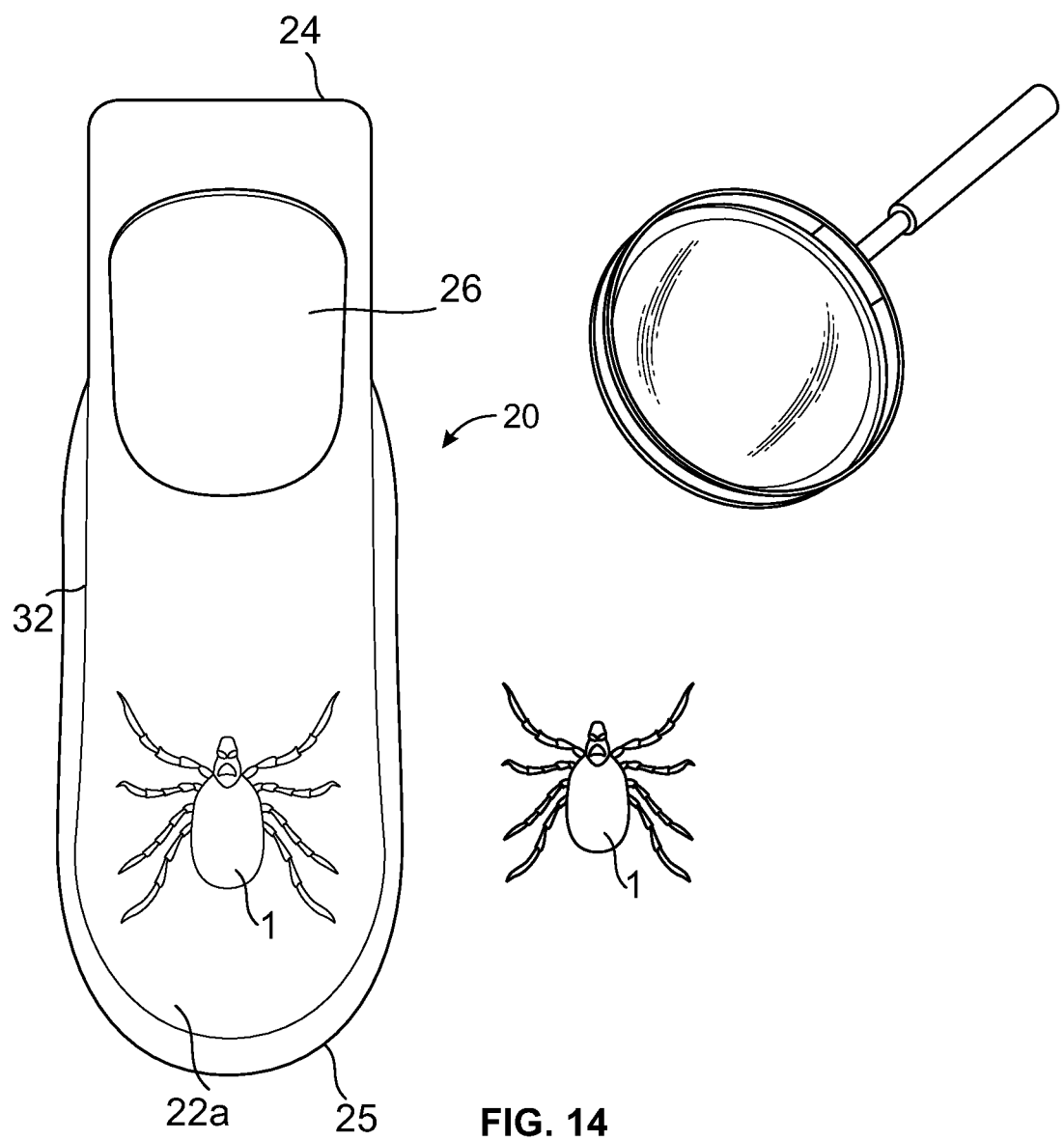
FIG. 14 is a top plan view of the hatch embodiment of FIG. 8 illustrating that the hatch is see-through and may employ magnification in the top of the hatch to enhance visibility of the tick.
Figure 15:
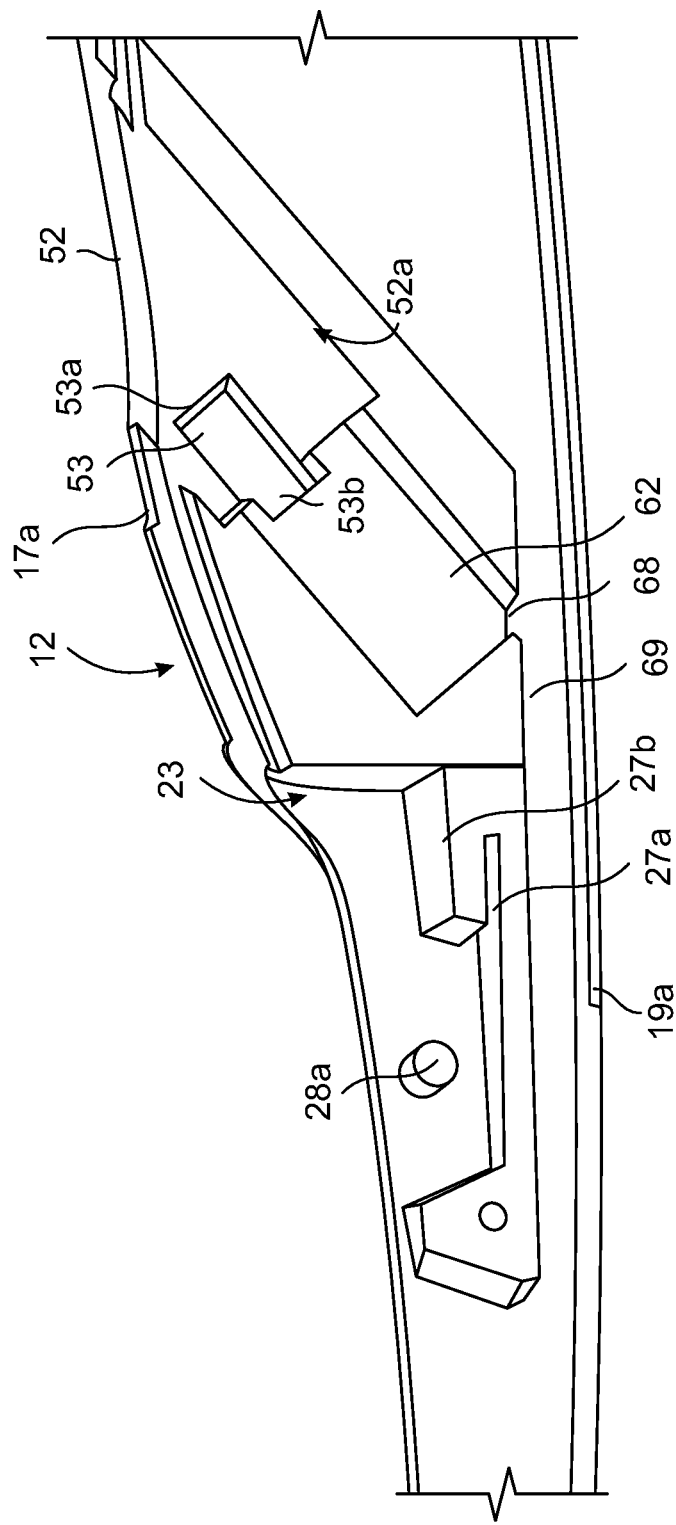
FIG. 15 is a partial inside view of the right side half of the housing of the embodiment of FIG. 1.
Figure 16:
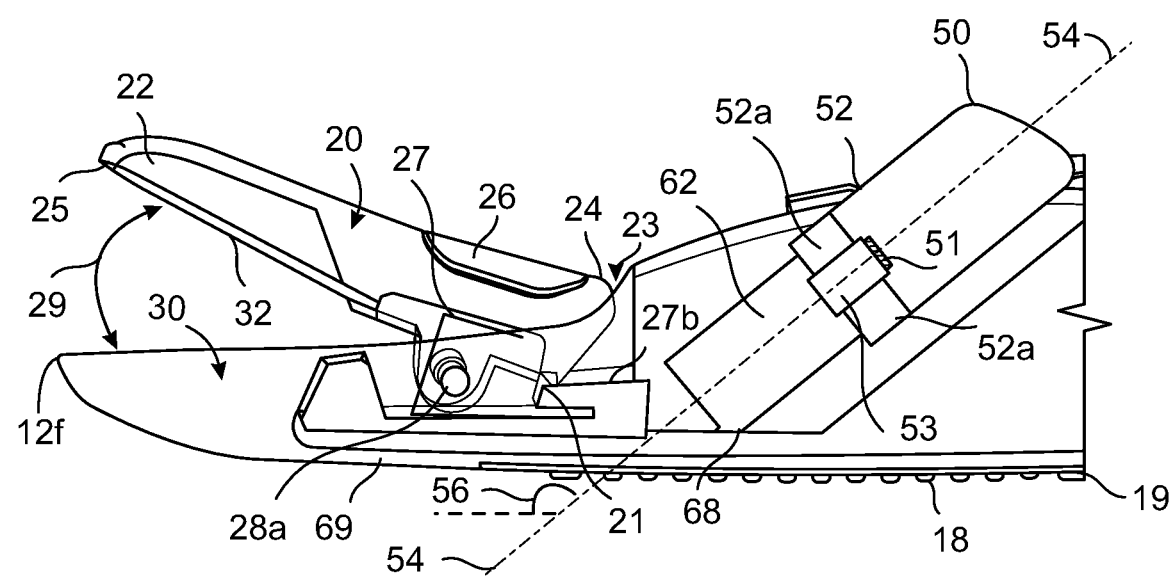
FIG. 16 is a partial cross-sectional view of the left front half of the embodiment of FIG. 1 showing the hatch in its open position.
Figure 17:
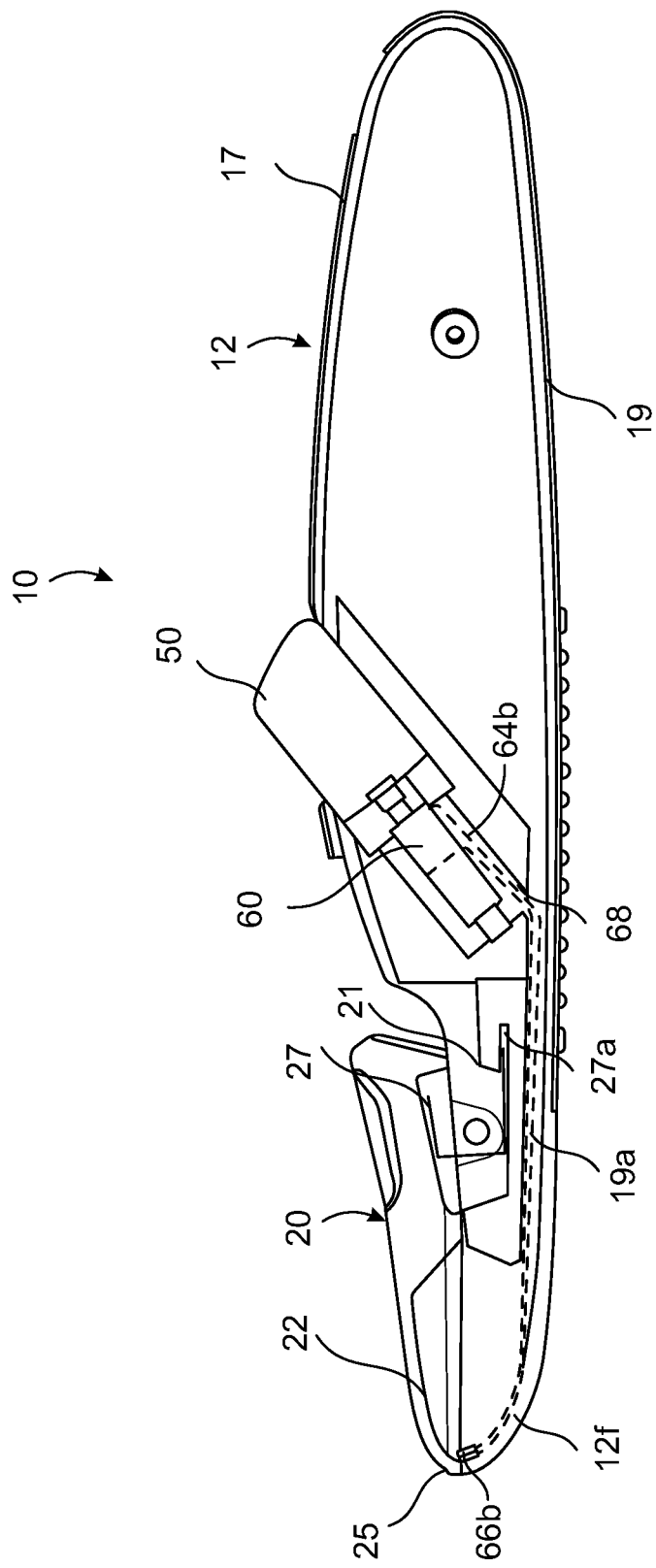
FIG. 17 is a partial longitudinal cross section of the device of FIG. 3.
Figure 18:
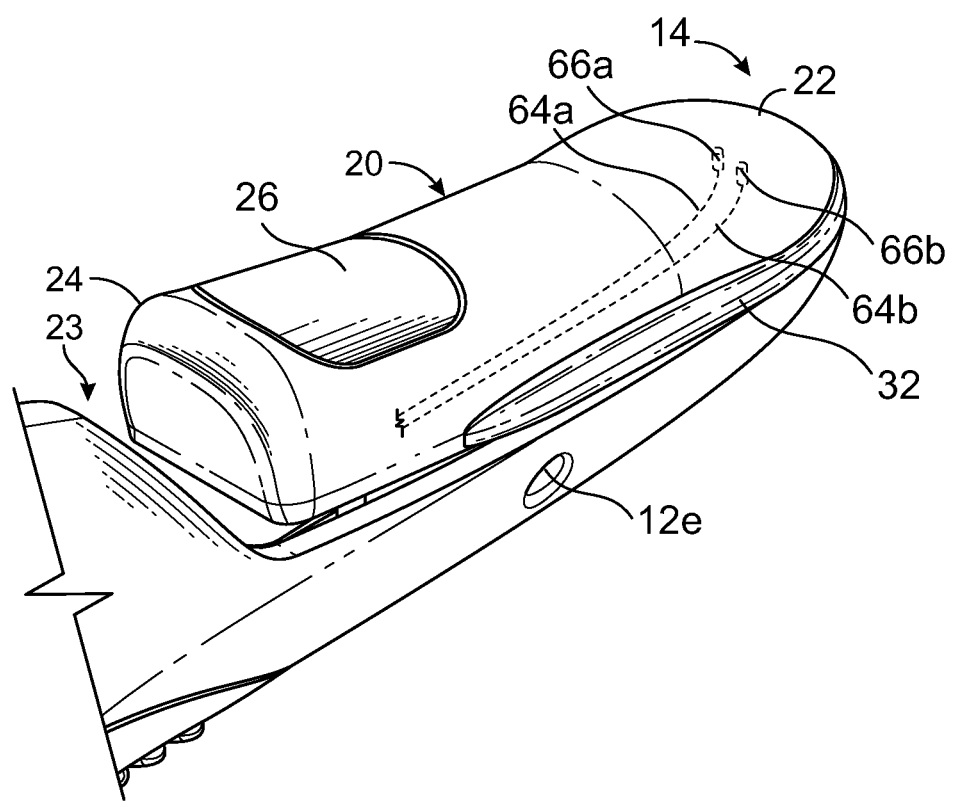
FIG. 18 is an enlarged view of the hatch end of the device of FIG. 1.

Referring to FIGS. 1-18, there is displayed one embodiment of the present disclosure providing an insect (e.g., tick) removal device 10. This device generally comprises an external housing (e.g., tubular body) 12 having a front proximal end 14 and a rear distal end 16 disposed along a longitudinal axis 15. The device 10 also comprises an openable and closeable hatch or lid 20 at its top front end, and a trigger button 50 located at its top midsection. The trigger button 50 activates an electrical charge directed to opposed electrodes 66a, 66b contained in the chamber area 30 (also referred to as encapsulation zone 30) underneath the hatch 20.

As will generally be seen, the housing 12 of the device 10 has a relatively tubular shape (here, somewhat cigar shaped), but other shapes can be employed. The housing 12 generally comprises a top side 12a, underside 12b, left side 12c, and right side 12d. In one embodiment, the housing comprises two opposed shell halves (right side and left side) that can then be attached together, by, for example, the use of two screws 12e, or gluing. In one embodiment, the interface between housing right side half and left side half is an overlapping lip interface where one housing half employs a circumferential edge having a recessed flange-like lip and the opposed housing half employs an outwardly extending circumferential lip that mates with the opposed half to create a smooth, tight connection between the housing halves.

The housing 12 is suitably sized, preferably to be held and operated in one hand. In one embodiment, the exterior of the housing 12 employs sections of gripping material or the other gripping surfaces. Housing 12 could have its halves made by injection molding of ABS plastic. Rubber or other suitable materials, such as thermoplastics, thermoplastic vulconates (TVPs), such as the Santoprene™ brand, and the like could be used as an overmold material to enhance the gripping surfaces of the device 10. In one embodiment, gripping surfaces or overmolded sections are provided on the top of the device in upper inlay area 17, on the underside/sides of the device in lower inlay area 19, and on the hatch button upper inlay area 26. In one embodiment, overmold material can be placed directly on the exterior surface of the housing 12. In another embodiment, the overmold material can be placed within recesses inlays 17a, 19a in the housing outer surface. Additionally, ribs 18, bumps or other surface gripping features, and the like, could also be added for additional gripping. These ribs 18 and the like could be separate, incorporated in to the inlay, or be molded directly into the body 12. The hand held device embodiments 10c of FIGS. 25-31 do not employ any inlays or gripping material on the housing 112 or hatch 20c. The hand held device embodiments 10d of FIGS. 32-38 do not employ any inlays on the housing 212, but do so on the hatch 20d, and also employ a lower gripping section 18. Other variations are possible, including placing gripping material in different locations and in different shapes, as well as providing gripping ridges or bumps in different arrangements and locations on housing and/or on the hatch.

In one embodiment, the hatch 20 comprises a set of opposed pivot mounts 28 with apertures or axel openings 29. The hatch can then be pivotally mounted to the housing via axels 28a. Other suitable pivot mounting mechanisms could be employed. In this embodiment, the hatch is spring loaded with a hatch spring 27 or the like to provide spring action in the pivotal opening and closing of the hatch 20. The spring 27 can be secured in place in known fashion, e.g., by securing it to the hatch spring mount 27a. It will be understood that other spring arrangements can be employed, such as a custom made spring or other integral spring designed to fit within the chamber 30, to provide the desired springe resistance sufficient to maintain the lid in a closed position unless the lid button 26 is pressed. In operation, the user can press down on button 26 located on the top of the hatch 20 near the back end 24 of the hatch 20. Pressing down on the hatch button 26 causes the hatch 20 to open much like an alligator's mouth (to form opening 29) until the lower edge 21 of the hatch contacts the hatch stop or ledge 27b. A gap or clearance space 23 permits the back end of the hatch to travel downwardly without interference. The front end of the hatch 20 forms a hatch jaw interface or bite 25 where the hatch 20 meets the housing 12. A small notch 25a or opening (seen in later embodiments, e.g., FIGS. 51, 53, 60, 63, 64. 69) may be provided in the front end of the hatch 20 to permit the surrounding of the tick's head. A lip 32 extends around a part of the front perimeter of the hatch. The hatch 20 may also be outfitted with an underside lip 21 to interface with the receiving chamber 30 and provide a secure closure. In operation, a person using this device can hold the device with one hand, and for example, open and close the hatch by pressing down with a thumb on the button 26.

Figure 19:
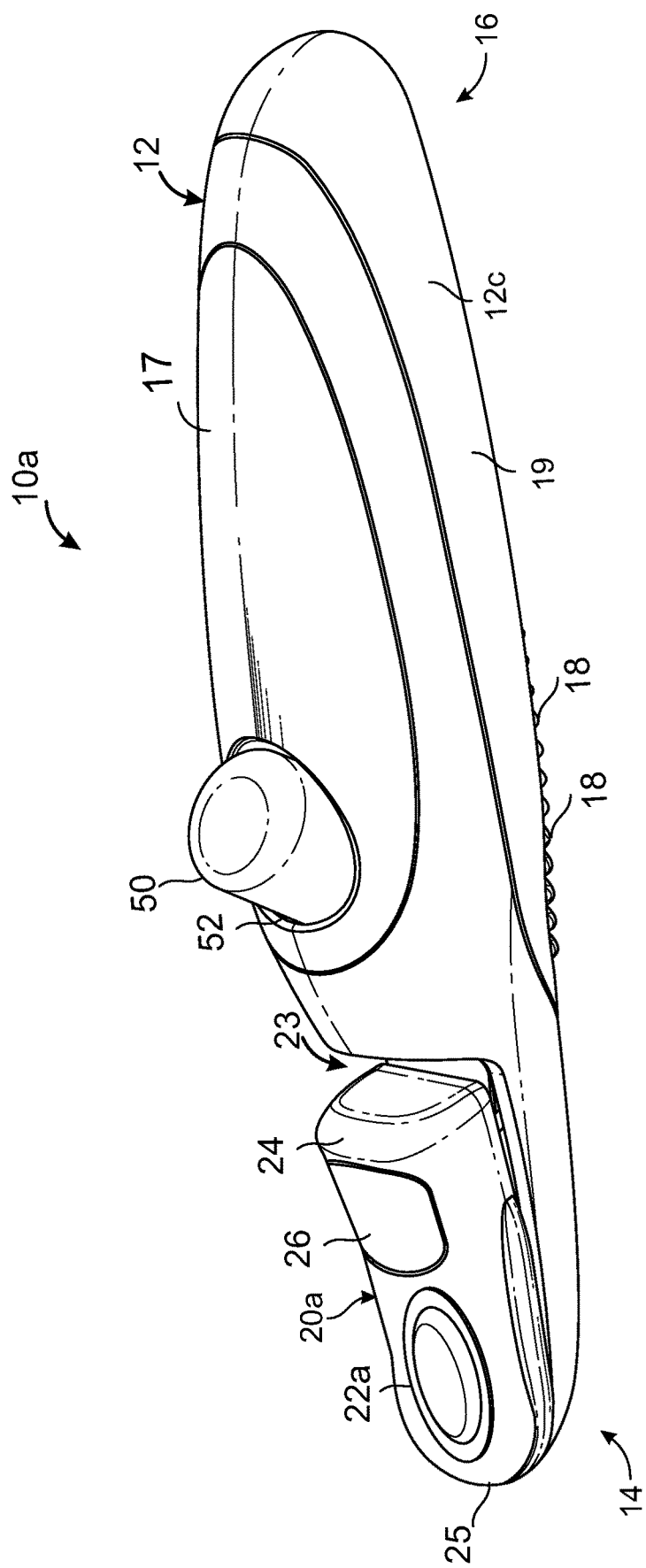
FIG. 19 is a rear, left side perspective view of another hand operated reaching device for removing ticks from animals or humans according to another embodiment of the present disclosure similar to that of FIG. 1, but employing a different hatch.
Figure 20:
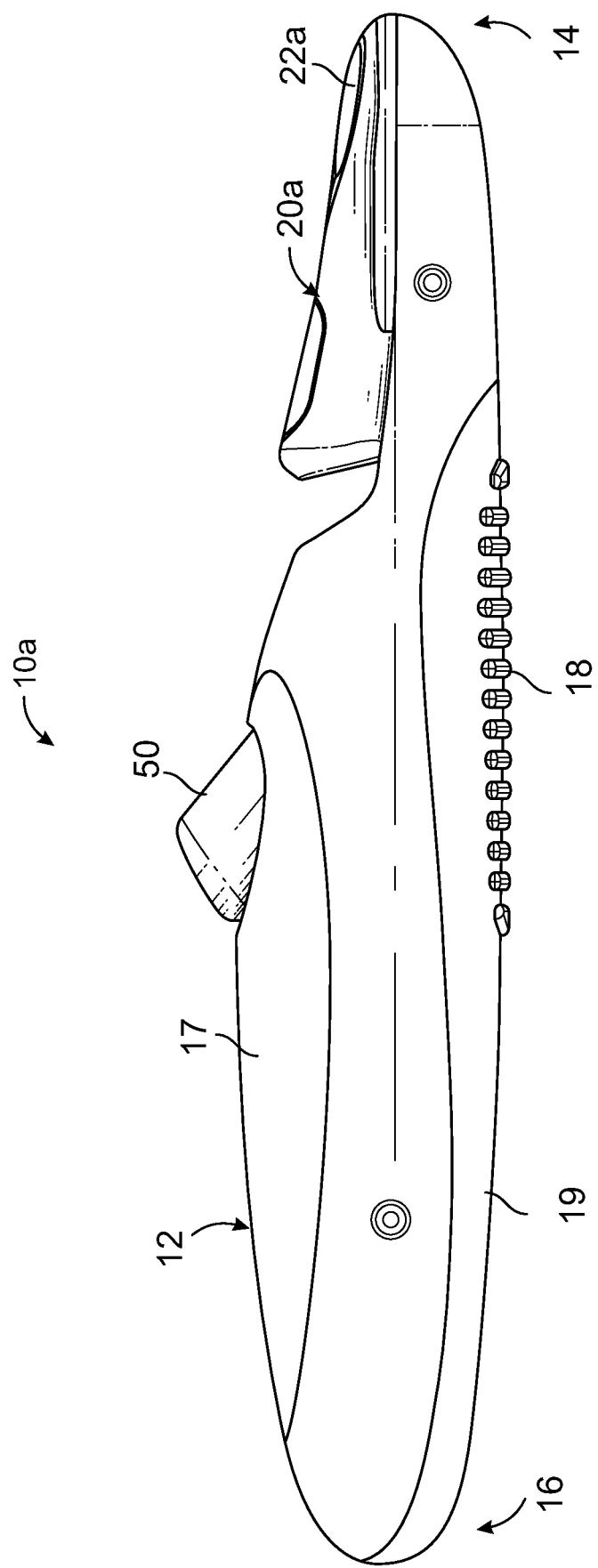
FIG. 20 is a right side plan view of the embodiment of FIG. 19.
Figure 21:
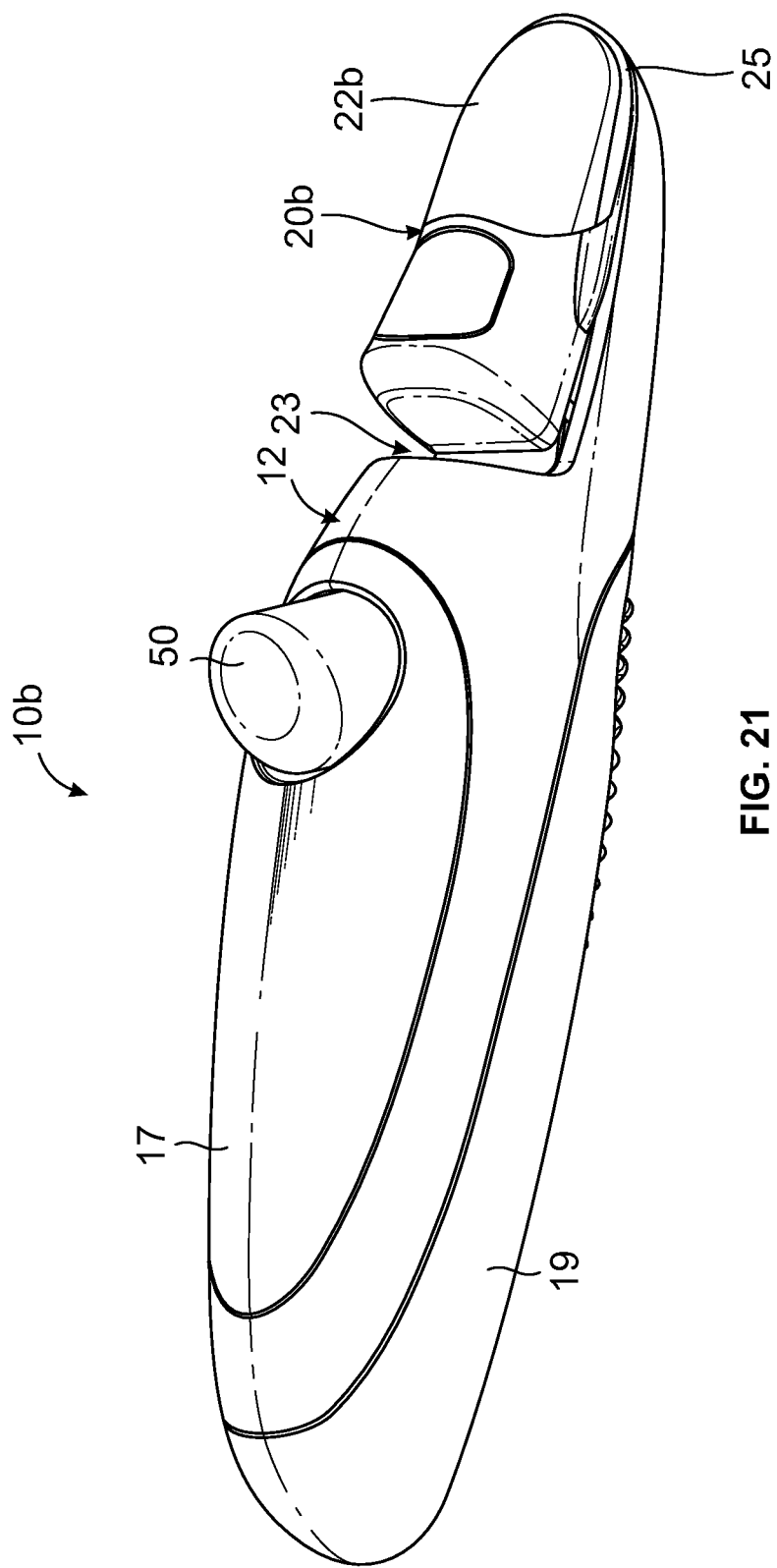
FIG. 21 is a front, right side perspective view of another hand operated reaching device for removing ticks from animals or humans according to another embodiment of the present disclosure similar to that of FIG. 1, but employing a different hatch.
Figure 22:
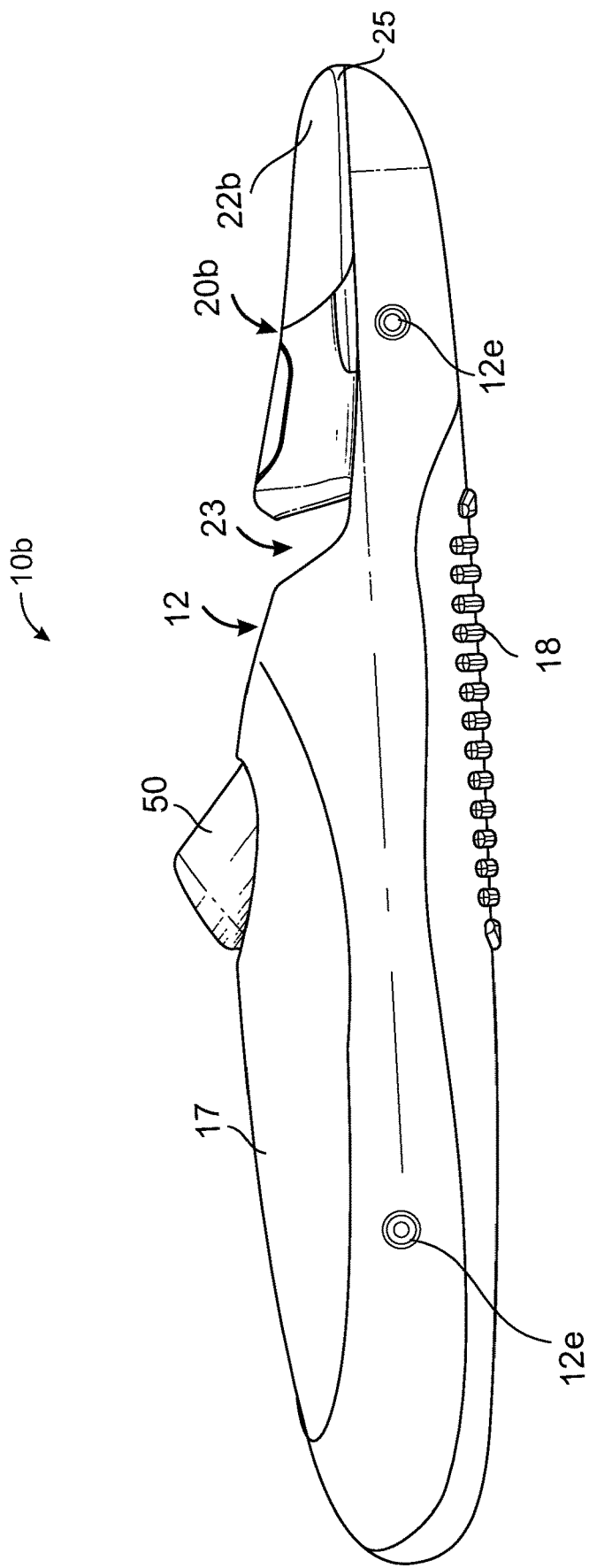
FIG. 22 is a right side plan view of the embodiment of FIG. 21.
Figure 23:
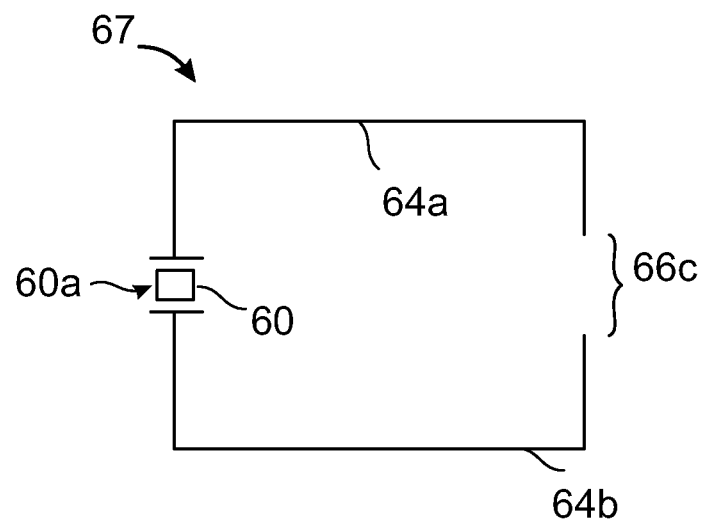
FIG. 23 depicts an exemplary circuit diagram for operation of a piezoelectric crystal used in a tick removal device according to an embodiment of the present disclosure.

The front portion 22 of the hatch 20 is preferably clear and transparent so that the user can see into the chamber 30. However, the hatch can be opaque or non-transparent if desired. In one embodiment of the hatch depicted in FIG. 14, the front of the hatch 22a comprises a transparent plastic magnifying lens or zone of magnification to better view the tick 1. The transparent zone of magnification 22a can take many forms, such as being integrated into the entirety of the hatch 20, as generally shown at 22a in FIG. 14, or by being a more localized spherical zone of magnification in hatch 20a as depicted at 22a in FIGS. 19-20 (illustrating hand held device 10a), or as a portion of the hatch 20b as depicted at 22b in FIGS. 21-22 (depicting hand held device 10b).

Beneath the hatch 20 is a hatch receiving chamber 30. Contained within the chamber 30 are two opposed electrode tips 66a, 66b spaced apart from each other by electrode gap 66c. The two electrode tips 66a and 66b are mounted so that they are proximate the front edge of the device 12f and slightly spaced apart by gap 66c. The electrode tips 66a and 66b are connected, via insulated wire 64a, 64b, to a piezoelectric device 60 mounted within the housing 12 in a manner that permits the trigger button 50 to be used to activate the piezoelectric device and send a voltage across the electrode tips.

The piezoelectric device 60 uses a piezo-ceramic element (not shown) contained within a piezoelectric device housing 60b, the piezo-ceramic element developing an electrical charge when mechanical pressure is applied to the piezoelectric strike point 60a of the piezo-ceramic element via a metal hammer (not shown) located within the piezoelectric device housing, the metal hammer being engaged via piezoelectric device hammer button 60c. This occurs because atoms in the crystal are physically displaced when the crystal is squeezed. The atoms include electrons protons and relative movement of these particles on average and en masse creates a separation of charge which develops a voltage across the terminals of the device. The generator 60 is powered by mechanical energy stored in a spring (not shown). As the user presses the trigger button 50 on the device 10, the trigger button 50 in turn engages the hammer activation button 60c and the spring is compressed. When the hammer button 60c has moved through a specific distance, approximately four millimeters, a plastic cam (not shown) releases the spring (not shown) and it drives a metal hammer (not shown) into the crystal (not shown). The combined spring force and hammer momentum compress the piezo electric crystal and a pulse of electricity is produced. The more rapidly the crystal is compressed, the higher the voltage developed. At the same time, the more rapidly the process occurs, the shorter the duration of the pulse. Due to these counteracting effects, the energy generated is approximately constant over a fairly wide range of hammer momentum.

The electrical pulse generated by the device 60 has two phases. The first begins when the hammer strikes the crystal and continues as the hammer further compresses the crystal. In this phase, the peak voltage reaches 13,000 volts but the total duration of the phase is only about 100 microseconds. As the hammer recoils and releases the pressure on the crystal, an opposite polarity voltage pulse is generated. This pulse peaks at –2,500 volts and decays exponentially, effectively dying away in 5 milliseconds. The total energy delivered by the generator was measured at 7 mill-Joule.

It should be noted that the hammer momentum is not a function of how slowly or quickly the user presses the button. It is determined by the length of the spring at the moment the cam releases it, which is fixed by the geometry of the mechanism. Pressing the button 50 with more force or more quickly (which are actually equivalent) will not measurably increase the electrical output.

The piezo-electric device can be obtained from many sources, such as, the model YQ620-65D/B1 piezo ignitor sold by Foshan Yiqiang Electronic Co., Ltd. This particular product produces an initial voltage of more than 13 KV, has a durability of 10,000 uses, and requires an operating force of less than 2.8 KG The trigger button 50 is tangentially mounted within housing 52a along a trigger button axis 54. In the embodiments shown, the trigger axis angle 56 (as taken from the proximal side of the trigger relative to the horizontal axis 15) is approximately 135° off the horizontal axis. This angle 56 facilitates pushing of the trigger button forward and downward while being able to maintain a steady hold on the device 10. Other angles 56 are likewise suitable to provide optimal ergonomic orientation of the user's thumb to press the button while holding the device in the same hand. For example, the angle 56 could range from about 90° to about 160°, but preferably is between about 120° to about 150°. The trigger is contained within a housing 52a and is capable of back and forth movement along the axis 54. In one embodiment, the trigger button 54 is outfitted with opposed ears or tabs 51 that extend outwardly and ride up and down within slots or channels 53 in the inside of the housing 12. The slots are provided with upper and lower stops 53a, 53b to contain the movement of the trigger button 50 along the axis 54. The trigger button slots define an aperture opening 52 to permit the trigger button to extend through the housing 12.

The tick removal device 10 also comprises a piezoelectric device 60 (such as those employing a rod-shaped single-layer piezoelectric ceramic) capable of generating high voltage upon receipt of an applied mechanical stress from a striker (not shown). The piezoelectric device 60 (striker and crystal) may be similar in nature to the piezoelectric ignitors used in cigarette lighters and gas grill lighters. The piezo electric device 60 is located within the interior 62 of the housing 12. The user activates the spring-loaded hammer or striker of the piezoelectric device 60 by pushing down on the trigger button 50. As will be understood, the trigger button 50 is mounted within housing 12 and interfaces with the triggering device of the piezoelectric device 60 such that when the user pushes down the trigger button 50, the trigger button 50 will in turn push down the piezoelectric device 60 hammer activation button 60c. Electrode wires 64a and 64b extend from the piezo electric device 60, through outlet 68, then through wiring corridor/path 69 to the front of the device where the electrode tips 66a, 66b are mounted within the chamber 30 in spaced relationship.

The trigger button 50 will cause the crystal of the piezoelectric device 60 to be struck at its strike point 60a, generating a voltage (V) due to the compression of the piezoelectric crystal in the piezoelectric device 60. The circuit 67 powered by the piezoelectric crystal device 60 contains a spark gap 66c. The voltage (V) created by the striking of the piezoelectric crystal 60 will generate electrical arcing (not shown) across the spark gap 66c.

In order to operate the device the user pushes down the hatch button 26 to open the hatch 20. The hatch mouth opening 29 is then placed over the tick 1 on the skin of the animal or person so that the tick is generally oriented between the opposed electrode tips 66a, 66b. Once the hatch opening 19 is placed around the tick, e.g., by moving the stationary lip portion 12f of the housing 12 front end proximate the tick's body and the host's skin, the thumb is then slowly released to close the hatch 20, and the trigger button 50 is then pushed allowing the striker in the piezoelectric device 60 to hit the piezoelectric crystal initiation point 60a which creates a high voltage charge that travels down the electrode wiring 64a, 64b and arcs across the spark gap 66c thereby electrocuting the tick. The tick 1 then removes itself from the skin where it then falls into the enclosed chamber 30. The user can then dispose of the tick 1 by again opening the hatch 20 and disposing of the tick in a desire disposal location.

Figure 24:
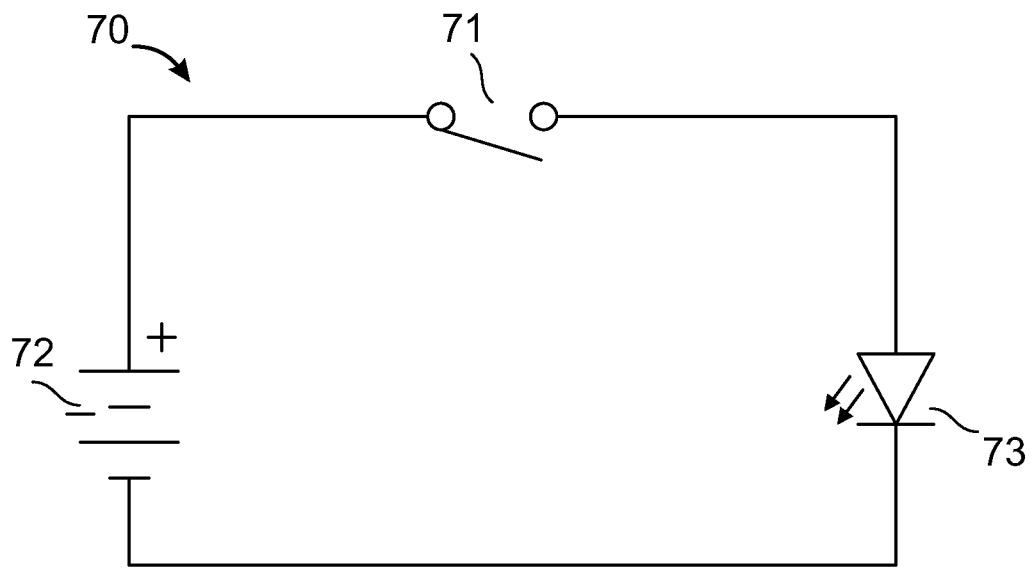
FIG. 24 depicts an exemplary secondary circuit diagram for operation of a tick removal device according to an embodiment of the present disclosure.
Figure 25:
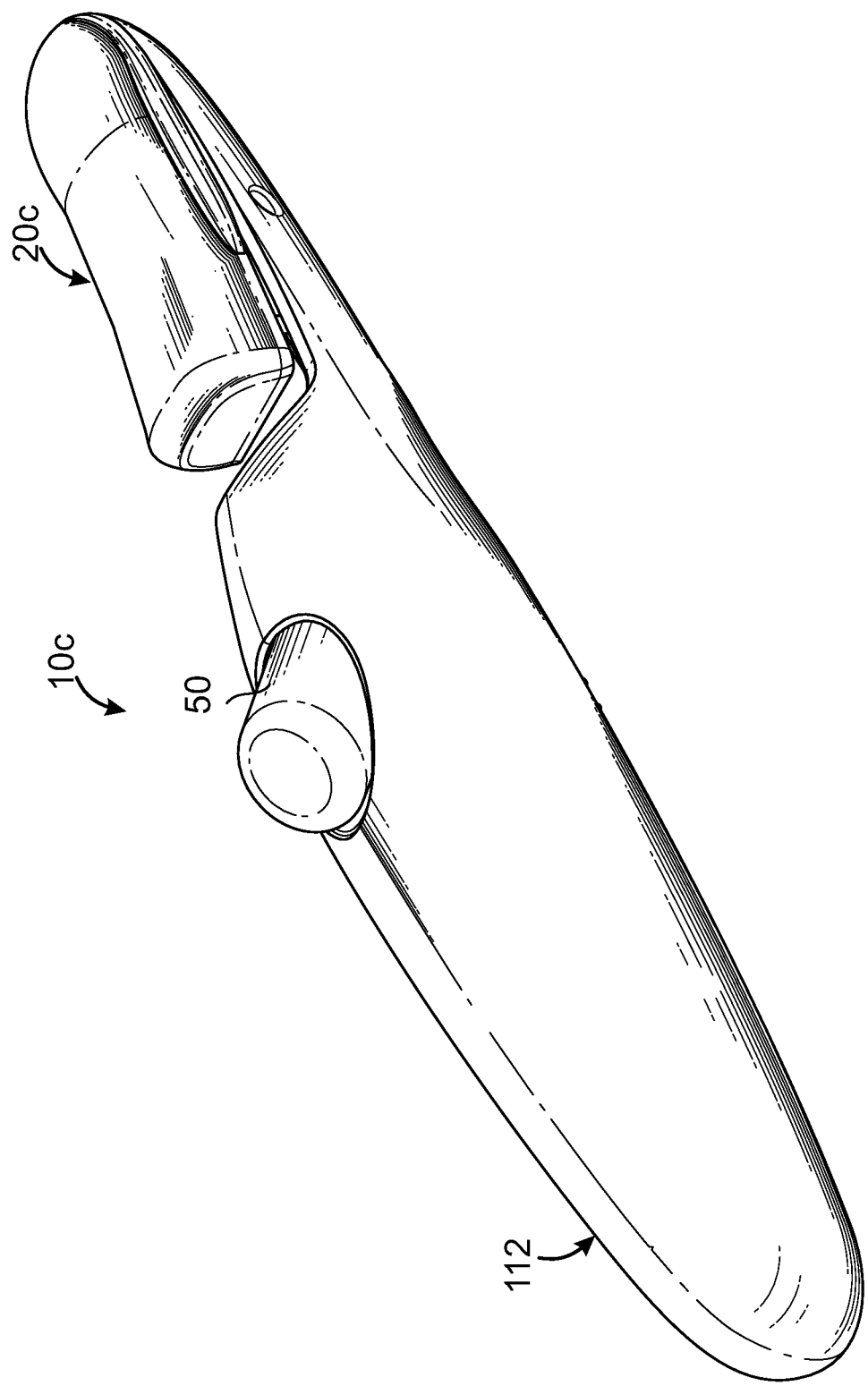
FIG. 25 is a rear, right side perspective view of another hand operated reaching device for removing ticks from animals or humans according to one embodiment of the present disclosure.
Figure 26:
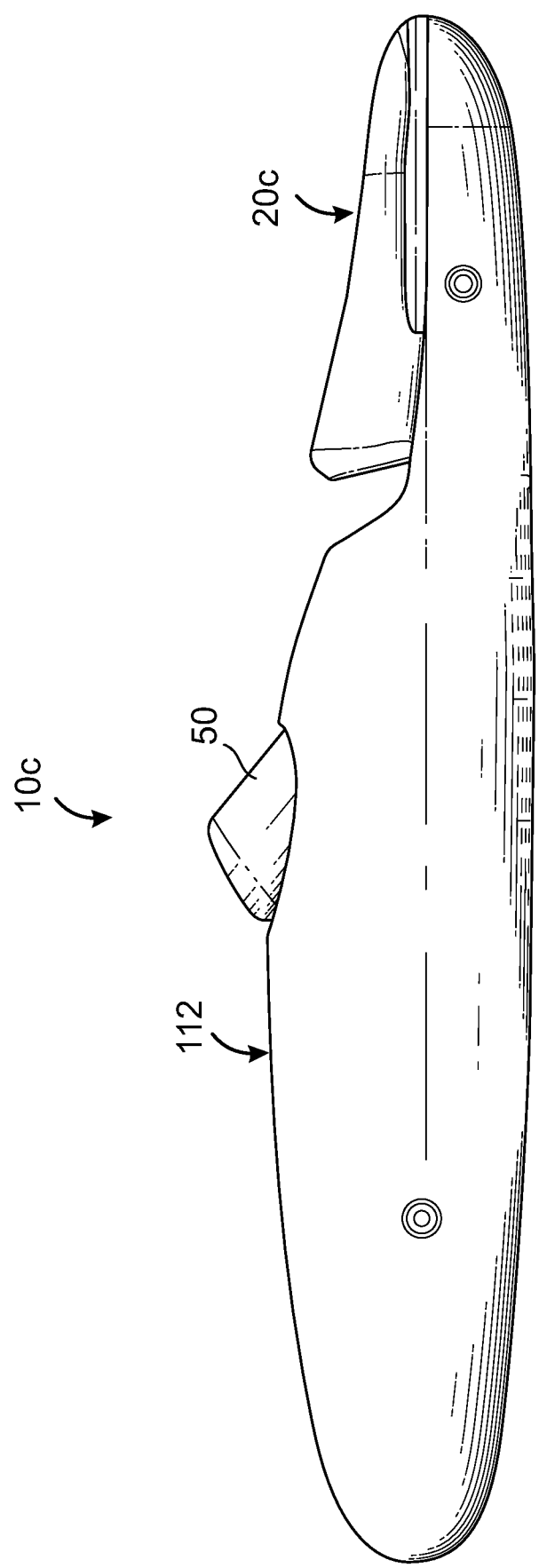
FIG. 26 is a right side plan view of the embodiment of FIG. 25.
Figure 27:
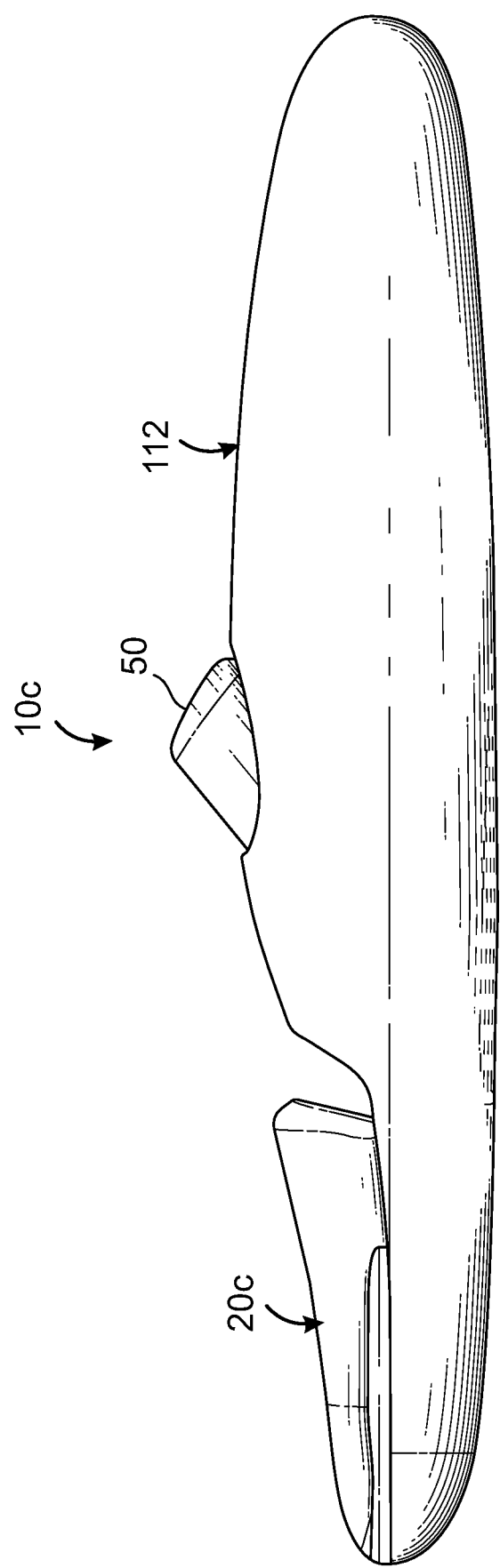
FIG. 27 is a left side plan view of the embodiment of FIG. 25.
Figure 28:
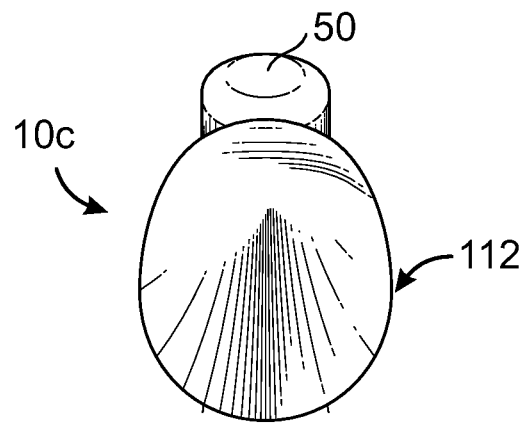
FIG. 28 is a rear end plan view of the embodiment of FIG. 25.
Figure 29:
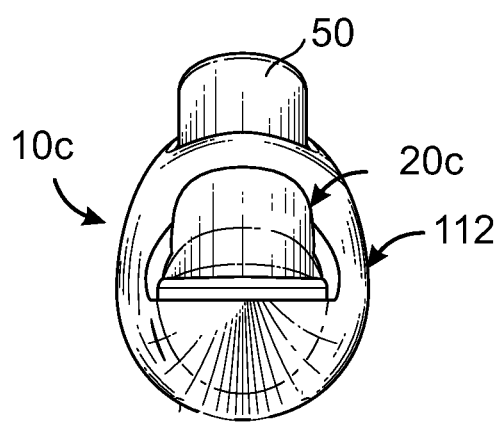
FIG. 29 is a front end plan view of the embodiment of FIG. 25.
Figure 30:
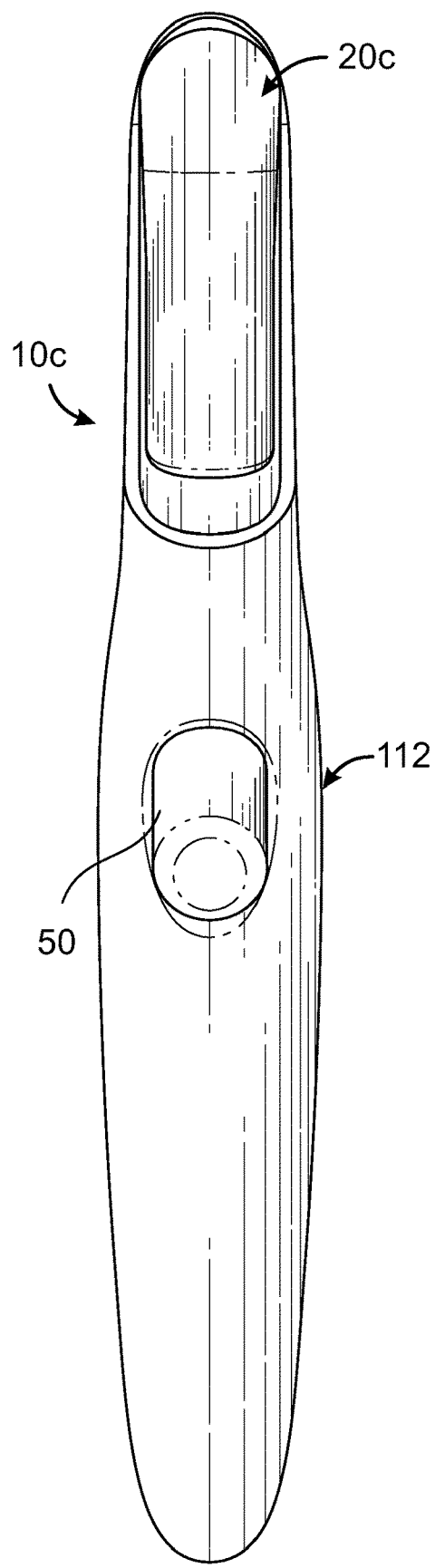
FIG. 30 is a top plan view of the embodiment of FIG. 25.
Figure 31:
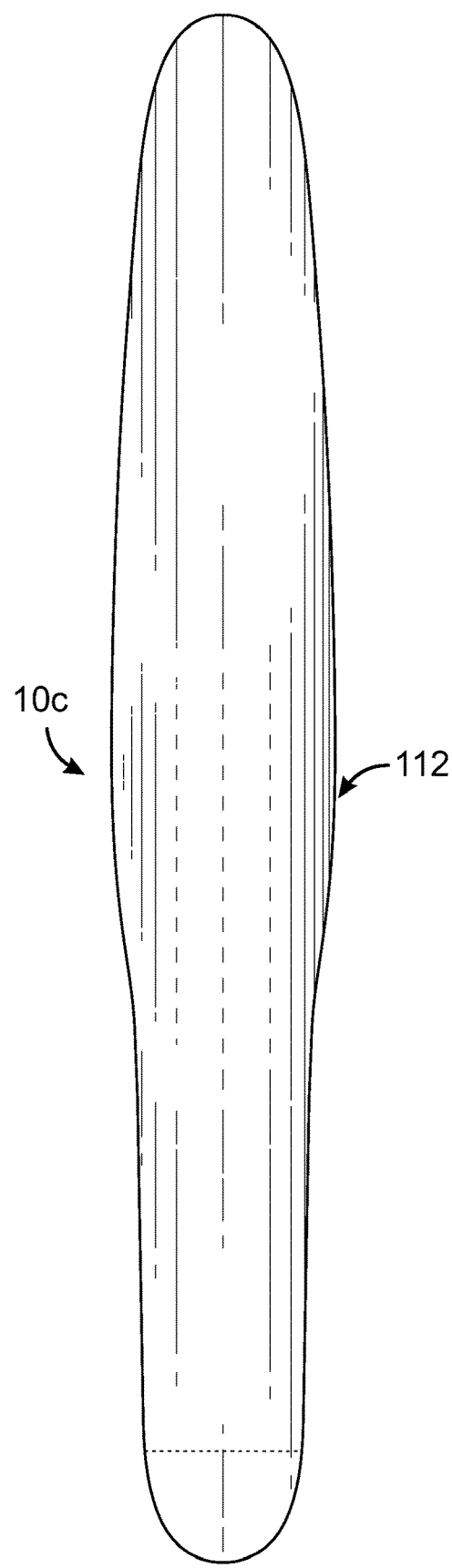
FIG. 31 is a bottom plan view of the embodiment of FIG. 25.
Figure 32:
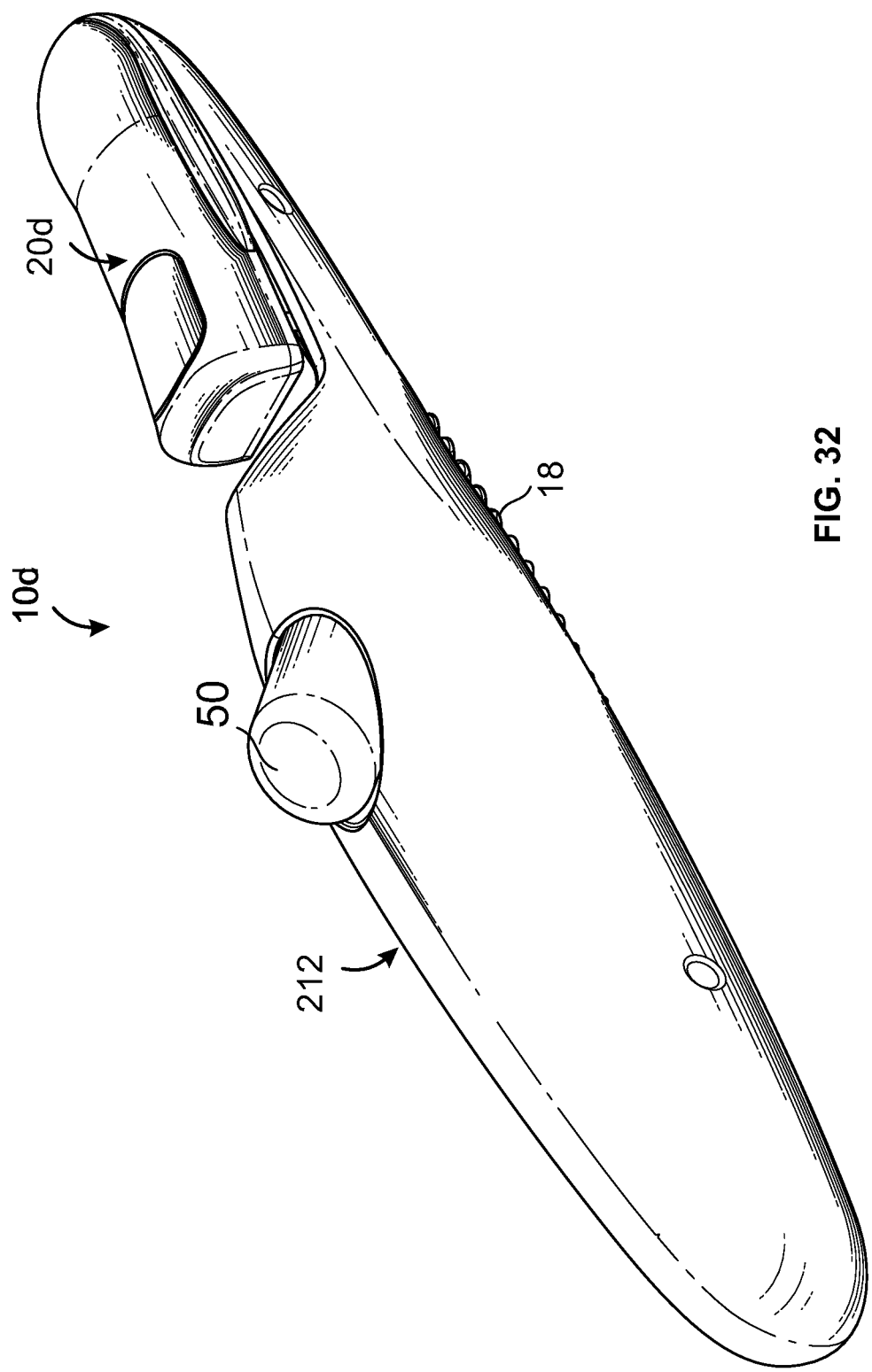
FIG. 32 is a rear, right side perspective view of another hand operated reaching device for removing ticks from animals or humans according to one embodiment of the present disclosure.
Figure 33:
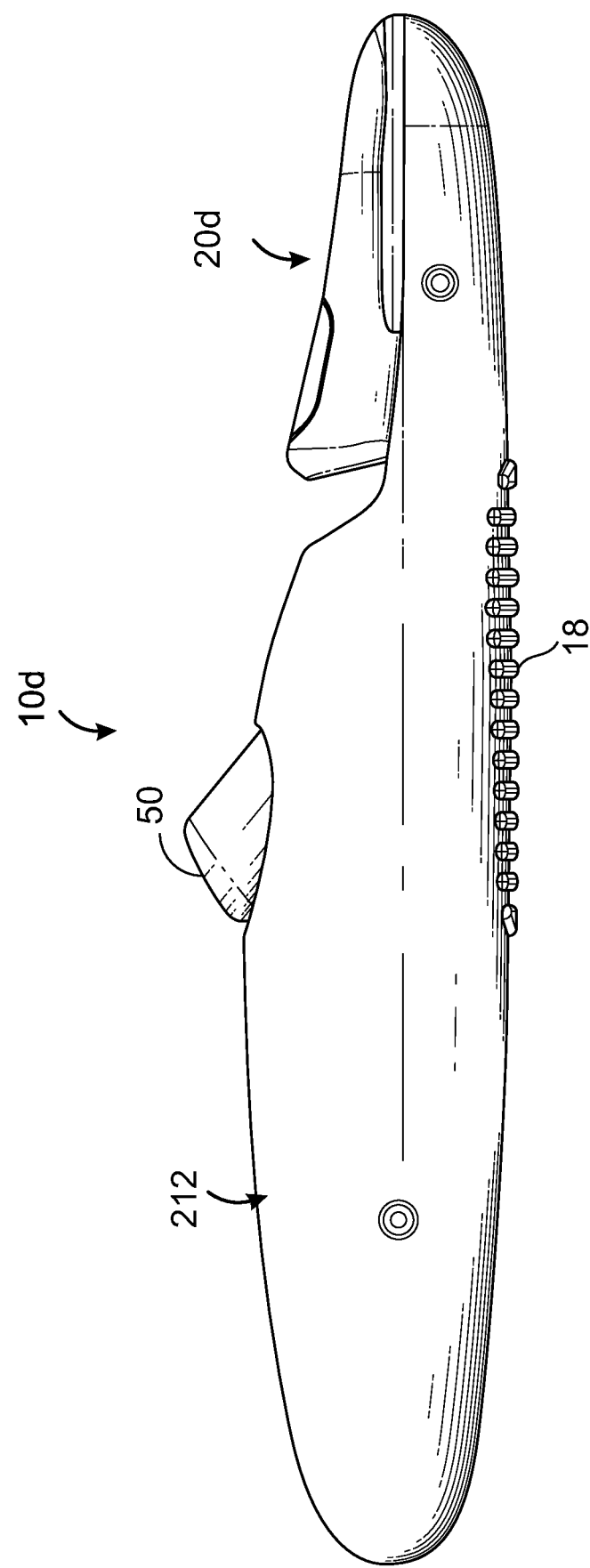
FIG. 33 is a right side plan view of the embodiment of FIG. 32.
Figure 34:
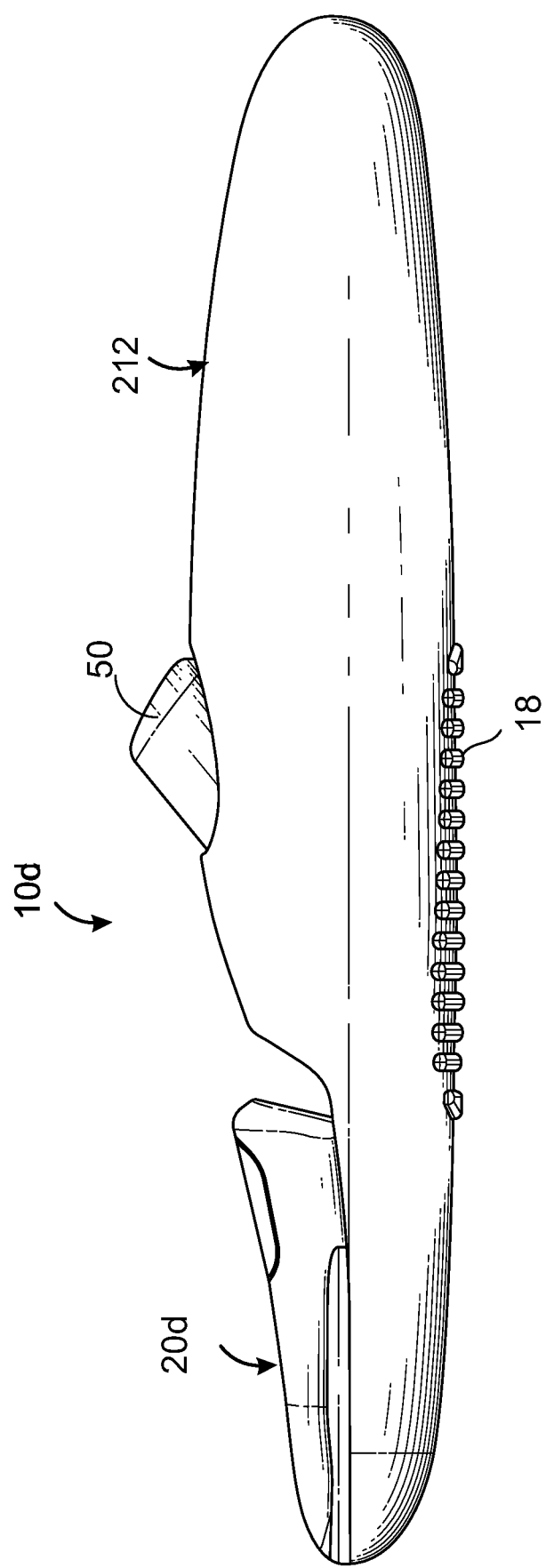
FIG. 34 is a left side plan view of the embodiment of FIG. 32.
Figure 35:
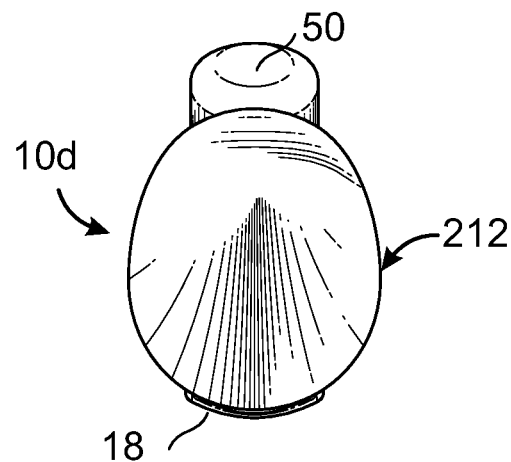
FIG. 35 is a rear end plan view of the embodiment of FIG. 32.
Figure 36:
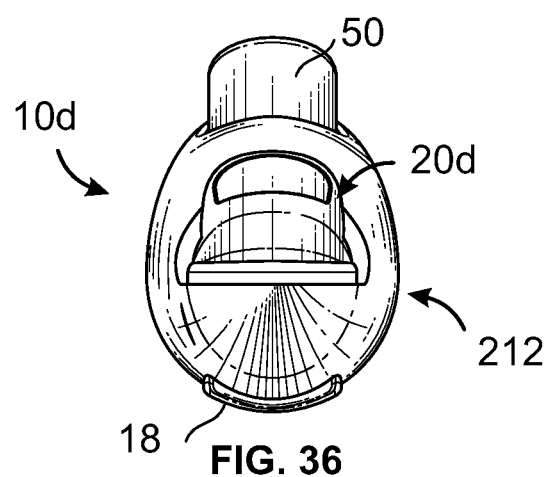
FIG. 36 is a front end plan view of the embodiment of FIG. 32.
Figure 37:
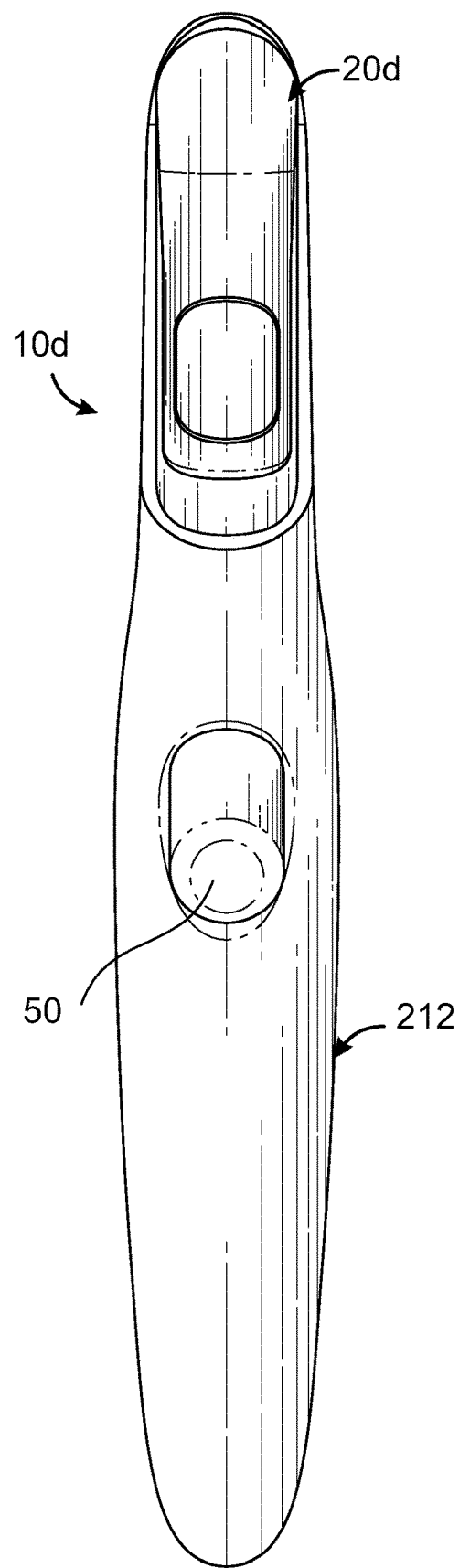
FIG. 37 is a top plan view of the embodiment of FIG. 32.
Figure 38:
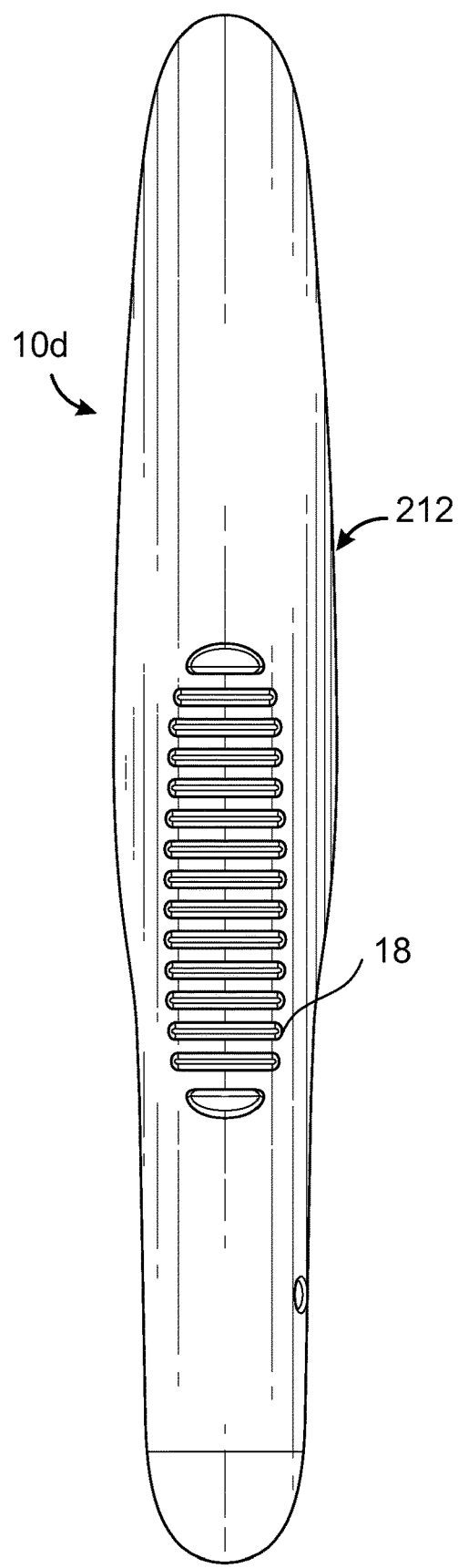
FIG. 38 is a bottom plan view of the embodiment of FIG. 32.
Figure 39:
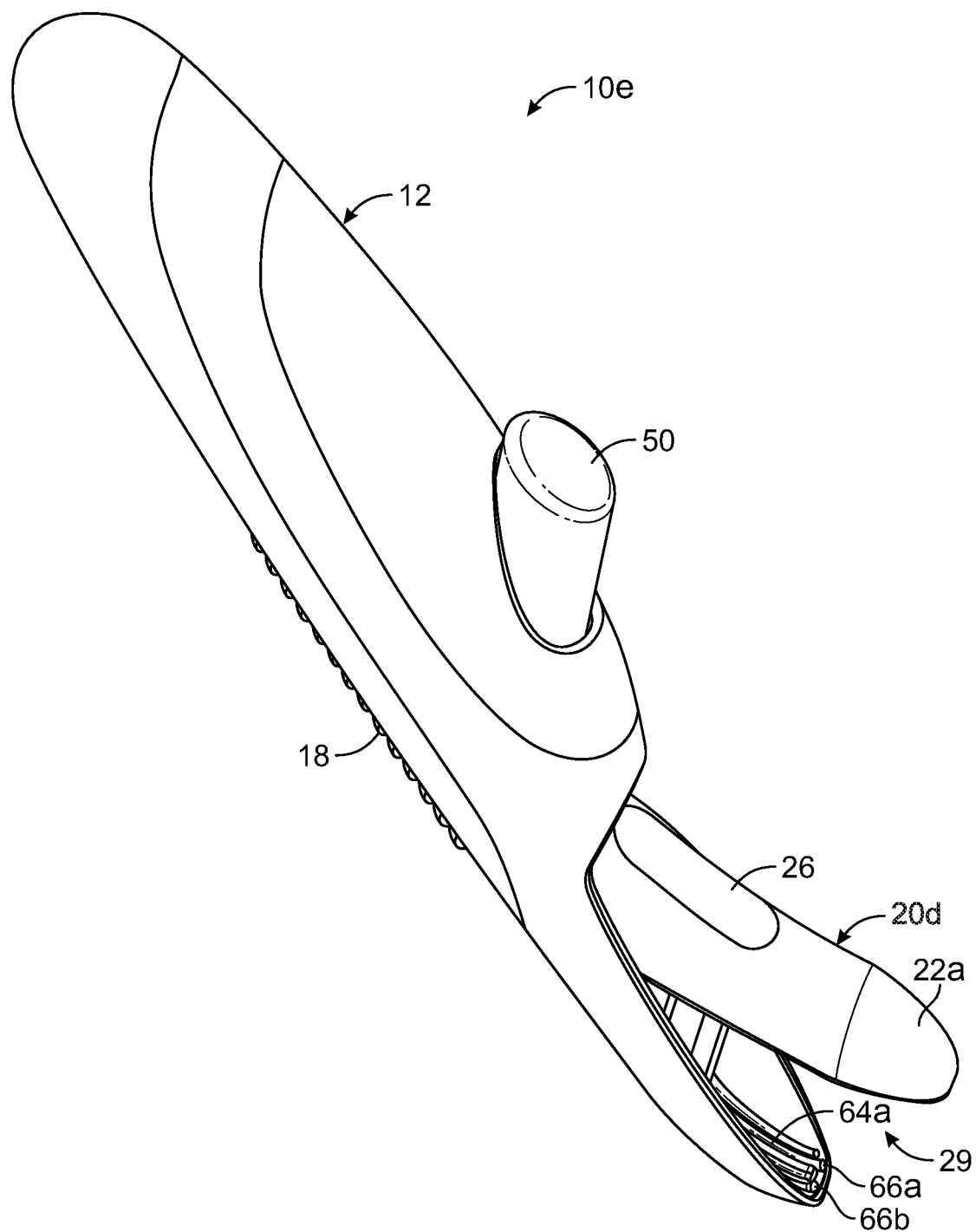
FIG. 39 is a rear, right side perspective view of a hand operated reaching device for removing ticks from animals or humans according to another embodiment of the present disclosure shown with the hatch or lid in the open position.
Figure 40:
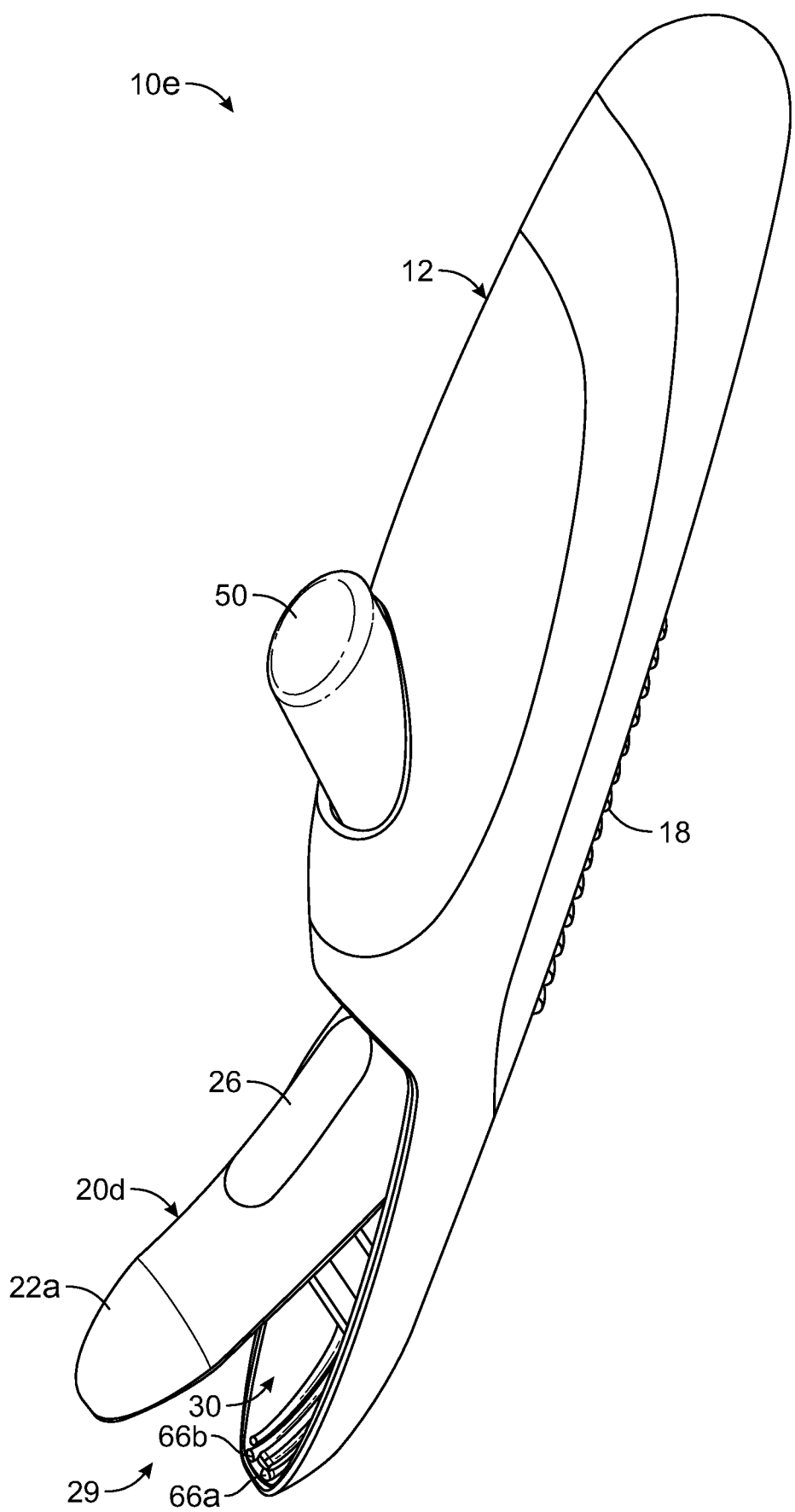
FIG. 40 is a rear, left side perspective view of the embodiment of FIG. 39.
Figure 41:
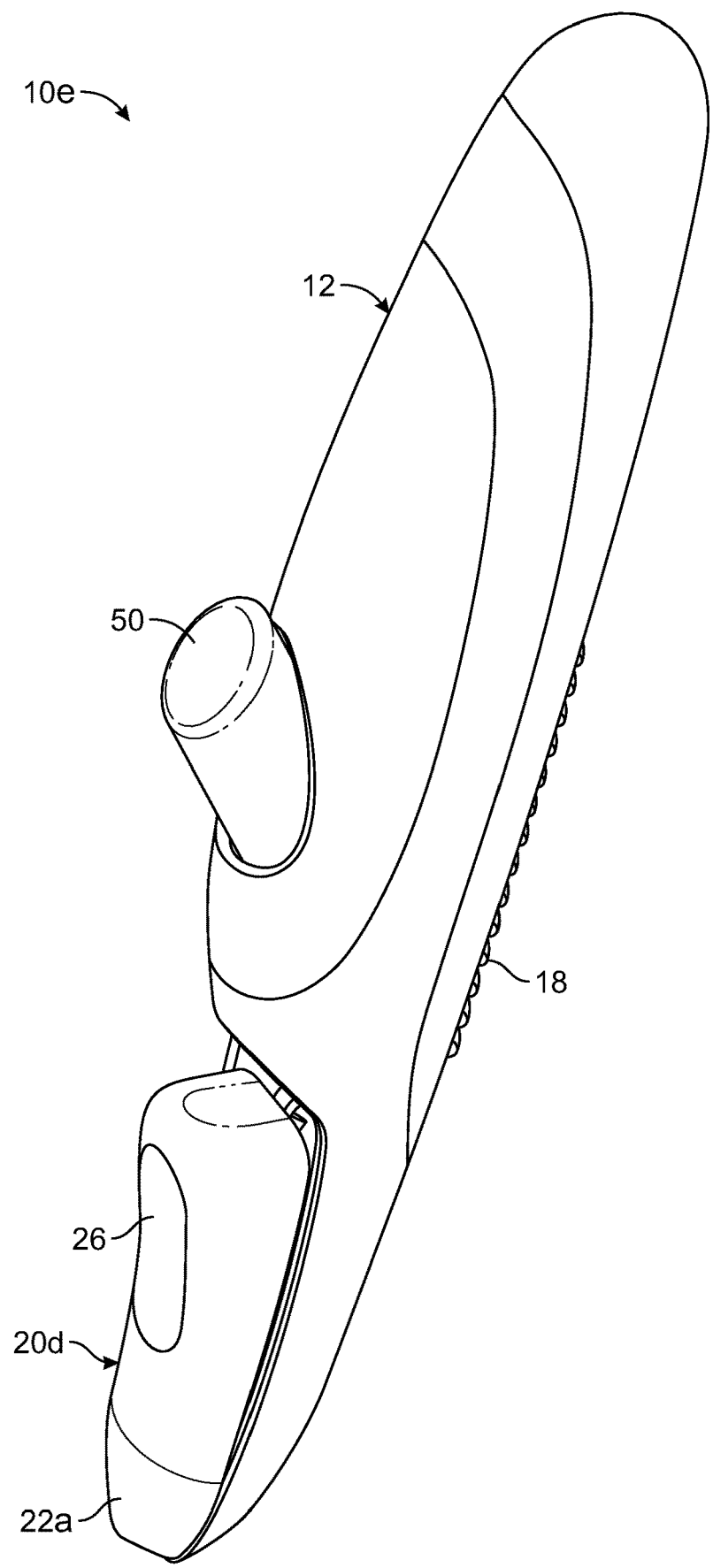
FIG. 41 illustrates the embodiment of FIG. 40 shown with the hatch or lid in the closed position.
Figure 42:
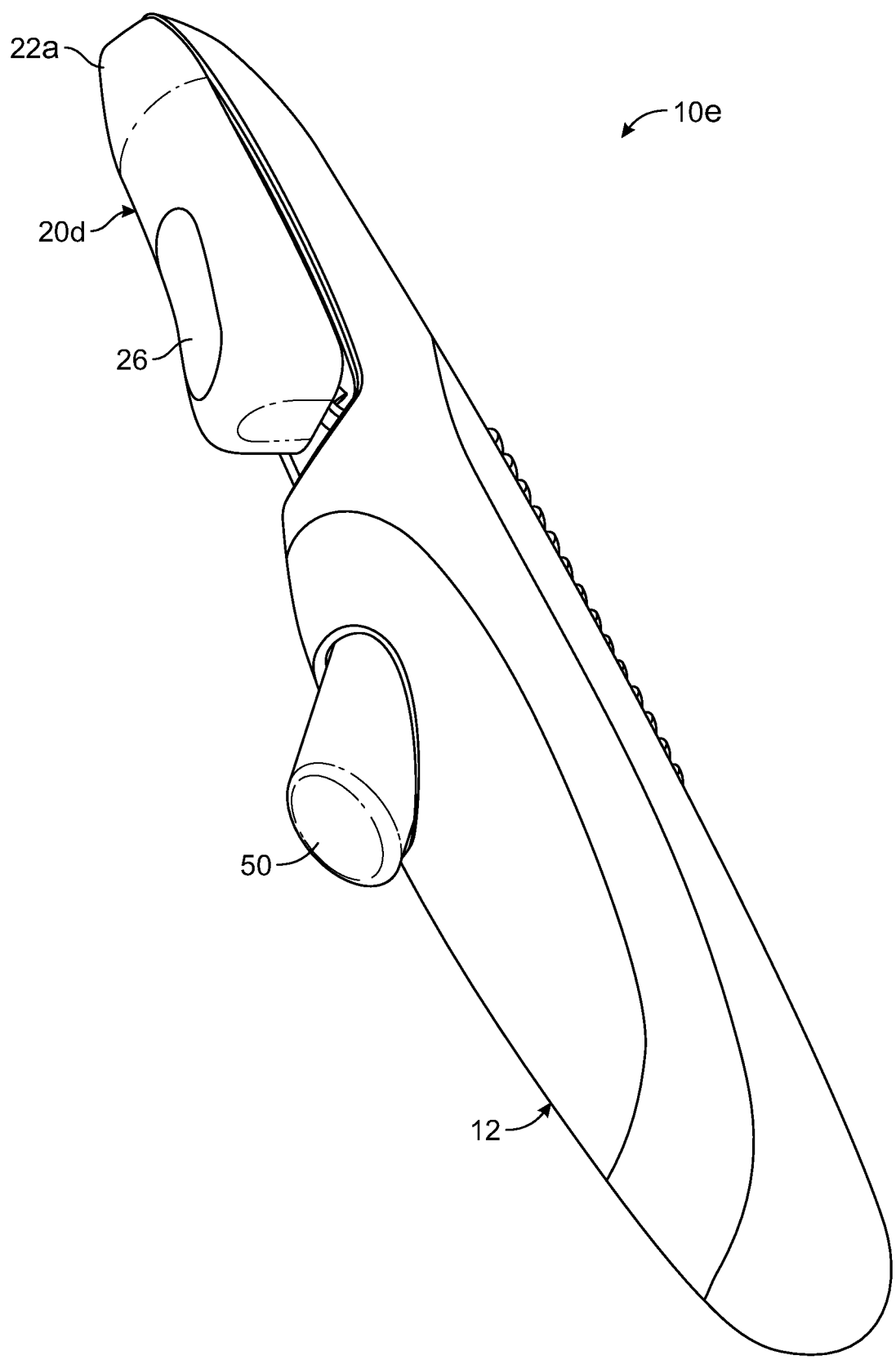
FIG. 42 is a rear, right side perspective view of the embodiment of FIG. 41.
Figure 43:
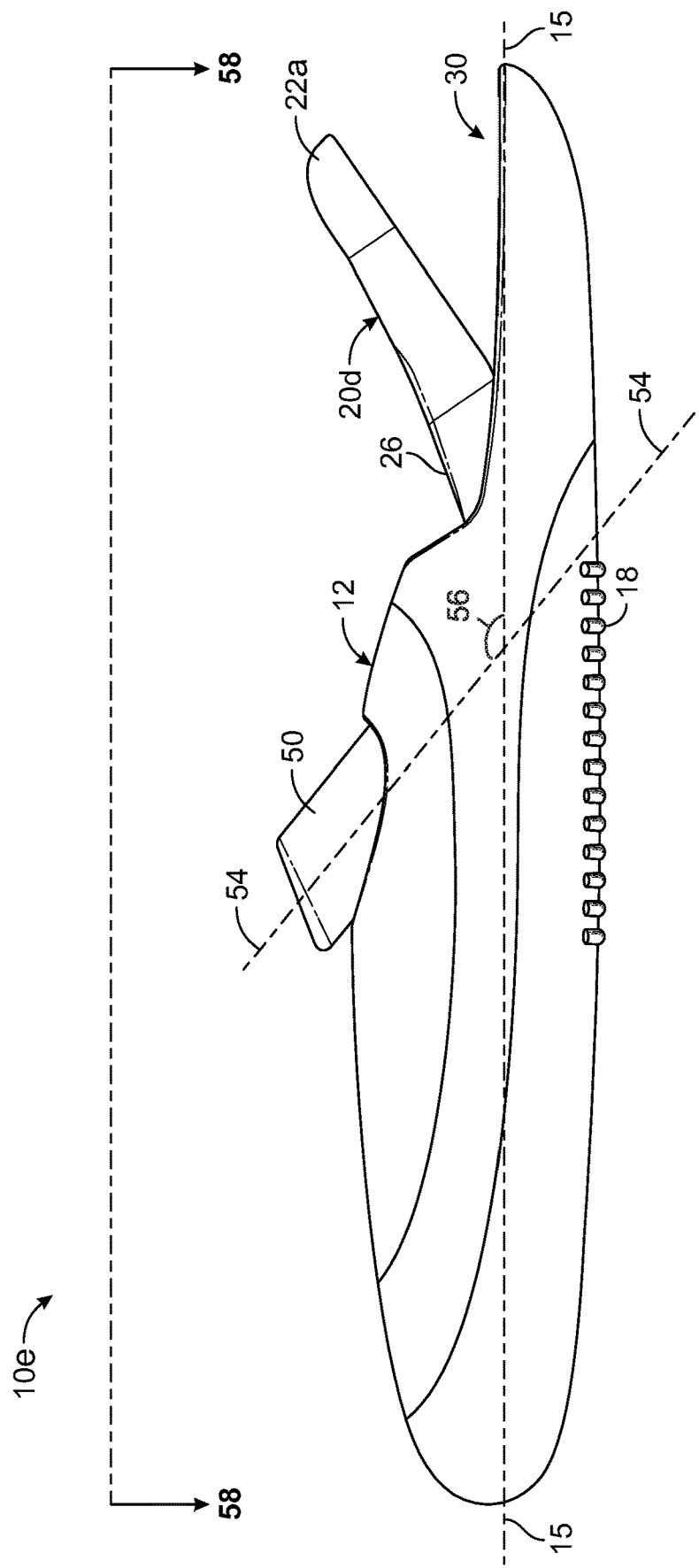
FIG. 43 is a right side plan view of the embodiment of FIG. 39 shown with the hatch or lid in the open position.
Figure 44:
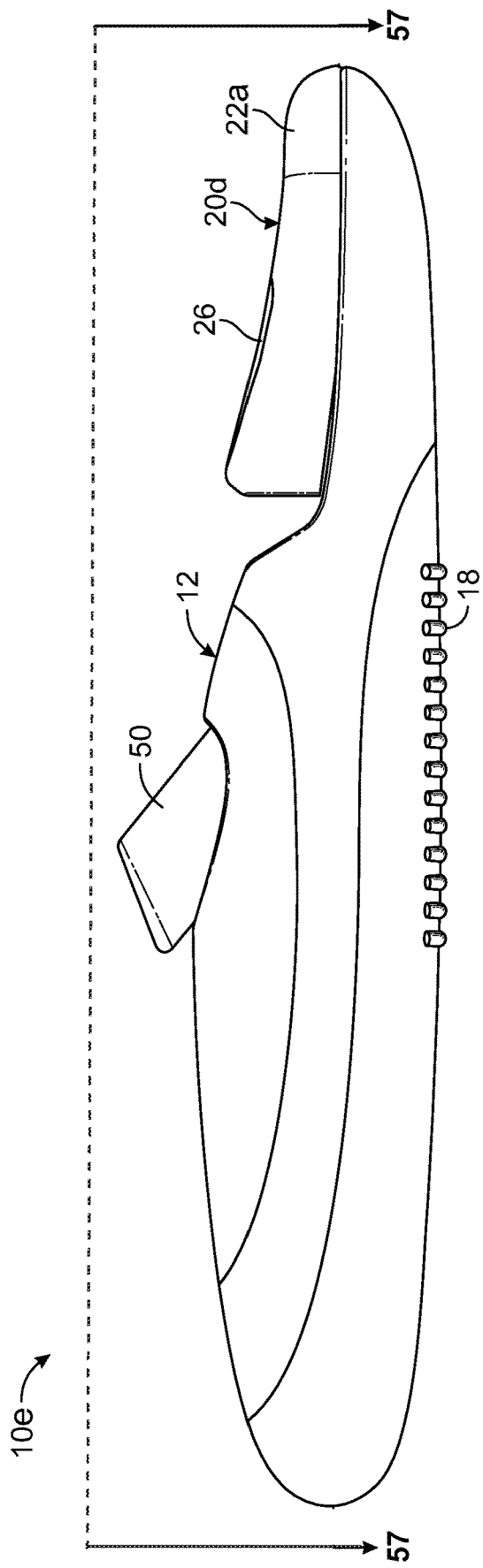
FIG. 44 is a right side plan view of the embodiment of FIG. 39 shown with the hatch or lid in the closed position.
Figure 45:
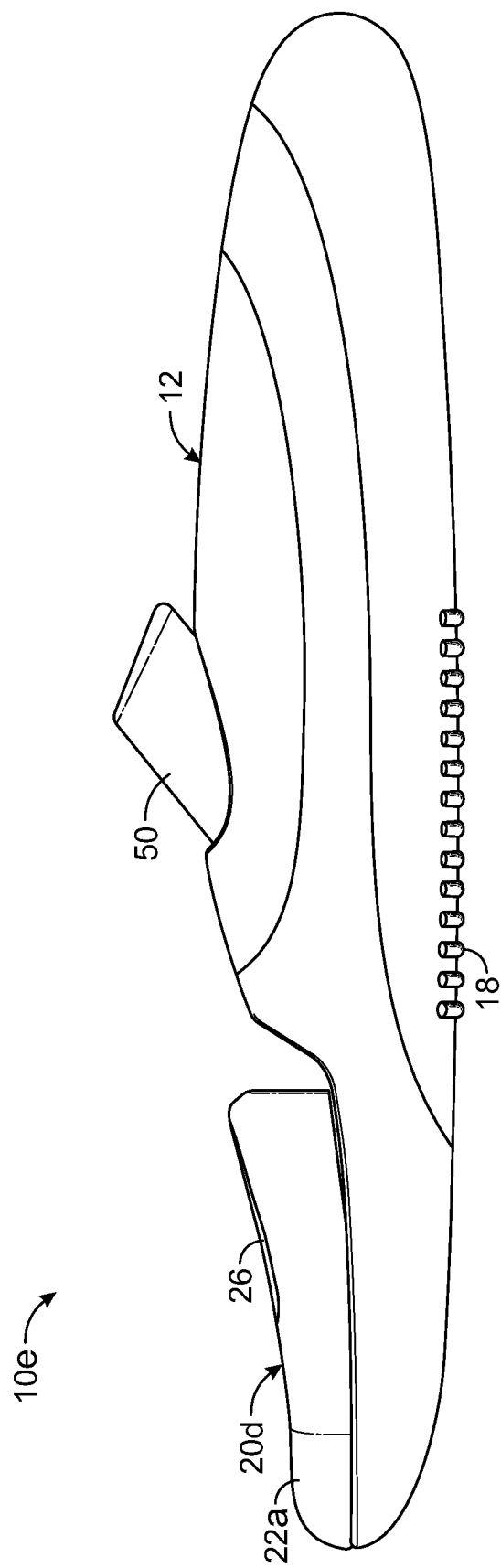
FIG. 45 is a left side plan view of the embodiment of FIG. 39 shown with the hatch or lid in the closed position.
Figure 46:
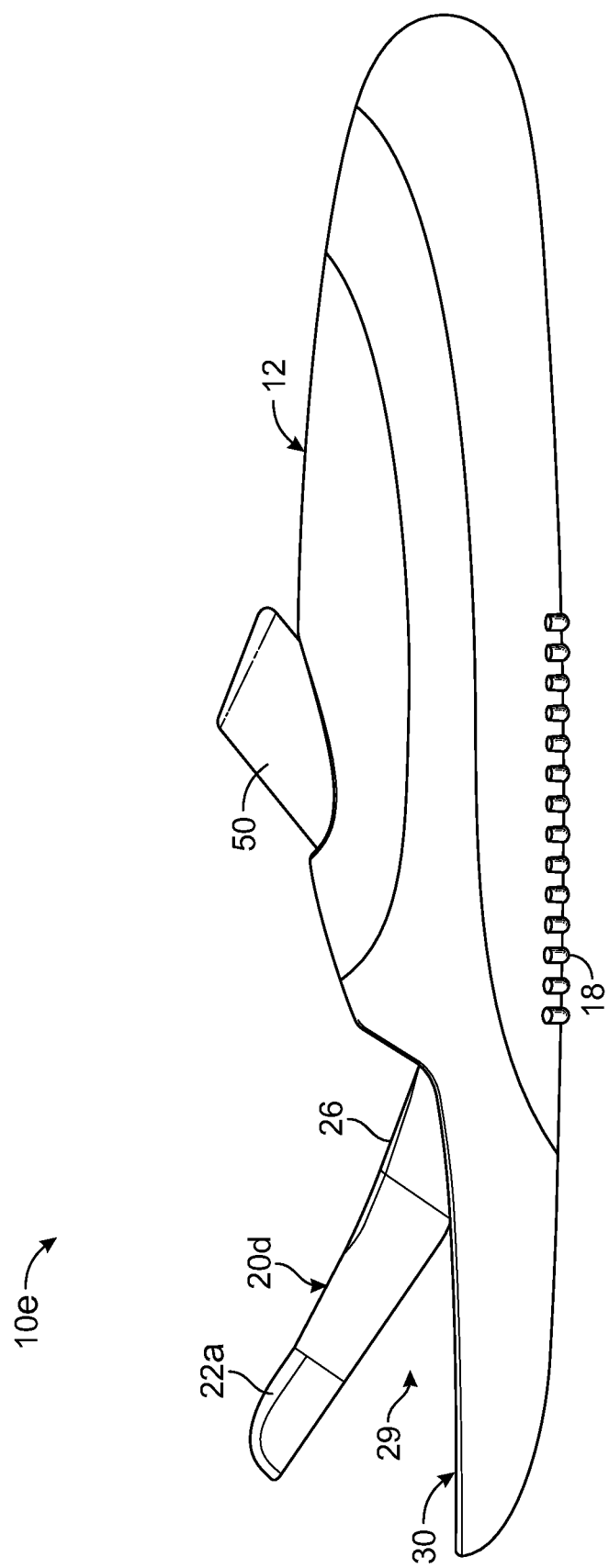
FIG. 46 is a left side plan view of the embodiment of FIG. 39 shown with the hatch or lid in the open position.
Figure 47:
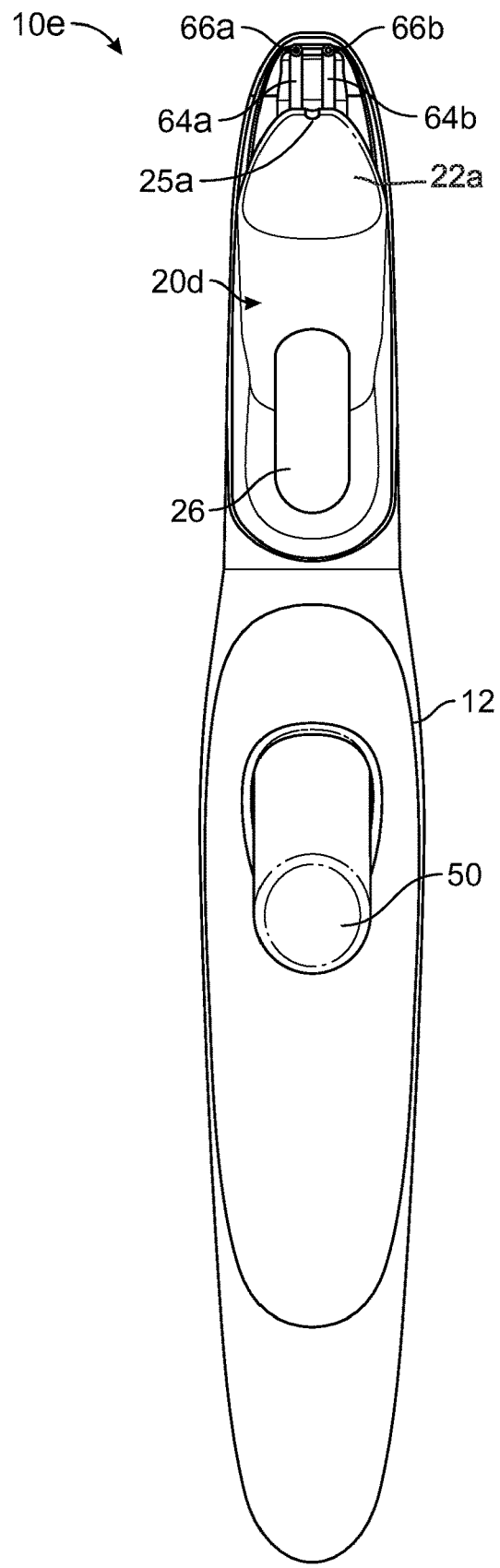
FIG. 47 is a top plan view of the embodiment of FIG. 39 shown with the hatch or lid in the open position.
Figure 48:
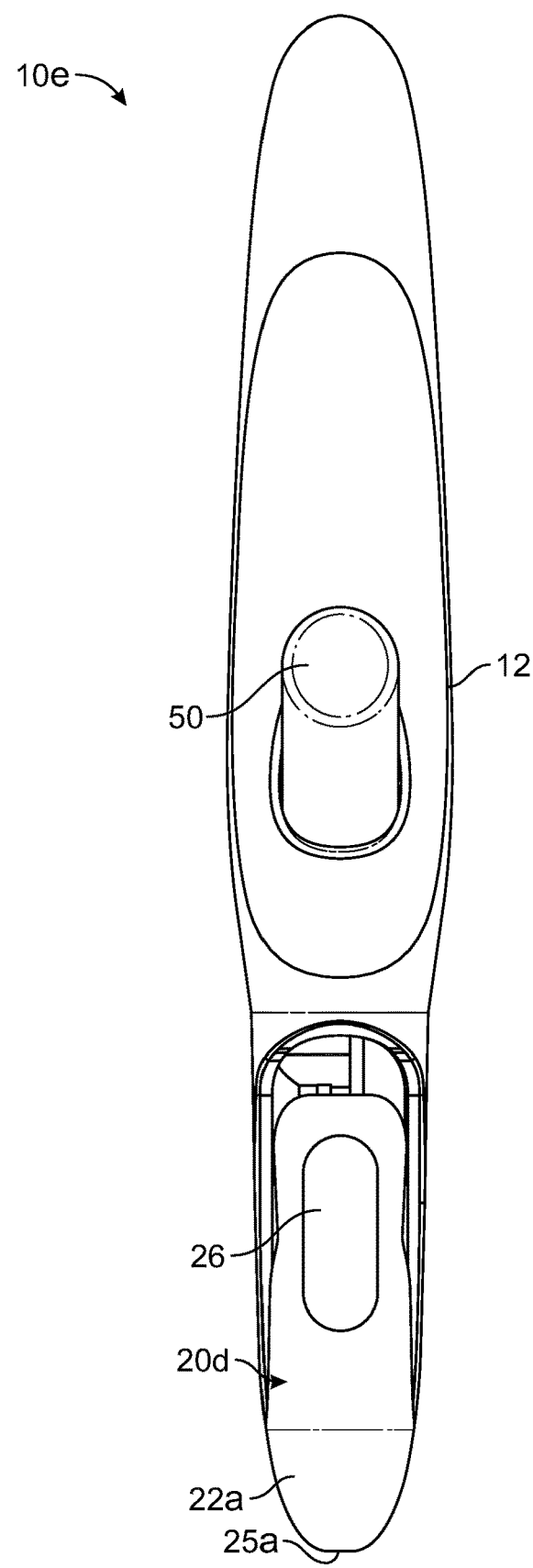
FIG. 48 is a top plan view of the embodiment of FIG. 39 shown with the hatch or lid in the closed position.
Figure 49:
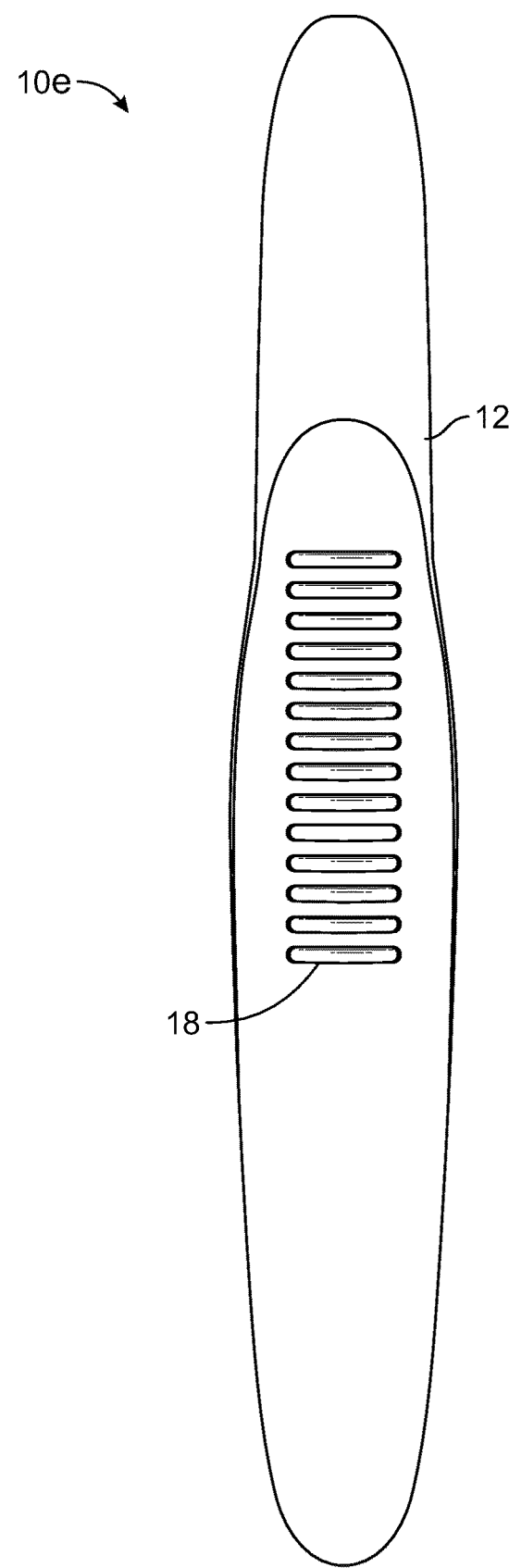
FIG. 49 is a bottom plan view of the embodiment of FIG. 39.
Figure 50:
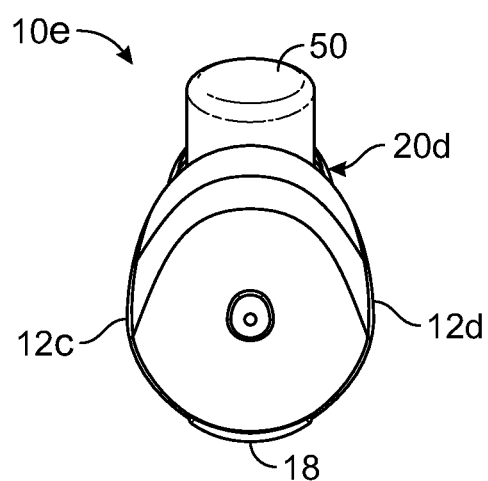
FIG. 50 is a rear end plan view of the embodiment of FIG. 39 shown with the hatch or lid in the open position.
Figure 51:
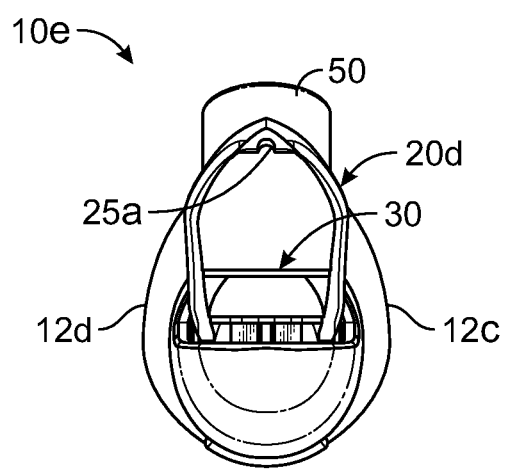
FIG. 51 is a front end plan view of the embodiment of FIG. 39 shown with the hatch or lid in the open position.
Figure 52:
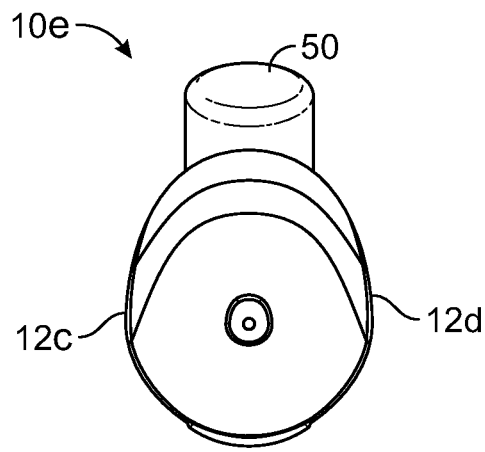
FIG. 52 is a rear end plan view of the embodiment of FIG. 39 shown with the hatch or lid in the closed position.
Figure 53:
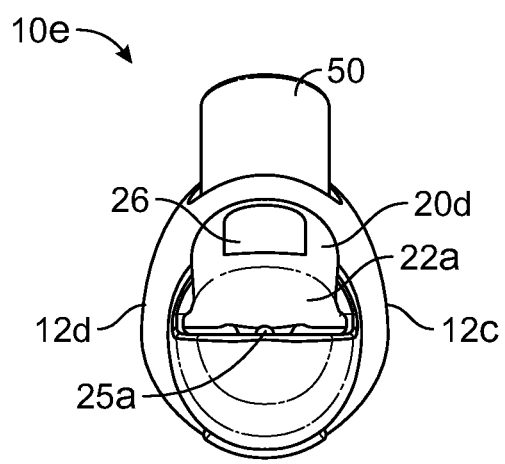
FIG. 53 is a front end plan view of the embodiment of FIG. 39 shown with the hatch or lid in the closed position.
Figure 54:
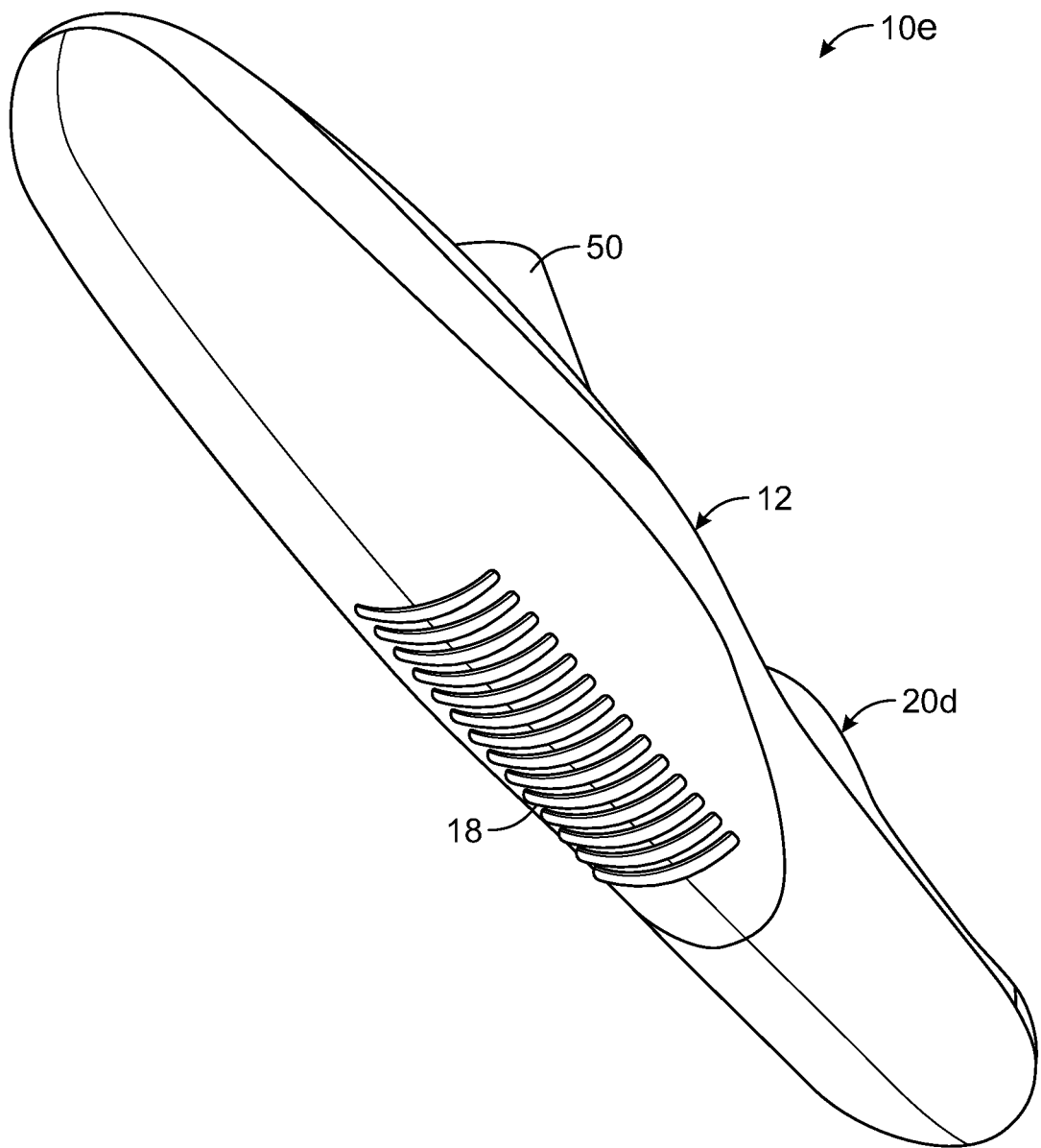
FIG. 54 is a bottom rear, right side perspective view of the embodiment of FIG. 39 shown with the hatch or lid in the closed position.
Figure 55:
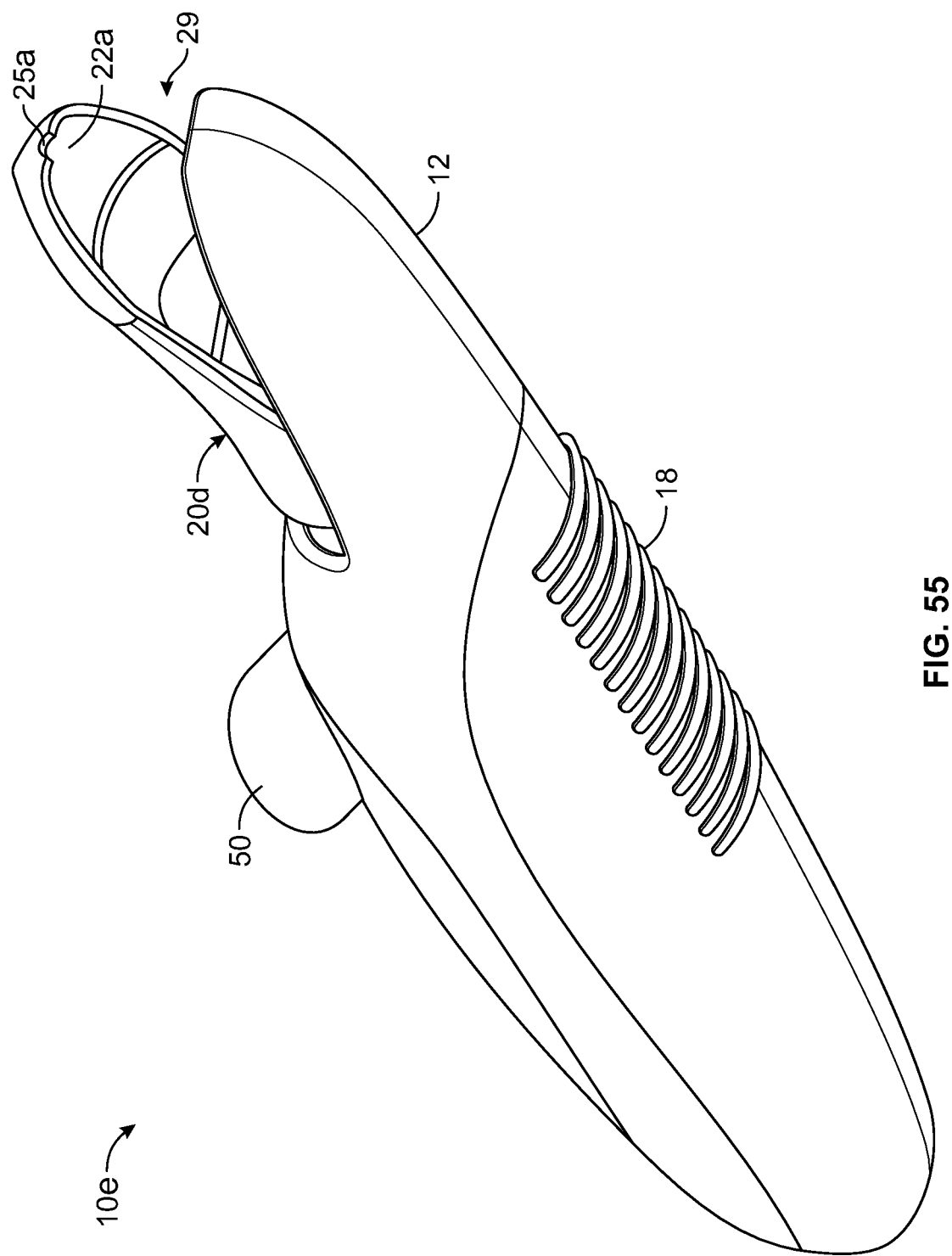
FIG. 55 is a bottom front, right side perspective view of the embodiment of FIG. 39 shown with the hatch or lid in the open position.
Figure 56:
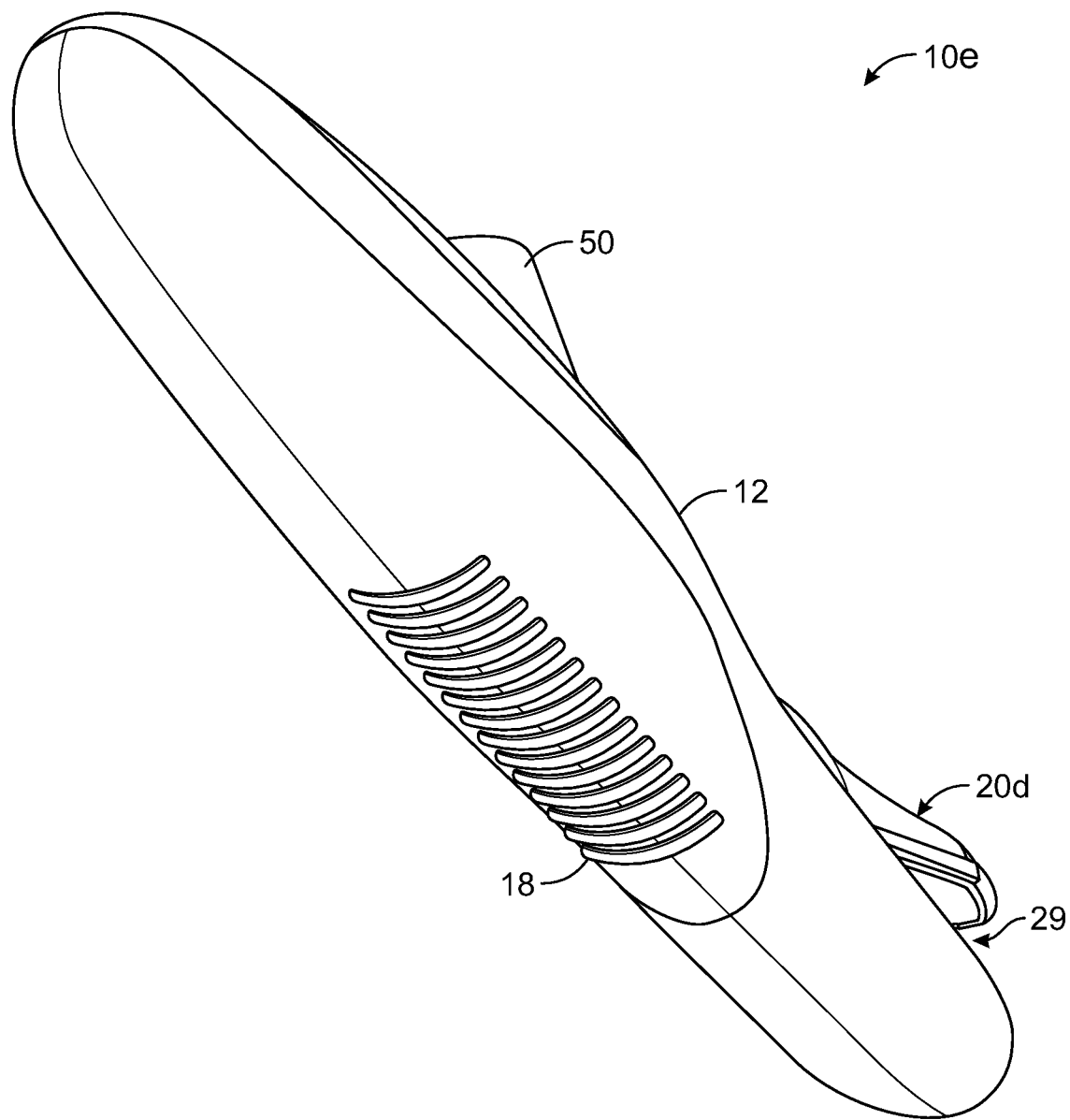
FIG. 56 is a bottom, right side perspective view of the embodiment of FIG. 39 shown with the hatch or lid in the open position.
Figure 57:
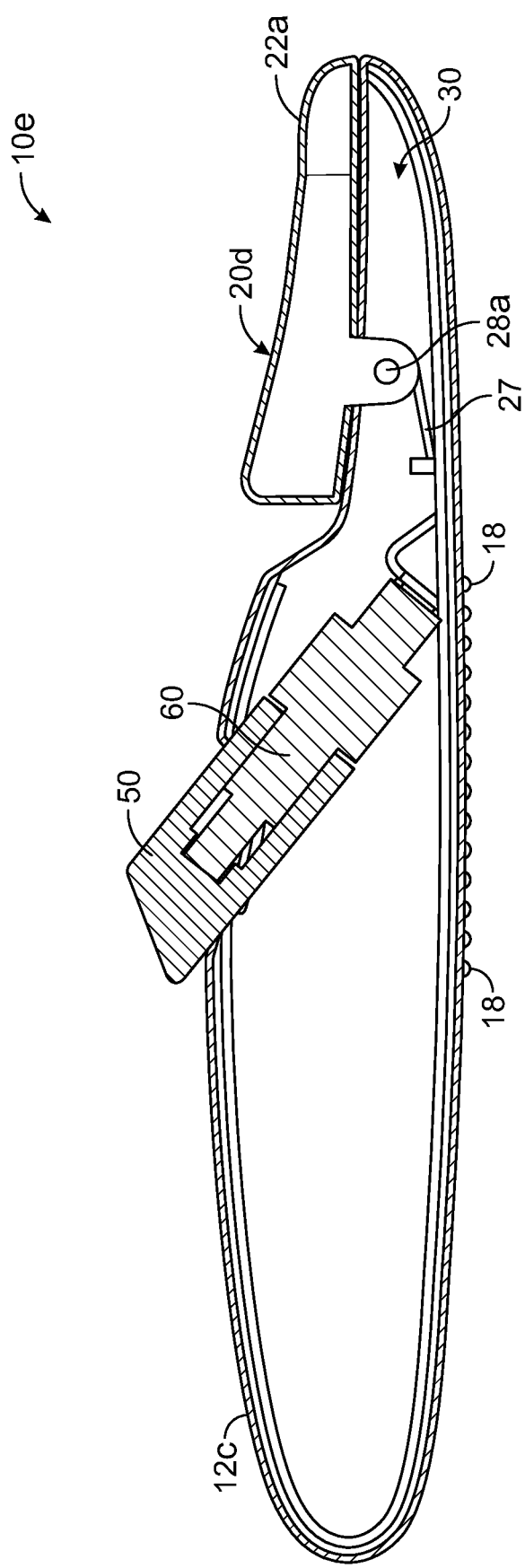
FIG. 57 is a right side cross-sectional plan view of the embodiment of FIG. 39 shown with the hatch or lid in the closed position taken along lines 57-57 of FIG. 44.
Figure 58:
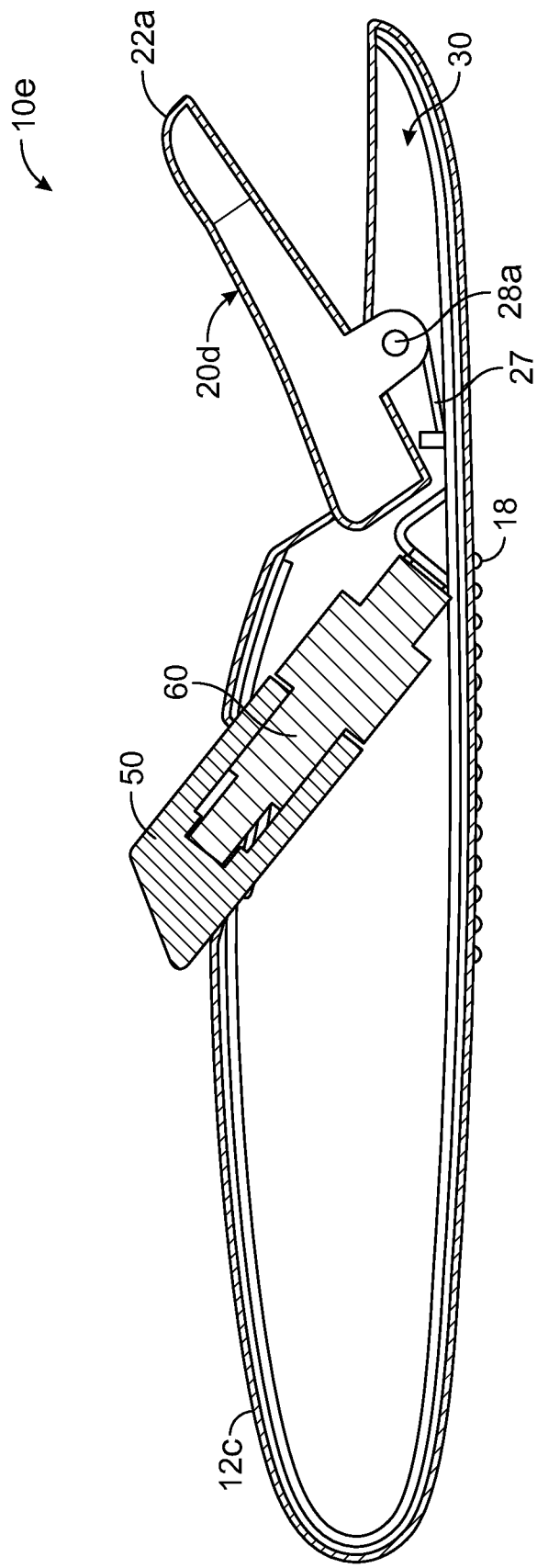
FIG. 58 is a right side cross-sectional plan view of the embodiment of FIG. 39 shown with the hatch or lid in the closed position taken along lines 58-58 of FIG. 43.
Figure 59:
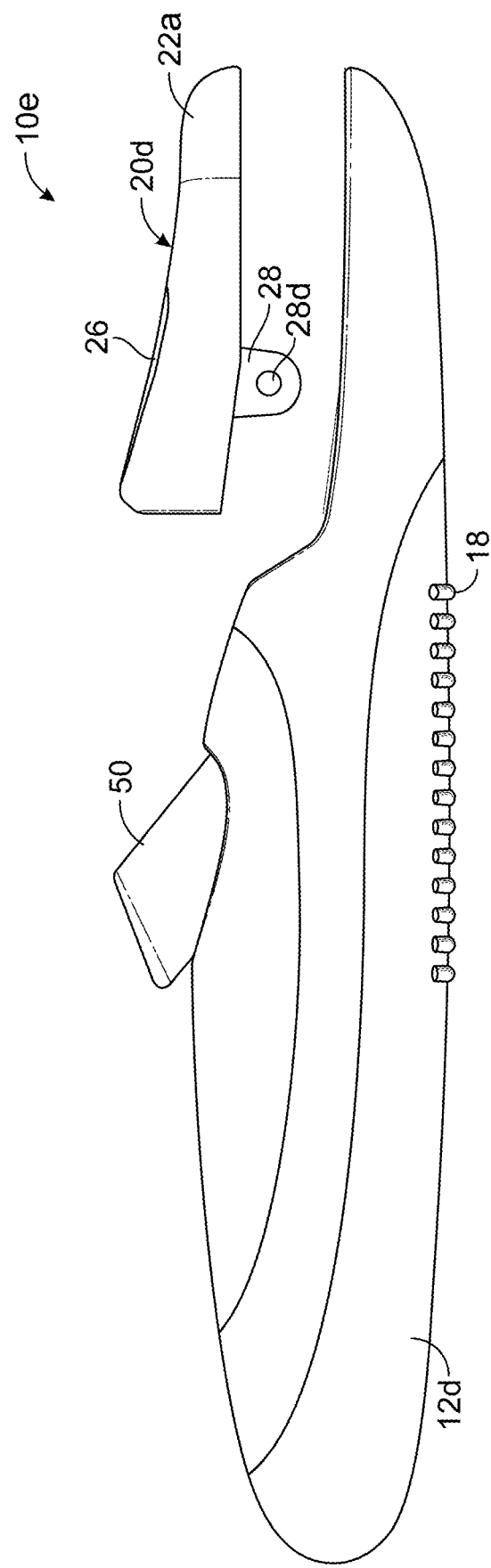
FIG. 59 is a right side, partially exploded plan view of the embodiment of FIGS. 39 and 44 shown with the hatch or lid in the closed position, but removed from the device in exploded view.
Figure 60:
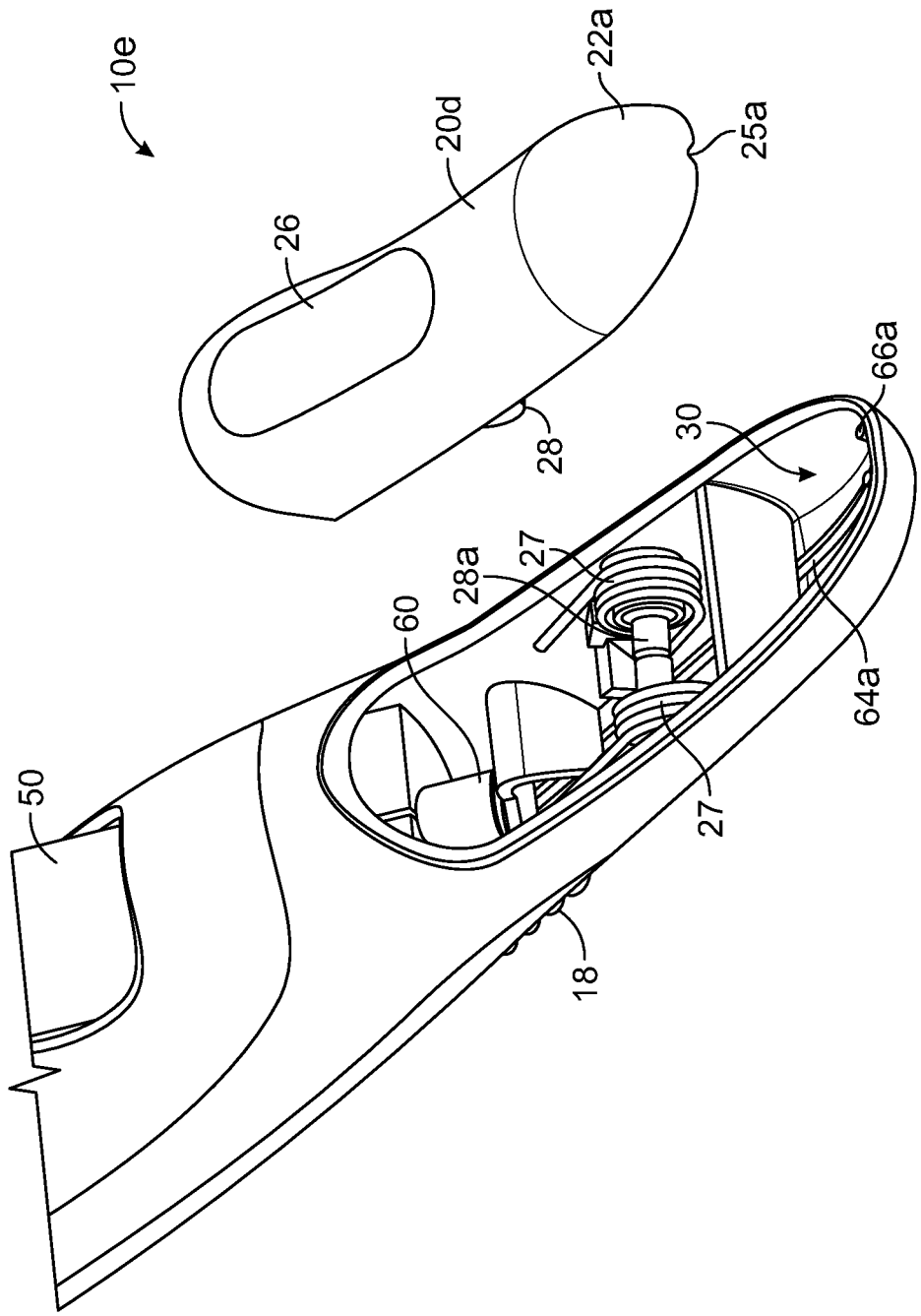
FIG. 60 is a front, right side, partially exploded perspective view of the embodiment of FIG. 39 shown with the hatch or lid in the closed position, but removed from the device in exploded view.
Figure 61:
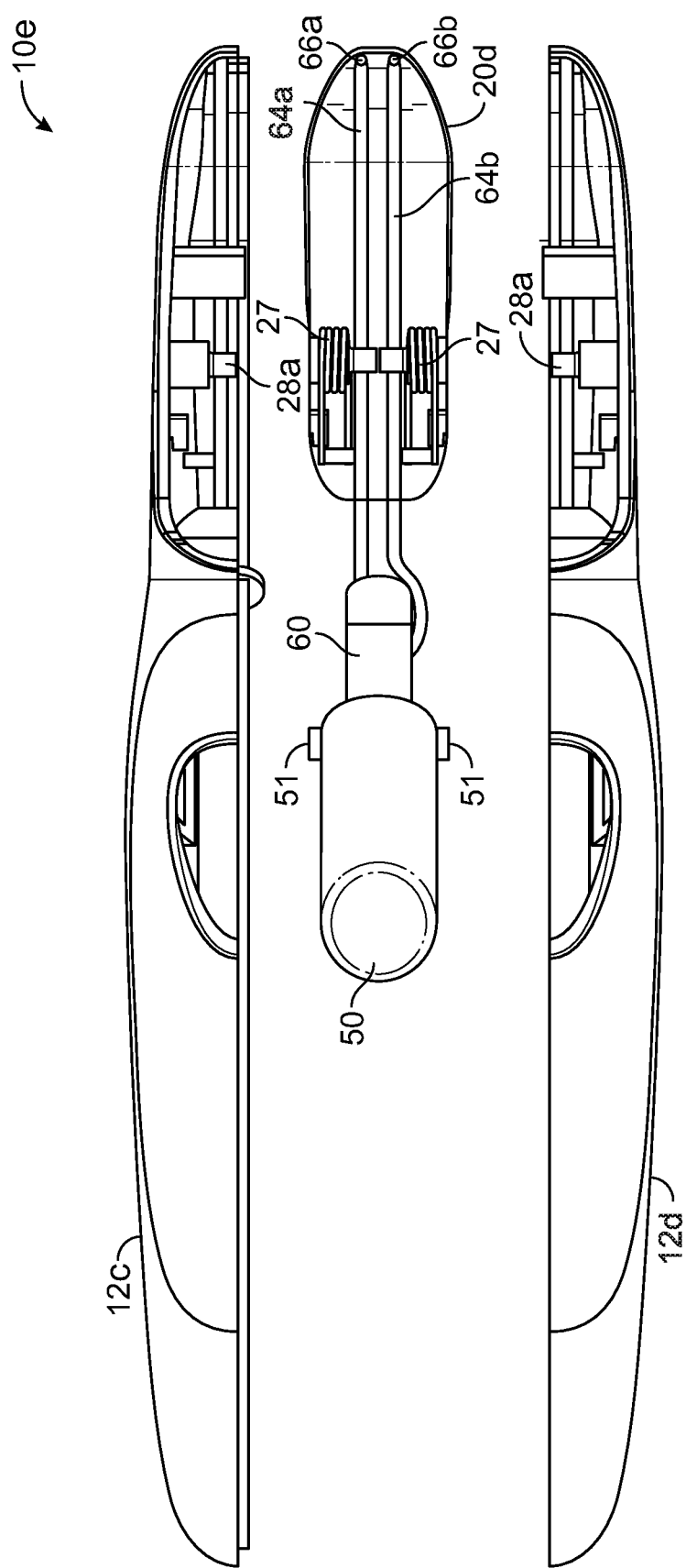
FIG. 61 is a top exploded plan view of the embodiment of FIGS. 39 and 48 shown with the hatch or lid in the closed position.
Figure 62:
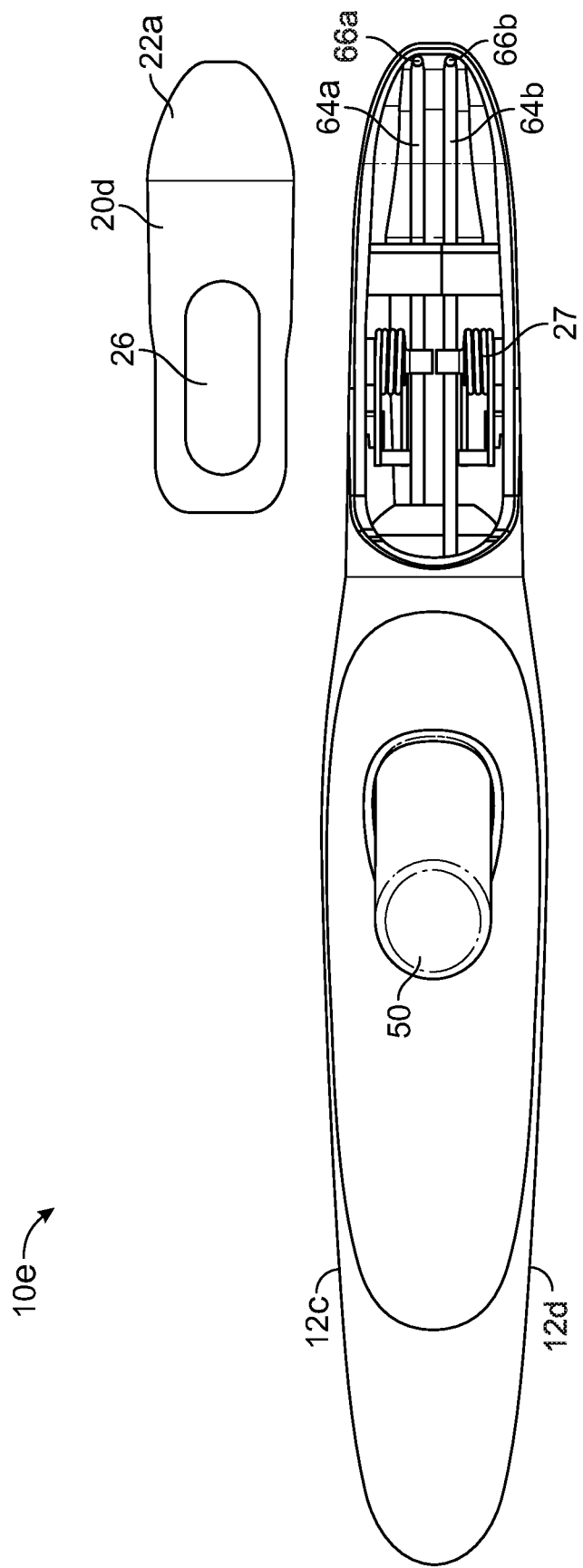
FIG. 62 is a top exploded plan view of the embodiment of FIGS. 39 and 48 shown with the hatch or lid in the closed position but removed from the device in exploded view.
Figure 63:
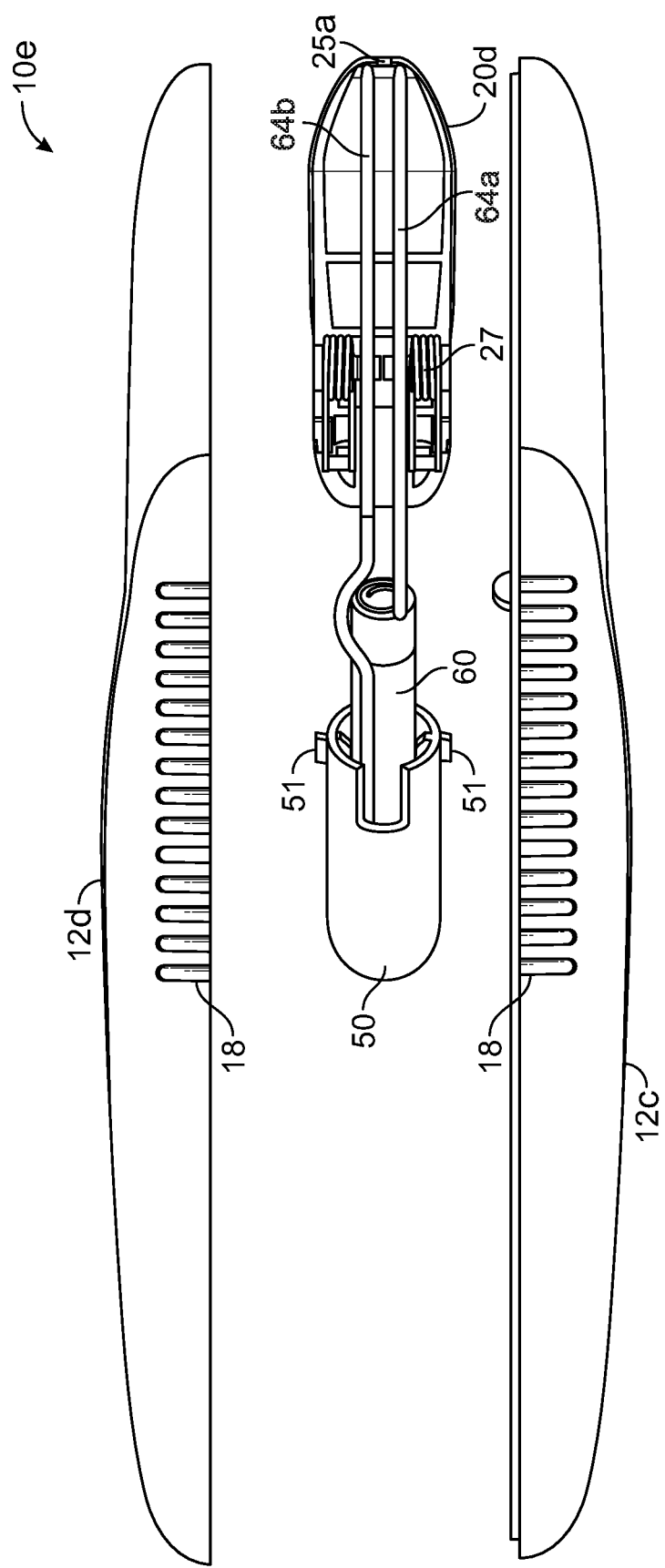
FIG. 63 is a bottom exploded plan view of the embodiment of FIGS. 39 and 49 shown with the hatch or lid in the closed position.
Figure 64:
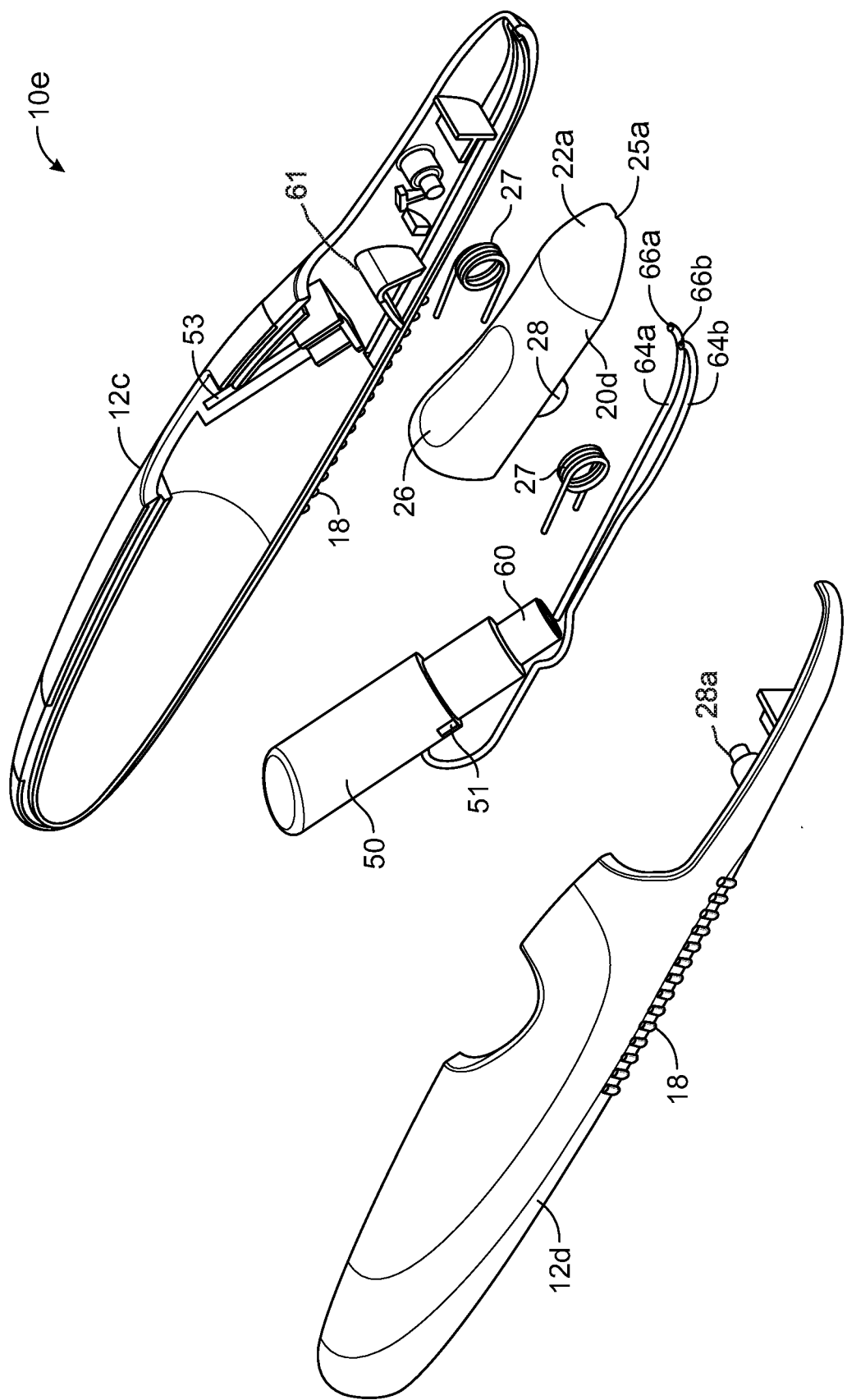
FIG. 64 is a front right exploded perspective view of the embodiment of FIG. 39 shown with the hatch or lid in the closed position.
Figure 65:
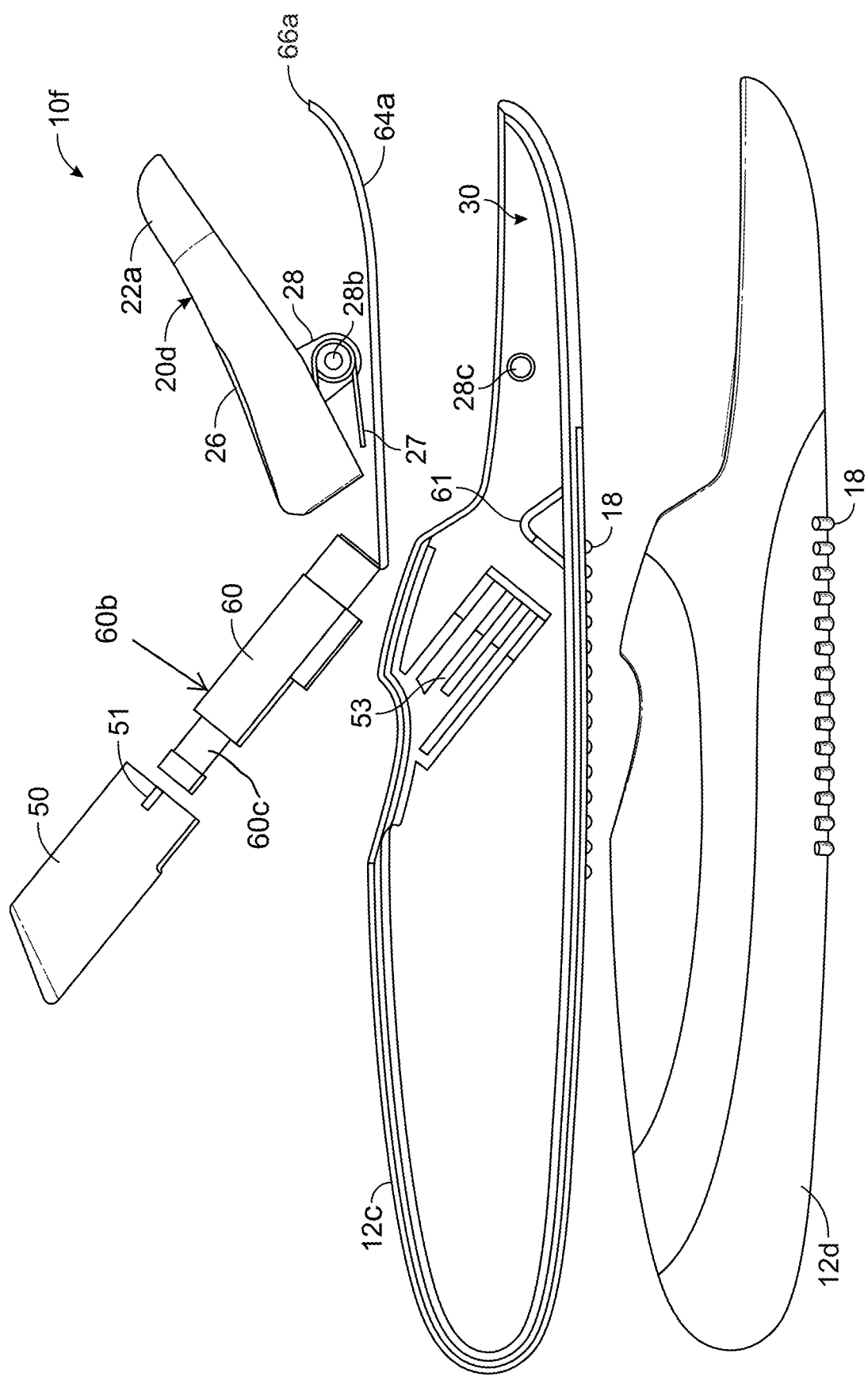
FIG. 65 is a right side exploded plan view of the embodiment of FIGS. 39 and 43 shown with the hatch or lid in the open position.
Figure 66:
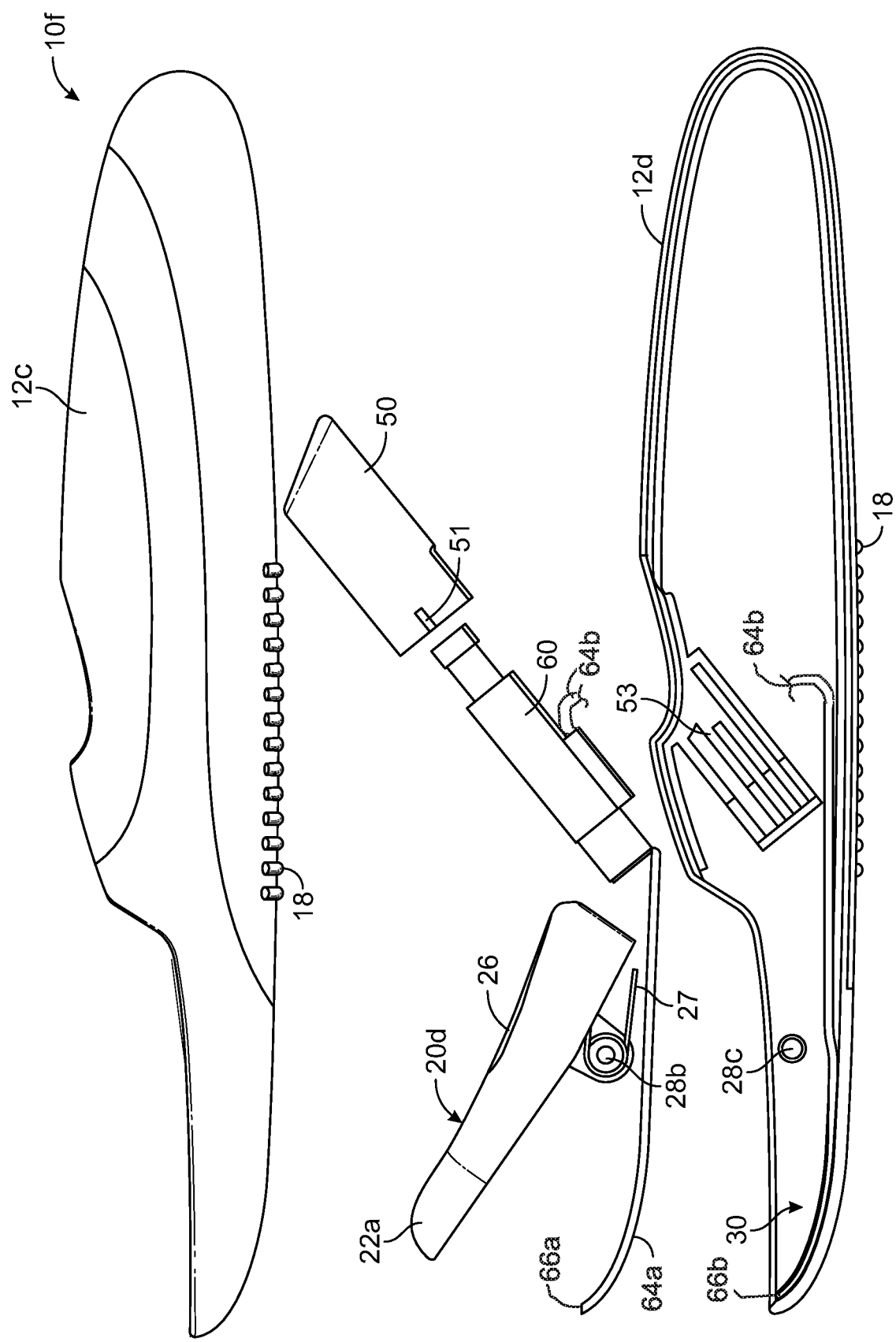
FIG. 66 is a left side exploded plan view of the embodiment of FIGS. 39 and 46 shown with the hatch or lid in the open position.

The device 10 of the present disclosure may also optionally contain a secondary circuit 70 illustrated in FIG. 24 with a DC power supply 72 (such as a battery) and an LED light 73 (shown only schematically). The user depresses a switch 71 (shown only schematically) located on the outside of housing 12 to activate an LED light 73 (not shown). The light emitted from the LED 73 will illuminate the encapsulation section 30 of the device 10. Use of the LED light 73 can assist the user in seeing the tick when using the device.

One exemplary piezoelectric high voltage generation device known in the art is that employed in electronic cigarette lighters, such as that described in Suzuki et al., U.S. Pat. No. 3,986,061, which is incorporated herein by reference in its entirety. Other suitable piezoelectric voltage generation elements are known in the art and could be adapted for use in the present invention.

For example, according to APC International, Ltd. (Mackeyville, Pa.) (americanpiezo.com), piezoelectric ceramics, when mechanically activated with pressure, tension or vibration, have the capacity to generate electric voltages sufficient to spark across an electrode gap. Piezoelectric ceramics are frequently used in this capacity to ignite a fuel source in lighters, gas stoves and welding equipment. Mechanical compression or tension on a poled piezoelectric ceramic element changes the dipole moment, creating a voltage. Compression along the direction of polarization, or tension perpendicular to the direction of polarization, generates voltage of the same polarity as the poling voltage. Tension along the direction of polarization, or compression perpendicular to the direction of polarization, generates a voltage with polarity opposite that of the poling voltage. These actions are generator actions—the ceramic element converts the mechanical energy of compression or tension into electrical energy.

Two common applications of piezo generators are in the push button cigarette lighters and gas BBQ grills. In these applications, pressing a button causes a spring-loaded hammer to apply a mechanical force to a rod-shaped single-layer piezoelectric ceramic. As a result of the piezoelectric effect, the ceramic element produces a voltage that passes across a small spark gap causing the fuel source to ignite. Electrical energy in a rod-shaped single-layer piezo generator is released very quickly, is very high voltage, and very low current. Piezoelectric ignition systems are small and simple, long lasting and require little maintenance. PZT, or lead zirconate titanate (Pb[Zr(x)Ti(1−x)]O3), such as offered by APC International, Inc. is one of the world's most widely used piezoelectric ceramic materials. Hard (high power) PZT ceramic powders are used when high power characteristics are required, including applications such as the generation of high-voltage energy. Important powder characteristics include a high piezoelectric charge constant (d33); a higher mechanical quality factor that reduces mechanical loss and enables a lower operating temperature; a low dissipation factor that ensures cooler, more economical operation; high dielectric stability; and low mechanical loss under demanding conditions. Simple, yet suitable, piezoelectric ignitors are available commercially from, e.g., APC International, Inc.

The present invention differs from Daniell and Butler as it does not apply any form of compression to the tick, reducing, if not eliminating, the potential for injection of toxic substances into the host. Secondly, the present invention uses lethal neutralization, via piezoelectric shock, which automatically prompts a natural response by the tick—an immediate release from its host. Thirdly, the device of the present disclosure reduces, if not eliminates, the potential for the tick to deposit eggs onto its host as the entire tick will be fully encapsulated upon neutralization. Fourth, this encapsulation element also provides for easy and safe disposal of the deceased tick. Fifth, this encapsulation serves to protect the user, as contact between the user and the tick does not occur, and, is not required for successful neutralization.

The present invention differs from Sandels. The intention of the Sandels instrument is to kill a tick through suffocation, by first creating a vacuum (air-free/suction) on the host's skin surface, followed by dousing the tick with a liquid (fat/oil). The device of the present invention is a very different tick removal tool, as it does not require suction, liquids, or application waiting time, in order to achieve successful tick removal. Secondly, the probability of successful tick extermination must be considered. Fur located on the surface of animal skin or hair located on the surface of human skin pose challenges in successfully creating the required vacuum (suction) on the skin's surface. Performance of the device of the present invention is not affected by the presence of fur or hair as the piezo electrical charge fills the encapsulation chamber immediately, rendering the tick dead without the need to create additional conditions (e.g. suction, liquid application). Thirdly, safety is an additional concern, most importantly regarding the (potential) presence of disease. Once the suction tool is released from the host's skin, the tick is no longer contained. The risk of losing the tick (falling away upon release, dropped prior to disposal, etc.), and the possible spread of disease through direct contact, is dangerous. These risks are mitigated when using the device of the present invention. The tick is locked inside of the encapsulation cup, which is controlled by fully loaded springs. This cup cannot be opened until the user deliberately presses the 'open' button, thereby releasing the closure spring. This feature allows for controlled and safe disposal of the specimen, ensuring that diseases are not transferred to the host or the user or surrounding environment.

The present invention differs from Mezger. The intention of the Mezger instrument is to kill a tick through electrocution. The design of its extremities/branches, which open laterally, create an opportunity for breakage. The internal parts of the device of the present invention are housed within one full unit, they are not exposed, rendering it more functional and easier to use. The easier a tool is to operate, the faster one can neutralize the tick, therefore reducing the possibility of disease transference. Secondly, the Mezger tool depends on an external energy source, specifically, a battery. The device of the present invention is self-energizing, using internal crystals and a piezo electric charge to create as well as hold a charge for use. This system renders the device of the present invention available for use at all times, versus battery-dependent tools. Thirdly, the effectiveness of a tool must be considered. The design of the Metzger tool utilizes extremities/branches that do not allow for complete isolation of the tick. There is no guarantee that the host is not receiving the electrical charge as well as the tick. The device of the present invention employs a tick container that fully encapsulates the tick, and the electrical charge, with no contact made to the host.

The present invention also differs from Weiner. The intention of the Weiner instrument is to kill a tick through electrical heat or chemical application. These pincers/pliers have round electrical end points, electrical conductors allowing for the electrocution of the tick. These pincers are relatively cumbersome, which could impede the successful termination of the tick. The improved TickZapper device of the present disclosure eliminates these possibilities though easy application. It does not reply upon the user's ability to securely hold the tool on the tick. The new TickZapper device's containment cup—which is locked into place by its springs—captures the tick upon closure at which time the lethal electrical voltage is then applied with an easy push of the trigger button. Secondly, unlike the abovementioned Weiner tool, which requires multiple steps to fully kill the tick, (capture, application of chemicals or heat, then neutralization), the device of the present invention works without a waiting period. There is virtually no time lapse between the moment that the present device contains the tick and its lethal neutralization. The destruction element is triggered substantially simultaneously with, or immediately after, the closure of the containment hatch 20—the only time delay being for the user to move his or her thumb from the hatch button 26 to the trigger button 50 all located within the reach of the thumb without having to readjust the hand holding the device 10. Thirdly, the use of a heating element or chemical agent to kill a tick creates the potential for skin burning or chemical reaction upon the host's skin. The device of the present invention uses no chemicals and no heat, only piezoelectric stimulation.

The present invention also differs from Schaumburg. The intention of the Schaumburg tool is to kill and remove ticks using a lethal piezoelectric neutralization. Although this a progressive way in which to kill ticks, the device of the present invention provides the user a more efficient tool that offers a stronger voltage, ensuring a complete neutralization of the tick on the first attempt. Secondly, the risk of contracting disease from the tick, or having the tick's eggs dropped onto the host's skin as the neutralization proceeds is minimized or avoided with the present device because neutralization will occur quickly after closure of the encapsulation area without the need to repeat the application of the voltage additional times—again, the only time delay being for the user to move his or her thumb from the hatch button 26 to the trigger button 50 all located within the reach of the thumb without having to readjust the hand holding the device 10. Schaumberg teaches that one must first hold the body and head of the tick and enclose the tick within the enclosed space created by two parts (Schaumburg elements 9, 16 of FIGS. 1-3) while doing so in a manner that creates no compression on the tick. One then must separately press a separate ignition switch (cap) (Schaumburg element 23 of FIGS. 1-3) to administer the electric shock. However, the ignition switch is located at the distal end of the device along the longitudinal axis and is difficult to trigger with the same hand that holds the device thereby making administration of the electric shock (pushing of the distal end toward the proximal end along the longitudinal axis) more cumbersome while also increasing the chances of jostling and aggravating the tick prior to administration of the shock.

Further, Schaumburg teaches that the enclosed space could be heated or cryogenically cooled to kill the tick, or an anesthetic fluid could be injected into the tick in lieu of the use of the piezoelectric shock. Thirdly, the materials and housing of the device of the present invention are made of industrial strength materials which are much more durable than those used to make the abovementioned tool. Fourth, the device of the present invention is able to self-generate its energy source, making it available to use at all times. Finally, the Schaumberg device has difficulty handling larger ticks owing to the small size of the cup structure. The hatch 20 and chamber 30 design of the present invention readily permits use of the device on large and small ticks.

In an additional embodiment, the tick removal device of the present disclosure can be manufactured to be a single use, disposable device. In other embodiment, the device 10 is readily reuseable.

Referring now to FIGS. 39-66 there is shown another embodiment, similar in nature to that described in connection with the prior figures. In this embodiment there is shown details of one embodiment of a tick removal device 10e. As will be apparent from the various views, this embodiment also employs a body 12, a hatch or lid 20d rotatably connected to the body via axel mounts 28a and spring tensioned by springs 27, such as those sourced from Lee Springs (www.leespring.com) as torsion spring part numbers LTR028E 01 M and/or LTL028E-01-M (rated to produce about 62 N-mm of torque). Although this embodiment illustrates the use of two separate springs 27, it will be understood that other spring arrangements can be employed, such as a custom made spring designed to fit within the chamber 30, to provide the desired springe resistance. As with the other embodiments, a piezoelectric device 60 is mounted therein in suitable housing having a base plate 61 and is activated by the pressing down on button 50 along the trigger button axis 54. The piezoelectric device, when activated, sends an electrical charge through electrode wires 64a, 64b, and across electrode tips 66a, 66b. In this embodiment, the hatch or lid 20d may be further outfitted with a small notch 25a or opening to permit the surrounding of the tick's head. In this embodiment, the hatch or lid 20d could be opaque, solid, or completely or partially transparent. For example, in one embodiment, the tip section of the hatch 22a is a transparent section that may also contain a built in magnifying lens to permit easy viewing of the contents of the hatch receiving chamber 30.

Figure 67:
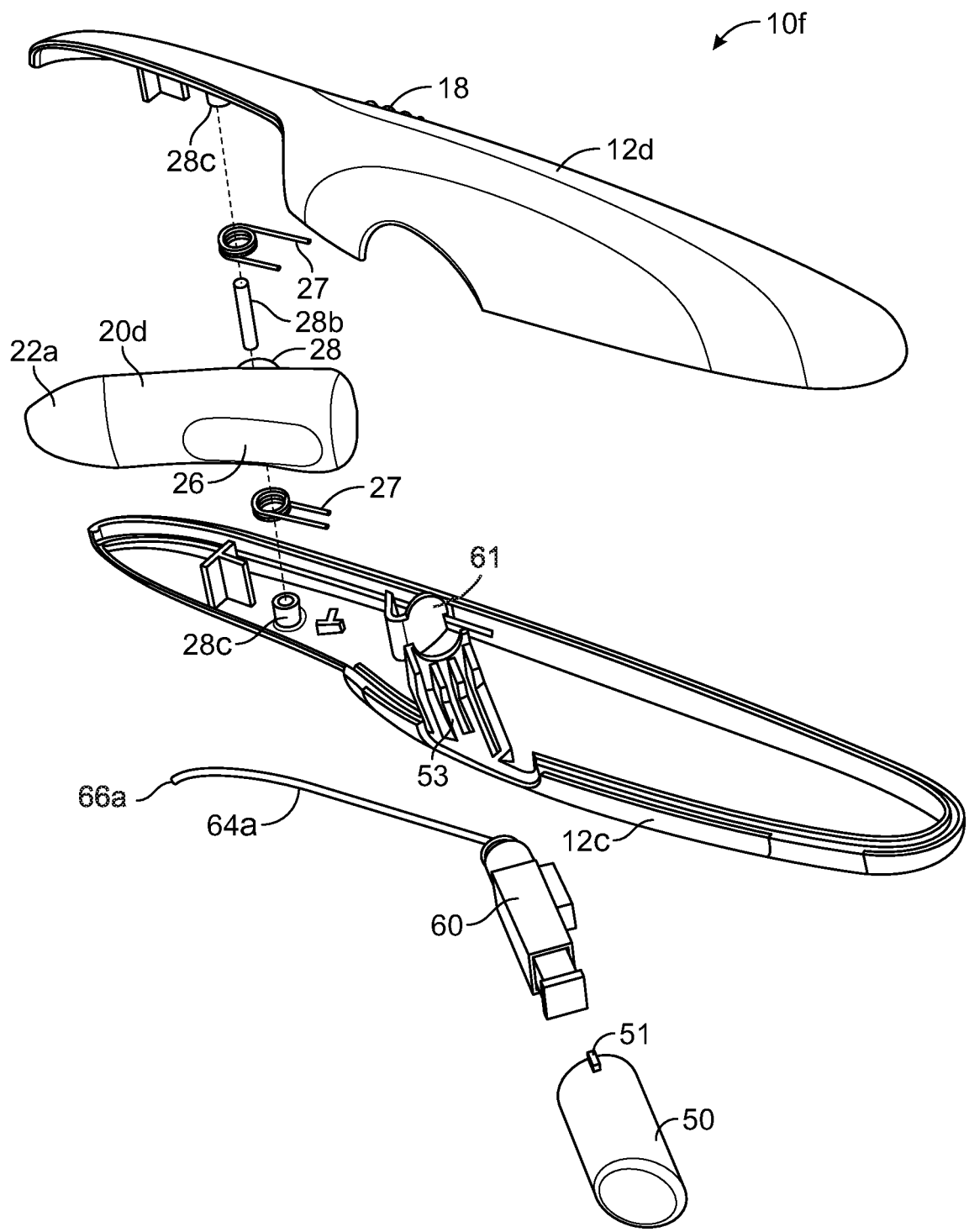
FIG. 67 is a rear right exploded perspective view a hand operated reaching device for removing ticks from animals or humans according to another embodiment of the present disclosure shown with the hatch or lid in the closed position and pivotable on a fixed axel.
Figure 68:
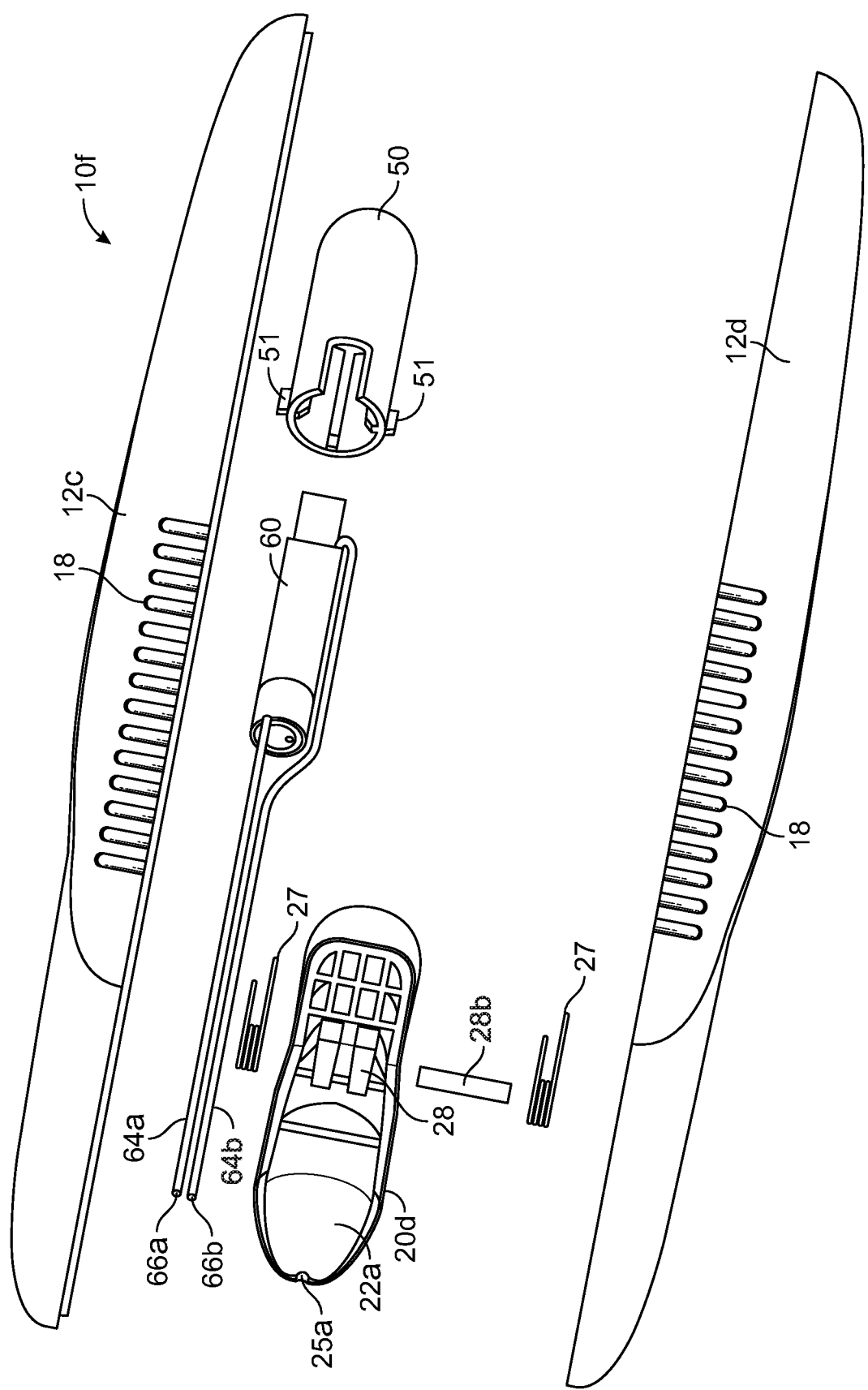
FIG. 68 is a bottom exploded plan view of the embodiment of FIG. 67.
Figure 69:
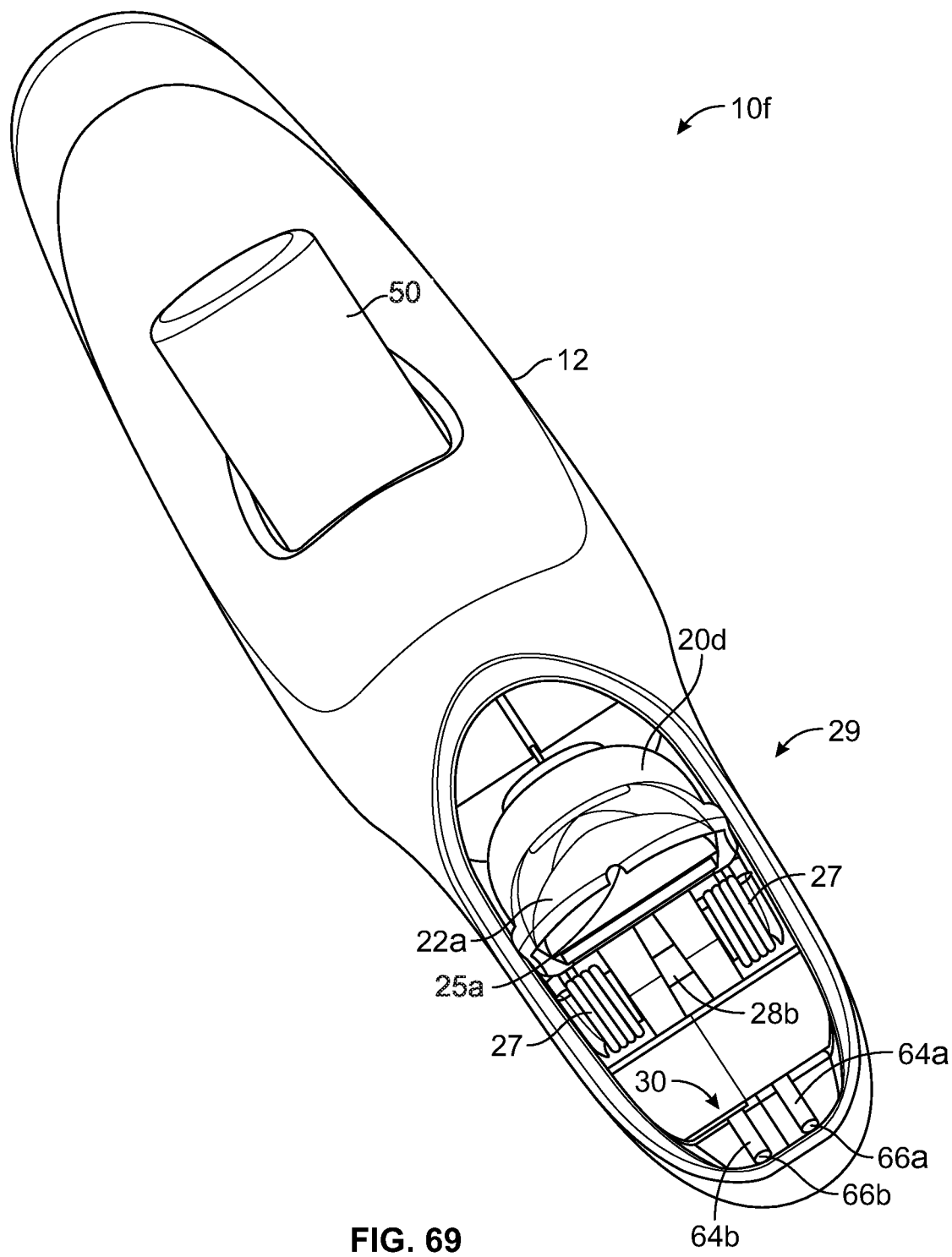
FIG. 69 is a right front perspective view of the embodiment of FIG. 67 shown with the hatch or lid in the open position.

Referring now to FIGS. 67-69 there is shown another embodiment, similar in nature to that described in connection with the prior figures. In this embodiment there is shown details of one embodiment of a tick removal device 10f that employs a solid axel 28b mounted between the inside walls (into mounts 28c) of the device housing upon which the hatch or lid 20d is permitted to rotate between its closed and open positions.

All references referred to herein are incorporated herein by reference. While the apparatus, systems and methods of this invention have been described in terms of preferred or illustrative embodiments, it will be apparent to those of skill in the art that variations may be applied to the process and system described herein without departing from the concept and scope of the invention. All such similar substitutes and modifications apparent to those skilled in the art are deemed to be within the scope and concept of the invention. Those skilled in the art will recognize that the method and apparatus of the present invention has many applications, and that the present invention is not limited to the representative examples disclosed herein. Moreover, the scope of the present invention covers conventionally known variations and modifications to the system components described herein, as would be known by those skilled in the art.

I claim:

1. A hand held reaching device for removing ticks that are fixed to the skin of an animal or human host comprising:
    a. an external housing having a front proximal end and a rear distal end oriented along a longitudinal axis, a top side and an underside, the external housing being suitably sized to permit a user to hold and operate the hand held reaching device in a first single hand, b. a tick encapsulation zone defined by a fixed portion of the front end of the external housing, and an openable and closable lid section capable of moving from an open position to a closed position to create a closed enclosure within the front end of the external housing, the lid section capable of closing around the tick while the tick is attached to the skin of the host, the lid section having a front lid end and a rear lid end and being pivotally mounted on the top side of the reaching device external housing between the front lid end and the rear lid end and further comprising a lid button on the lid rear end capable of being pushed with a thumb on the user's first single hand to pivotally open the lid section and a metal spring mechanism to provide resistance sufficient to maintain the lid section in a closed position unless the lid button is pressed inwardly by the user's thumb on the user's first single hand against the resistance of the spring mechanism, c. a piezoelectric crystal voltage generation device located within the external housing, the piezoelectric crystal voltage generation device further comprising a piezoelectric crystal contained within a piezoelectric device housing, a hammer located within the piezoelectric device housing capable of striking the piezoelectric crystal to generate an electrical voltage sufficient to electrocute the tick after a first striking of the hammer, and a hammer activation button located on the piezoelectric device housing, the hammer activation button capable of engaging the hammer, d. two lead wires electrically engaged at first proximal ends with the piezoelectric crystal and extending from the piezoelectric crystal and having second distal ends exposed to create two electrode tips mounted within the tick encapsulation zone in gapped relationship proximate to the housing front proximal end to create an electrode gap between the two electrode tips, and e. a trigger button, mounted on the top side of the reaching device external housing and extending outward and toward the external housing rear distal end and oriented about a trigger axis intersecting with the longitudinal axis of the housing to form a trigger axis angle taken from a proximal side of the trigger relative to the longitudinal axis, for engaging the hammer activation button on the piezoelectric device housing to send the electrical voltage through the lead wires and across the electrode gap to electrocute the tick, the trigger button being located distal to the lid section, the trigger button being mounted proximate the lid button between the lid button and the rear distal end of the reaching device, wherein in use, the hand held reaching device is configured to permit the user to hold the hand held reaching device with the first single hand, to press the lid button with the user's thumb on the user's first single hand, to then move the user's thumb on the user's first single hand to the trigger button and to use the thumb on the user's first single hand to press the trigger button inward along the trigger axis, the hand held reaching device being configured to administer an electrical shock to the tick when the trigger button is pressed to cause the tick, including its mouthparts, to detach from the host's skin such that the tick falls into, and is contained in, the encapsulation zone of the hand held reaching device.

2. The tick removal device of claim 1 wherein the lid section is transparent.

3. The tick removal device of claim 2 wherein the transparent lid section further comprises a magnification zone.

4. The tick removal device of claim 1 wherein the trigger axis angle is 135°.

5. The tick removal device of claim 1 wherein the trigger axis angle ranges between 120° to 150°.

6. The tick removal device of claim 1 further comprising gripping surfaces on the external housing.

7. The tick removal device of claim 1 wherein the electrical voltage is 13,000 volts or higher.

\* \* \* \* \*